(12) United States Patent
Eckhardt et al.

(10) Patent No.: US 8,309,597 B2
(45) Date of Patent: Nov. 13, 2012

(54) 1,1'-DIADAMANTYL CARBOXYLIC ACIDS, MEDICAMENTS CONTAINING SUCH COMPOUNDS AND THEIR USE

(75) Inventors: Matthias Eckhardt, Biberach (DE); Bradford S. Hamilton, Biberach (DE); Frank Himmelsbach, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/054,949

(22) PCT Filed: Jul. 24, 2009

(86) PCT No.: PCT/EP2009/059573
§ 371 (c)(1),
(2), (4) Date: Feb. 23, 2011

(87) PCT Pub. No.: WO2010/010174
PCT Pub. Date: Jan. 28, 2010

(65) Prior Publication Data
US 2011/0269736 A1 Nov. 3, 2011

(30) Foreign Application Priority Data
Jul. 25, 2008 (EP) .................................. 08161151

(51) Int. Cl.
| | | |
|---|---|---|
| *A61K 31/40* | (2006.01) | |
| *A61K 31/445* | (2006.01) | |
| *A61K 31/397* | (2006.01) | |
| *A61K 31/5375* | (2006.01) | |
| *C07D 211/08* | (2006.01) | |
| *C07D 205/04* | (2006.01) | |
| *C07D 265/30* | (2006.01) | |

(52) U.S. Cl. ................. 514/429; 514/210.01; 514/231.2; 514/319; 544/106; 546/192; 548/528; 548/950

(58) Field of Classification Search .................. 548/528, 548/950; 514/429, 210.01, 231.2, 319; 546/192; 544/106
See application file for complete search history.

(56) References Cited

U.S. PATENT DOCUMENTS
| | | | |
|---|---|---|---|
| 3,378,587 A | 4/1968 | Reinhardt | |
| 4,043,927 A | 8/1977 | Duling et al. | |

FOREIGN PATENT DOCUMENTS
| | | | |
|---|---|---|---|
| EP | 1935420 A1 * | 6/2008 | |
| JP | 2007140188 A | 6/2007 | |
| WO | 0155063 A1 | 8/2001 | |

OTHER PUBLICATIONS

International Search Report and Written Opinion for PCT/EP2009/059573 mailed Oct. 9. 2009.
Abstract in English for JP2007140188 publication date 2007.

* cited by examiner

*Primary Examiner* — Kamal Saeed
*Assistant Examiner* — Janet L Coppins
(74) *Attorney, Agent, or Firm* — Michael P. Morris; David L. Kershner

(57) ABSTRACT

The present invention relates to compounds defined by formula (I) wherein the group R is defined as in claim 1, possessing valuable pharmacological activity. Particularly the compounds are inhibitors of 11β-hydroxysteroid dehydrogenase (HSD) 1 and thus are suitable for treatment and prevention of diseases which can be influenced by inhibition of this enzyme, such as metabolic diseases.

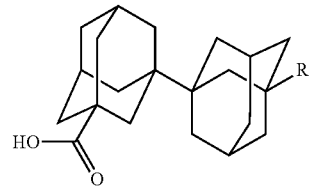

14 Claims, No Drawings

1,1'-DIADAMANTYL CARBOXYLIC ACIDS, MEDICAMENTS CONTAINING SUCH COMPOUNDS AND THEIR USE

The present invention relates to compounds derived from the following chemical scaffold which is structurally defined by the formula I

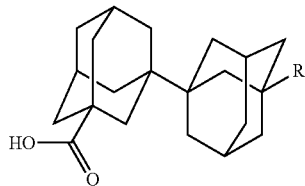

wherein the group R is as defined hereinafter, including the tautomers, the stereoisomers, the mixtures thereof and the salts thereof. The invention further relates to pharmaceutical compositions containing a compound of formula I according to the invention as well as the use of a compound according to the invention for preparing a pharmaceutical composition for the treatment of metabolic disorders. In addition, the invention relates to processes for preparing a compound according to the invention.

In the literature, compounds which have an inhibitory effect on the enzyme 11β-hydroxysteroid dehydrogenase (HSD) 1 are proposed for the treatment of the metabolic syndrome, in particular diabetes type 2, obesity, and dyslipidemia.

In the WO 2001/055063 bisadamantane compounds and derivatives are described as having advantageous properties in heat resistance, optical properties and solubility so that they are useful as optical materials. Inter alia the following compounds are described:

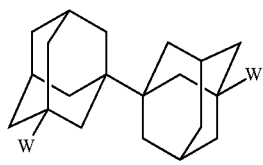

wherein W is hydroxycarbonyl, methoxycarbonyl, ethoxycarbonyl, n-propoxycarbonyl, i-propoxycarbonyl, n-butoxycarbonyl, i-butoxycarbonyl, (1-methyl-propyl-1-oxy)-carbonyl, t-butoxycarbonyl, n-pentoxycarbonyl, (3-methyl-butyl-1-oxy)-carbonyl, n-hexyloxycarbonyl, n-heptyloxycarbonyl, n-octyloxycarbonyl.

In the JP 2007-140188 positive working-light compositions and a pattern-forming method are described. Inter alia the following compound is mentioned:

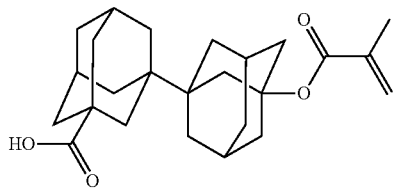

In the JP 2006265224 derivatives of the general formula

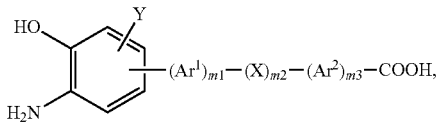

wherein $Ar^1$, $Ar^2$, m1, m2, m3, and Y are as defined therein, are described as starting compounds for the preparation of low dielectric-constant resins. Inter alia the following diadamantyl compounds are explicitly described:

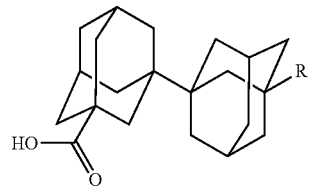

R=Br, 4-hydroxyphenyl, 4-hydroxy-3-nitrophenyl, 3-amino-4-hydroxyphenyl, 4-(3-benzyloxy-4-nitrophenoxy)-phenyl, 4-(4-amino-3-hydroxy-phenoxy) phenyl The inventors are not aware that 1,1'-diadamantyl carboxylic acids have been described as inhibitors of 11β-hydroxysteroid dehydrogenase (HSD) 1.

AIM OF THE INVENTION

The aim of the present invention is to find new 1,1'-diadamantyl carboxylic acids, particularly those which are active with regard to the enzyme 11β-hydroxysteroid dehydrogenase (HSD) 1. A further aim of the present invention is to discover 1,1'-diadamantyl carboxylic acids which have an inhibitory effect on the enzyme 11β-hydroxysteroid dehydrogenase (HSD) 1 in vitro and/or in vivo and possess suitable pharmacological and pharmacokinetic properties to use them as medicaments. A further aim of the present invention is to provide new pharmaceutical compositions which are suitable for the prevention and/or treatment of metabolic disorders, particularly diabetes, obesity, and dyslipidemia.

Other aims of the present invention will become apparent to the skilled man directly from the foregoing and following remarks.

OBJECT OF THE INVENTION

In a first aspect the present invention relates to a compound of the formula (I)

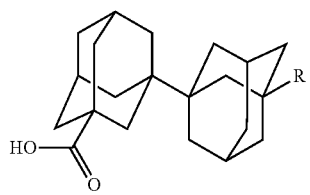

wherein
R denotes hydrogen, halogen, $C_{1-10}$-alkyl, $C_{2-6}$-alkenyl, $C_{2-6}$-alkynyl, $C_{3-6}$-cycloalkyl, hydroxy, cyano, amino, pyrrolidin-1-yl, piperidin-1-yl, nitro, sulfanyl, (het)aryl, aminocarbonyl, cyanoaminocarbonyl, azetidin-1-ylcarbonyl, pyrrolidin-1-ylcarbonyl, piperidin-1-ylcarbonyl, or morpholin-4-ylcarbonyl, wherein each alkyl, cycloalkyl, cycloheteroalkyl, alkenyl, and alkynyl group is optionally mono- or polysubstituted independently of each other with fluorine, $C_{1-4}$-alkyl, $C_{3-6}$-cycloalkyl, hydroxy, $C_{1-4}$-alkoxy, (het)aryloxy, $C_{1-4}$-alkylsulfanyl, $C_{1-4}$-alkylsulfinyl, $C_{1-4}$-alkylsulfonyl, amino, $C_{1-4}$-alkylamino, di-($C_{1-4}$-alkyl)amino, N—$C_{1-3}$-alkoxy-N—$C_{1-3}$-alkyl-amino, azetidin-1-yl, pyrrolidin-1-yl, piperidin-1-yl, $C_{1-4}$-alkylcarbonylamino, N—($C_{1-4}$-alkylcarbonyl)-N—$C_{1-3}$-alkyl-amino, (het)aryl-carbonylamino, N-[(het)arylcarbonyl]-N—$C_{1-3}$-alkyl-amino, cyano, carboxy, $C_{1-4}$-alkoxycarbonyl, aminocarbonyl, $C_{1-4}$-alkylaminocarbonyl, di-($C_{1-4}$-alkyl)amino-carbonyl, (het)arylaminocarbonyl, N-((het)aryl)-N—($C_{1-3}$-alkyl)-aminocarbonyl, or (het)aryl, while each alkyl, cycloalkyl, and cycloheteroalkyl group is optionally mono- or polysubstituted with fluorine and/or mono- or disubstituted independently of each other with $C_{1-3}$-alkyl, hydroxy, $C_{1-3}$-alkyloxy, cyano, carboxy, $C_{1-3}$-alkyloxycarbonyl, aminocarbonyl, methylaminocarbonyl, dimethylaminocarbonyl, amino, acetylamino, or (het)aryl, wherein in each above-mentioned alkyl, cycloalkyl, cycloheteroalkyl, alkenyl, and alkynyl group optionally one to three $CH_2$ groups are replaced independently of each other by $NR^N$, O, S, SO, $SO_2$, and CO, while if one of these groups happens to be incorporated more than once they are not directly attached to each other, $R^N$ denotes hydrogen, $C_{1-6}$-alkyl, $C_{3-6}$-alkenyl, $C_{3-6}$-alkynyl, $C_{3-6}$-cycloalkyl, (het)aryl, $C_{1-4}$-alkylcarbonyl, $C_{1-4}$-alkyloxycarbonyl, aminocarbonyl, $C_{1-4}$-alkylaminocarbonyl, di-($C_{1-3}$-alkyl)amino-carbonyl, $C_{1-4}$-alkylsulfonyl, (het)arylcarbonyl, (het)arylaminocarbonyl, or (het)arylsulfonyl, wherein each alkyl, cycloalkyl, alkenyl, and alkynyl group is optionally mono- or polysubstituted with fluorine and optionally monosubstituted with hydroxy, $C_{1-4}$-alkoxy, $C_{1-4}$-alkylsulfanyl, $C_{1-4}$-alkylsulfinyl, $C_{1-4}$-alkylsulfonyl, amino, $C_{1-4}$-alkylamino, di-($C_{1-4}$-alkyl)amino, $C_{1-4}$-alkylcarbonylamino, cyano, carboxy, $C_{1-4}$-alkoxycarbonyl, aminocarbonyl, $C_{1-4}$-alkylaminocarbonyl, di-($C_{1-4}$-alkyl)aminocarbonyl, or (het)aryl, (het)aryl is selected from the group consisting of phenyl, naphthyl, pyrrolyl, furanyl, thienyl, tetrazolyl, pyridyl, indolyl, benzofuranyl, benzothiophenyl, quinolinyl, and isoquinolinyl, or selected from the group consisting of pyrrolyl, furanyl, thienyl, and pyridyl in all of which 1 or 2 CH-groups are replaced by N, or selected from the group consisting of indolyl, benzofuranyl, benzothiophenyl, quinolinyl, and isoquinolinyl, in all of which 1 to 3 CH-groups are replaced by N, or selected from the group consisting of 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzo-furanyl, 2,3-dihydro-2-oxo-1H-benzimidazolyl, 2,3-dihydro-2-oxo-benzoxazolyl, 1,2-di-hydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 1,4-dihydro-4-oxo-quina-zolinyl, 1,2,3,4-tetrahydro-2,4-dioxo-quinazolinyl, 1,2-dihydro-2-oxoquinoxalinyl, 1,2,3,4-tetrahydro-3-oxo-quinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, coumarinyl, 2,3-dihydro-benzo[1,4]dioxinyl, and 3,4-dihydro-3-oxo-2H-benzo[1,4]oxazinyl, dihydroquinazolinyl, 3,4-dihydro-1H-isoquinolin-2-yl-carbonyl, 1,3-dihydro-isoindol-2-yl-carbonyl, 2,3-dihydro-indol-1-yl-carbonyl, and 1,2,4,5-tetrahydro-benzo[d]azepin-3-yl-carbonyl, wherein the above-mentioned (het)aryl rings are optionally mono- or polyfluorinated and are optionally substituted with 1, 2, 3, or 4 substituents selected independently of each other from $L^1$, $L^1$ denotes halogen, $C_{1-3}$-alkyl, difluoromethyl, trifluoromethyl, cyano, nitro, amino, $C_{1-3}$-alkylamino, di-($C_{1-3}$-alkyl)amino, $C_{1-3}$-alkylcarbonylamino, $C_{1-3}$-alkylsulfonylamino, carboxy, $C_{1-4}$-alkyloxycarbonyl, aminocarbonyl, $C_{1-3}$-alkylaminocarbonyl, di-($C_{1-3}$-alkyl)-aminocarbonyl, aminosulfonyl, $C_{1-3}$-alkylsulfanyl, $C_{1-3}$-alkylsulfinyl, $C_{1-3}$-alkylsulfonyl, hydroxy, $C_{1-3}$-alkyloxy, difluoromethoxy, trifluoromethoxy, phenethyl, phenoxy, or phenyl, while all before mentioned phenyl groups are optionally substituted with 1 or 2 substituents independently of each other selected from fluorine, methyl, methoxy, cyano, carboxy, dimethylaminocarbonyl, or hydroxy, whilst each of the above-mentioned alkyl or alkylene moieties may be branched or unbranched, a tautomer, a stereoisomer thereof, a mixture thereof, or a salt thereof, or a prodrug thereof, with the proviso (P1) that the compounds of the general formula (I) wherein R is hydroxycarbonyl, (2-methyl-1-oxo-2-propenyl-1-yl)oxy-, bromo, 4-hydroxyphenyl, 4-hydroxy-3-nitrophenyl, 3-amino-4-hydroxyphenyl, 4-(3-benzyloxy-4-nitro-phenoxy)-phenyl, or 4-(4-amino-3-hydroxy-phenoxy)-phenyl are excluded, and with the proviso (P2) that the compounds of the general formula (X)

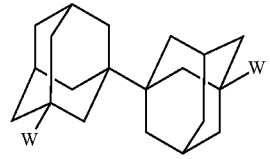

wherein W is methoxycarbonyl, ethoxycarbonyl, n-propoxycarbonyl, i-propoxycarbonyl, n-butyloxycarbonyl, i-butyloxycarbonyl, (1-methyl-propyl-1-oxy)-carbonyl, t-butyloxycarbonyl, n-pentaloxycarbonyl, (3-methyl-butyl-1-oxy)-carbonyl, n-hexyloxycarbonyl, n-heptyloxycarbonyl, or n-octyloxycarbonyl, are excluded.

The compounds of general formula I according to the invention, including those compounds comprised by the proviso (P1), and the physiologically acceptable salts thereof have valuable pharmacological properties, particularly an inhibitory effect on the enzyme 11β-hydroxysteroid dehydrogenase (HSD) 1.

A further aspect of the invention relates to the physiologically acceptable salts of the compounds of general formula I according to this invention with inorganic or organic acids.

In a further aspect this invention relates to pharmaceutical compositions, containing at least one compound of general formula I, including those compounds comprised by the provisos (P1) and (P2), or a physiologically acceptable salt according to the invention, optionally together with one or more inert carriers and/or diluents.

In a further aspect this invention relates to the compounds according to general formula I, including those compounds comprised by the provisos (P1) and (P2), or the physiologically acceptable salts thereof, for treatment or prevention of diseases or conditions which can be influenced by inhibiting the enzyme 11β-hydroxysteroid dehydrogenase (HSD) 1, such as metabolic disorders.

In a further aspect this invention relates to the use of at least one compound according to general formula I, including those compounds comprised by the provisos (P1) and (P2), or one of the physiologically acceptable salts thereof for preparing a pharmaceutical composition which is suitable for the treatment or prevention of diseases or conditions which can be influenced by inhibiting the enzyme 11β-hydroxysteroid dehydrogenase (HSD) 1, such as metabolic disorders.

In a further aspect the present invention relates to a process for preparing a compound of general formula I, characterized in that in order to prepare a compound of general formula I which are defined as hereinbefore and hereinafter, a carboxylic acid ester of the general formula II

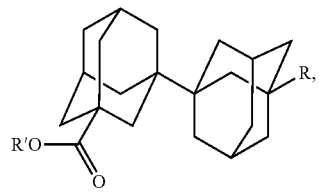

wherein
the group R is defined as hereinbefore and hereinafter, and R' is $C_{1-6}$-alkyl, $C_{3-6}$-cycloalkyl-$C_{1-3}$-alkyl, $C_{3-6}$-cycloalkyl, $C_{2-6}$-alkenyl, $C_{3-6}$-alkynyl, aryl-$C_{1-3}$-alkyl, aryl, while the alkyl, cycloalkyl, alkenyl, and alkynyl groups mentioned in the definition of the above groups, either alone or as part of another group, optionally are mono- or polysubstituted with fluorine, chlorine, $C_{1-3}$-alkyl, or $C_{1-3}$-alkoxy, and the aryl group mentioned in the definition above is phenyl or naphthyl each optionally independently of each other mono- or polysubstituted with fluorine, chlorine, bromine, $C_{1-3}$-alkyl, $C_{1-3}$-alkyloxy, nitro, cyano, or di-($C_{1-3}$-alkyl)amino, is hydrolyzed with e.g. an inorganic base such as lithium, sodium, potassium, calcium, or barium hydroxide optionally in the presence of a transfer catalyst in solvents or mixture of solvents that are preferably selected from tetrahydrofuran, 1,2-dimethoxyethane, ether, 1,4-dioxane, dichloromethane, dimethylsulfoxide, N,N-dimethylformamide, N,N-dimethylacetamide, N-methylpyrrolidinone, acetonitrile, acetone, methanol, ethanol, isopropanol, butanol, and water, preferably at temperatures between −10 and 120° C.;

and, if necessary any protective group used in the reactions described above is cleaved concurrently or subsequently;

if desired a compound of general formula I thus obtained is resolved into its stereoisomers;

if desired a compound of general formula I thus obtained is converted into a prodrug thereof;

if desired a compound of general formula I thus obtained is converted into a salt thereof, particularly for pharmaceutical use into a physiologically acceptable salt thereof.

DETAILED DESCRIPTION OF THE INVENTION

Unless otherwise stated, the groups, residues, and substituents, particularly R, are defined as above and hereinafter. If residues, substituents, or groups occur several times in a compound they may have the same or different meanings. Some preferred meanings of individual groups and substituents of the compounds according to the invention will be given hereinafter.

According to this invention compounds of formula (I)

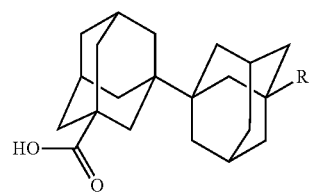

are preferred wherein

R denotes hydrogen, halogen, $C_{1-10}$-alkyl, $C_{2-6}$-alkenyl, $C_{2-6}$-alkynyl, $C_{3-6}$-cycloalkyl, hydroxy, cyano, amino, pyrrolidin-1-yl, piperidin-1-yl, nitro, sulfanyl, (het)aryl, aminocarbonyl, cyanoaminocarbonyl, azetidin-1-ylcarbonyl, pyrrolidin-1-ylcarbonyl, piperidin-1-ylcarbonyl, or morpholin-4-ylcarbonyl, wherein each alkyl, cycloalkyl, cycloheteroalkyl, alkenyl, and alkynyl group is optionally mono- or polysubstituted independently of each other with fluorine, $C_{1-4}$-alkyl, $C_{3-6}$-cycloalkyl, hydroxy, $C_{1-4}$-alkoxy, (het)aryloxy, $C_{1-4}$-alkylsulfanyl, $C_{1-4}$-alkylsulfinyl, $C_{1-4}$-alkylsulfonyl, amino, $C_{1-4}$-alkylamino, di-($C_{1-4}$-alkyl)amino, N—$C_{1-3}$-alkoxy-N—$C_{1-3}$-alkyl-amino, azetidin-1-yl, pyrrolidin-1-yl, piperidin-1-yl, $C_{1-4}$-alkylcarbonylamino, N—($C_{1-4}$-alkylcarbonyl)-N—$C_{1-3}$-alkyl-amino, (het)arylcarbonylamino, N-[(het)arylcarbonyl]-N—$C_{1-3}$-alkyl-amino, cyano, carboxy, $C_{1-4}$-alkoxycarbonyl, aminocarbonyl, $C_{1-4}$-alkylaminocarbonyl, di-($C_{1-4}$-alkyl)aminocarbonyl, (het)arylaminocarbonyl, N-((het)aryl)-N—($C_{1-3}$-alkyl)-aminocarbonyl, or (het)aryl, while each alkyl, cycloalkyl, and cycloheteroalkyl group is optionally mono- or polysubstituted with fluorine and/or mono- or disubstituted independently of each other with $C_{1-3}$-alkyl, hydroxy, $C_{1-3}$-alkyloxy, cyano, carboxy, $C_{1-3}$-alkyloxycarbonyl, aminocarbonyl, methylaminocarbonyl, dimethylaminocarbonyl, amino, acetylamino, or (het)aryl, wherein in each above-mentioned alkyl, cycloalkyl, cycloheteroalkyl, alkenyl, and alkynyl group optionally one to three $CH_2$ groups are replaced independently of each other by $NR^N$, O, S, SO, $SO_2$, and CO, while if one of these groups happens to be incorporated more than once they are not directly attached to each other, $R^N$ denotes hydrogen, $C_{1-6}$-alkyl, $C_{3-6}$-alkenyl, $C_{3-6}$-alkynyl, $C_{3-6}$-cycloalkyl, (het)aryl, $C_{1-4}$-alkylcarbonyl, $C_{1-4}$-alkyloxycarbonyl, $C_{1-4}$-alkylaminocarbonyl, di-($C_{1-3}$-alkyl) amino-carbonyl, $C_{1-4}$-alkylsulfonyl, (het)arylcarbonyl, (het)arylaminocarbonyl, or (het)arylsulfonyl, wherein each alkyl, cycloalkyl, alkenyl, and alkynyl group is optionally mono- or polysubstituted with fluorine and optionally monosubstituted with hydroxy, C$_{1-4}$-alkoxy, C$_{1-4}$-alkylsulfanyl, C$_{1-4}$-alkylsulfinyl, C$_{1-4}$-alkylsulfonyl, amino, C$_{1-4}$-alkylamino, di-(C$_{1-4}$-alkyl)amino, C$_{1-4}$-alkylcarbonylamino, cyano, carboxy, C$_{1-4}$-alkoxycarbonyl, aminocarbonyl, C$_{1-4}$-alkylaminocarbonyl, di-(C$_{1-4}$-alkyl)aminocarbonyl, or (het)aryl, (het)aryl is selected from the group consisting of phenyl, naphthyl, pyrrolyl, furanyl, thienyl, tetrazolyl, pyridyl, indolyl, benzofuranyl, benzothiophenyl, quinolinyl, and isoquinolinyl, or selected from the group consisting of pyrrolyl, furanyl, thienyl, and pyridyl in all of which 1 or 2 CH-groups are replaced by N, or selected from the group consisting of indolyl, benzofuranyl, benzothiophenyl, quinolinyl, and isoquinolinyl, in all of which 1 to 3 CH-groups are replaced by N, or selected from the group consisting of 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzo-furanyl, 2,3-dihydro-2-oxo-1H-benzimidazolyl, 2,3-dihydro-2-oxo-benzoxazolyl, 1,2-di-hydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 1,4-dihydro-4-oxo-quina-zolinyl, 1,2,3,4-tetrahydro-2,4-dioxo-quinazolinyl, 1,2-dihydro-2-oxoquinoxalinyl, 1,2,3,4-tetrahydro-3-oxo-quinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, coumarinyl, 2,3-dihydro-benzo[1,4]dioxinyl, and 3,4-dihydro-3-oxo-2H-benzo[1,4]oxazinyl, wherein the above-mentioned (het)aryl rings are optionally mono- or polyfluorinated and are optionally substituted with 1, 2, 3, or 4 substituents selected independently of each other from L$^1$, L$^1$ denotes halogen, C$_{1-3}$-alkyl, difluoromethyl, trifluoromethyl, cyano, nitro, amino, C$_{1-3}$-alkylamino, di-(C$_{1-3}$-alkyl)amino, C$_{1-3}$-alkylcarbonylamino, C$_{1-3}$-alkylsulfonylamino, carboxy, C$_{1-4}$-alkyloxycarbonyl, aminocarbonyl, C$_{1-3}$-alkylaminocarbonyl, di-(C$_{1-3}$-alkyl)-aminocarbonyl, aminosulfonyl, C$_{1-3}$-alkylsulfanyl, C$_{1-3}$-alkylsulfinyl, C$_{1-3}$-alkylsulfonyl, hydroxy, C$_{1-3}$-alkyloxy, difluoromethoxy, trifluoromethoxy, or phenyl optionally substituted with 1 or 2 substituents independently of each other selected from fluorine, methyl, methoxy, cyano, or hydroxy, whilst each of the above-mentioned alkyl or alkylene moieties may be branched or unbranched, a tautomer, a stereoisomer thereof, a mixture thereof, or a salt thereof, or a prodrug thereof, with the proviso (P1) that the compounds of the general formula (I) wherein R is hydroxycarbonyl, (2-methyl-1-oxo-2-propenyl-1-yl)oxy-, bromo, 4-hydroxyphenyl, 4-hydroxy-3-nitrophenyl, 3-amino-4-hydroxyphenyl, 4-(3-benzyloxy-4-nitro-phenoxy)-phenyl, or 4-(4-amino-3-hydroxy-phenoxy)-phenyl are excluded, and with the proviso (P2) that the compounds of the general formula (X)

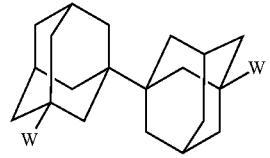

wherein W is methoxycarbonyl, ethoxycarbonyl, n-propoxycarbonyl, i-propoxycarbonyl, n-butyloxycarbonyl, i-butyloxycarbonyl, (1-methyl-propyl-1-oxy)-carbonyl, t-butyloxycarbonyl, n-pentaloxycarbonyl, (3-methyl-butyl-1-oxy)-carbonyl, n-hexyloxycarbonyl, n-heptyloxycarbonyl, or n-octyloxycarbonyl, are excluded.

According to the embodiment (E1a) the group R preferably denotes C$_{1-6}$-alkyl which is optionally mono- or polysubstituted with fluorine and optionally substituted with 1, 2, 3 or 4 substituents independently of each other selected from the group consisting of hydroxy, C$_{1-4}$-alkoxy, (het)aryloxy, C$_{1-4}$-alkylsulfinyl, C$_{5-6}$-cycloalkyl, tetrahydrofuranyl, tetrahydropyranyl, 4-(het)aryl-piperazin-1-yl, 4-C$_{1-4}$-alkylcarbonyl-piperazin-1-yl, 4-C$_{1-4}$-alkylsulfonyl-piperazin-1-yl, morpholin-4-yl, C$_{1-4}$-alkylcarbonylamino, (het)aryl-carbonylamino, pyrrolidin-2-on-1-yl, piperidin-2-on-1-yl, piperazin-2-on-1-yl, piperazin-3-on-1-yl, morpholin-3-on-4-yl, morpholin-2-on-4-yl, cyano, carboxy, C$_{1-4}$-alkyloxycarbonyl, aminocarbonyl, C$_{1-4}$-alkylaminocarbonyl, di-(C$_{1-4}$-alkyl)aminocarbonyl, (het)aryl-aminocarbonyl, N-(het)aryl-N—(C$_{1-3}$-alkyl)aminocarbonyl and (het)aryl, while each alkyl-residue in the herein before mentioned substituents is optionally mono- or polysubstituted with fluoro and/or monosubstituted with hydroxy, C$_{1-3}$-alkoxy or cyano; and while each herein before mentioned cycloalkyl or cycloheteroalkyl group is optionally mono- or disubstituted independently of each other with C$_{1-3}$-alkyl, fluorine, hydroxy, C$_{1-3}$-alkyloxy, cyano, carboxy, C$_{1-3}$-alkyloxycarbonyl, aminocarbonyl, methylaminocarbonyl, dimethylaminocarbonyl, amino, acetylamino, or (het)aryl.

According to a more preferred embodiment (E1b) the group R preferably denotes C$_{1-6}$-alkyl which is optionally mono- or polysubstituted with fluorine and optionally substituted with 1, 2, or 3 substituents independently of each other selected from the group consisting of hydroxy, C$_{1-4}$-alkoxy, phenyloxy, pyridinyloxy, C$_{1-4}$-alkylsulfinyl, C$_{5-6}$-cycloalkyl, tetrahydrofuranyl, tetrahydropyranyl, 4-phenyl-piperazin-1-yl, 4-C$_{1-4}$-alkylcarbonyl-piperazin-1-yl, 4-C$_{1-4}$-alkylsulfonyl-piperazin-1-yl, morpholin-4-yl, C$_{1-4}$-alkylcarbonylamino, phenylcarbonylamino, pyrrolidin-2-on-1-yl, piperidin-2-on-1-yl, piperazin-2-on-1-yl, piperazin-3-on-1-yl, morpholin-3-on-4-yl, morpholin-2-on-4-yl, cyano, carboxy, C$_{1-4}$-alkyloxycarbonyl, aminocarbonyl, C$_{1-4}$-alkylaminocarbonyl, di-(C$_{1-4}$-alkyl)aminocarbonyl, phenylaminocarbonyl, N-phenyl-N—(C$_{1-3}$-alkyl)-aminocarbonyl, and phenyl; while each alkyl-residue is optionally mono- or polysubstituted with fluorine and/or monosubstituted with hydroxy, C$_{1-3}$-alkoxy or cyano; and while each phenyl ring is optionally mono- or disubstituted independently of each other with fluorine, cyano, C$_{1-3}$-alkyl, trifluoromethyl, hydroxy, methoxy, methylamino, dimethylamino, acetylamino, methylsulfonylamino, carboxy, aminocarbonyl, methylaminocarbonyl and dimethylaminocarbonyl.

According to an even more preferred embodiment (E1c) the group R preferably denotes hydroxy-C$_{1-3}$-alkyl or pyridyloxy-C$_{1-3}$-alkyl. Examples are hydroxymethyl, 2-hydroxyprop-2-yl and pyrid-2-yloxymethyl.

According to the embodiment (E2a) the group R preferably denotes $C_{5-6}$-cycloalkyl, tetrahydrofuranyl, tetrahydrofuranonyl, tetrahydropyranyl, tetrahydropyranonyl, pyrrolidinonyl, piperidinonyl, piperazinonyl, 4-($C_{1-3}$-alkyl)-piperazinonyl or morpholinonyl, while each herein before mentioned cycloalkyl or cycloheteroalkyl group is optionally mono- or disubstituted independently of each other with $C_{1-3}$-alkyl, fluorine, hydroxy, $C_{1-3}$-alkyloxy, cyano, carboxy, $C_{1-3}$-alkyloxycarbonyl, aminocarbonyl, methylaminocarbonyl, dimethylaminocarbonyl, amino, acetylamino, or (het)aryl.

According to a more preferred embodiment (E2b) the group R preferably denotes $C_{5-6}$-cycloalkyl, tetrahydrofuranyl, tetrahydrofuran-2-onyl, tetrahydropyranyl, tetrahydropyran-2-onyl, pyrrolidin-2-onyl, piperidin-2-onyl, piperazin-2-onyl, 4-($C_{1-3}$-alkyl)piperazin-2-onyl, morpholin-2-onyl, or morpholin-3-onyl, which are optionally mono- or disubstituted independently of each other with methyl, fluorine, hydroxy, methoxy, and phenyl, while each phenyl ring is optionally mono- or disubstituted independently of each other with fluorine, cyano, $C_{1-3}$-alkyl, trifluoromethyl, hydroxy, methoxy, methylamino, dimethylamino, acetylamino, methylsulfonylamino, carboxy, aminocarbonyl, methylaminocarbonyl or dimethylaminocarbonyl.

According to the embodiment (E3a) the group R preferably denotes hydroxy, (het)aryloxy, $C_{1-4}$-alkyloxy, (het)aryl-$C_{1-3}$-alkyloxy, cyano-$C_{1-3}$-alkyloxy, carboxy-$C_{1-3}$-alkyloxy, $C_{1-4}$-alkyloxy-carbonyl-$C_{1-3}$-alkyloxy, aminocarbonyl-$C_{1-3}$-alkyloxy, $C_{1-4}$-alkylaminocarbonyl-$C_{1-3}$-alkyloxy, di-($C_{1-4}$-alkyl)aminocarbonyl-$C_{1-3}$-alkyloxy, (het)arylaminocarbonyl-$C_{1-3}$-alkyloxy, (het)aryl-$C_{1-3}$-alkyl-aminocarbonyl-$C_{1-3}$-alkyloxy, N-(het)aryl-N—($C_{1-3}$-alkyl)-aminocarbonyl-$C_{1-3}$-alkyloxy, N-((het)aryl-$C_{1-3}$-alkyl)-N—($C_{1-3}$-alkyl)-aminocarbonyl-$C_{1-3}$-alkyloxy, pyrrolidin-1-ylcarbonyl-$C_{1-3}$-alkyloxy, piperidin-1-ylcarbonyl-$C_{1-3}$-alkyloxy, piperazin-1-yl-$C_{1-3}$-alkyloxy, 4-($C_{1-4}$-alkyl)-piperazin-1-ylcarbonyl-$C_{1-3}$-alkyloxy, 4-(het)aryl-piperazin-1-ylcarbonyl-$C_{1-3}$-alkyloxy, morpholin-4-ylcarbonyl-$C_{1-3}$-alkyloxy, while each alkyl-residue is optionally mono- or polysubstituted with fluorine and/or monosubstituted with hydroxy, $C_{1-3}$-alkoxy or cyano; and while each herein before mentioned cycloheteroalkyl group is optionally mono- or disubstituted independently of each other with $C_{1-3}$-alkyl, fluorine, hydroxy, $C_{1-3}$-alkyloxy, cyano, carboxy, $C_{1-3}$-alkyloxycarbonyl, aminocarbonyl, methylaminocarbonyl, dimethylaminocarbonyl, amino, acetylamino, or (het)aryl.

According to a more preferred embodiment (E3b) the group R preferably denotes hydroxy, phenoxy, $C_{1-4}$-alkyloxy, phenyl-$C_{1-3}$-alkyloxy, cyano-$C_{1-3}$-alkyloxy, carboxy-$C_{1-3}$-alkyloxy, $C_{1-4}$-alkyloxycarbonyl-$C_{1-3}$-alkyloxy, aminocarbonyl-$C_{1-3}$-alkyloxy, $C_{1-4}$-alkylamino-carbonyl-$C_{1-3}$-alkyloxy, di-($C_{1-4}$-alkyl)aminocarbonyl-$C_{1-3}$-alkyloxy, phenylamino-carbonyl-$C_{1-3}$-alkyloxy, phenyl-$C_{1-3}$-alkyl-aminocarbonyl-$C_{1-3}$-alkyloxy, N-phenyl-N—($C_{1-3}$-alkyl)-amino-carbonyl-$C_{1-3}$-alkyloxy, N-(phenyl-$C_{1-3}$-alkyl)-N—($C_{1-3}$-alkyl)-aminocarbonyl-$C_{1-3}$-alkyloxy, pyrrolidin-1-ylcarbonyl-$C_{1-3}$-alkyloxy, piperidin-1-ylcarbonyl-$C_{1-3}$-alkyloxy, piperazin-1-yl-$C_{1-3}$-alkyloxy, 4-($C_{1-4}$-alkyl)-piperazin-1-ylcarbonyl-$C_{1-3}$-alkyloxy, 4-phenyl-piperazin-1-ylcarbonyl-$C_{1-3}$-alkyloxy, or morpholin-4-ylcarbonyl-$C_{1-3}$-alkyloxy; while each alkyl-residue is optionally mono- or polysubstituted with fluorine and/or monosubstituted with hydroxy, $C_{1-3}$-alkoxy or cyano; and while each phenyl-ring is optionally mono- or disubstituted independently of each other with fluorine, cyano, $C_{1-3}$-alkyl, trifluoromethyl, hydroxy, methoxy, methylamino, dimethylamino, acetylamino, methylsulfonylamino, carboxy, aminocarbonyl, methylamino-carbonyl, or dimethylaminocarbonyl.

According to the embodiment (E4a) the group R preferably denotes amino, $C_{1-4}$-alkylcarbonylamino, (het)aryl-carbonylamino, (het)aryl-$C_{1-3}$-alkyl-carbonylamino, $C_{1-4}$-alkyloxycarbonylamino, pyrrolidin-1-yl, piperidin-1-yl, piperazin-1-yl, 4-(het)aryl-piperazin-1-yl, 4-$C_{1-4}$-alkylcarbonyl-piperazin-1-yl, 4-(het)aryl-carbonyl-piperazin-1-yl, 4-$C_{1-4}$-alkylsulfonyl-piperazin-1-yl, or morpholin-4-yl; while each alkyl-residue is optionally mono- or polysubstituted with fluorine and/or monosubstituted with hydroxy, $C_{1-3}$-alkoxy or cyano; and while each herein before mentioned cycloheteroalkyl group is optionally mono- or disubstituted independently of each other with $C_{1-3}$-alkyl, fluorine, hydroxy, $C_{1-3}$-alkyloxy, cyano, carboxy, $C_{1-3}$-alkyloxycarbonyl, aminocarbonyl, methylaminocarbonyl, dimethylaminocarbonyl, amino, acetylamino, or (het)aryl.

According to a more preferred embodiment (E4b) the group R preferably denotes amino, $C_{1-4}$-alkylcarbonylamino, phenylcarbonylamino, phenyl-$C_{1-3}$-alkyl-carbonylamino, $C_{1-4}$-alkyloxy-carbonylamino, pyrrolidin-1-yl, piperidin-1-yl, piperazin-1-yl, 4-phenyl-piperazin-1-yl, 4-$C_{1-4}$-alkylcarbonyl-piperazin-1-yl, 4-phenylcarbonyl-piperazin-1-yl, 4-$C_{1-4}$-alkylsulfonyl-piperazin-1-yl, or morpholin-4-yl; while each alkyl-residue is optionally mono- or polysubstituted with fluorine and/or monosubstituted with hydroxy, $C_{1-3}$-alkoxy or cyano; and while each phenyl-ring is optionally mono- or disubstituted independently of each other with fluorine, cyano, $C_{1-3}$-alkyl, trifluoromethyl, hydroxy, methoxy, methylamino, dimethylamino, acetylamino, methylsulfonylamino, carboxy, aminocarbonyl, methylaminocarbonyl, or dimethylaminocarbonyl.

According to an even more preferred embodiment (E4c) the group R preferably denotes amino, $C_{1-3}$-alkylcarbonyl-amino or $C_{1-4}$-alkyloxycarbonyl-amino. Examples are amino, acetylamino, tert-butoxycarbonylamino.

According to the embodiment (E5a) the group R preferably denotes cyano, $C_{1-4}$-alkyloxycarbonyl, (het)aryl-carbonyl, aminocarbonyl, $C_{1-4}$-alkylaminocarbonyl, di-($C_{1-4}$-alkyl)aminocarbonyl, N—($C_{5-6}$-cycloalkyl)-N—($C_{1-3}$-alkyl)aminocarbonyl, N—($C_{5-6}$-cycloheteroalkyl)-N—($C_{1-3}$-alkyl)-aminocarbonyl, (het)arylaminocarbonyl, (het)aryl-$C_{1-3}$-alkyl-aminocarbonyl, N-(het)aryl-N—($C_{1-3}$-alkyl)aminocarbonyl, N-((het)aryl-$C_{1-3}$-alkyl)-N—($C_{1-3}$-alkyl)-aminocarbonyl, N-((het)aryl-$C_{1-3}$-alkyl)-N—($C_{5-6}$-cycloalkyl)-aminocarbonyl, azetidin-1-ylcarbonyl, pyrrolidin-1-ylcarbonyl, piperidin-1-ylcarbonyl, piperazin-1-ylcarbonyl, morpholin-4-ylcarbonyl, methoxy-aminocarbonyl, or cyanoamino-carbonyl; while each alkyl-residue is optionally mono- or polysubstituted with fluorine and/or monosubstituted with hydroxy, $C_{1-3}$-alkoxy or cyano; and while each herein before mentioned cycloalkyl and cycloheteroalkyl group is optionally mono- or disubstituted independently of each other with $C_{1-4}$-alkyl, fluorine, hydroxy, $C_{1-3}$-alkyloxy, cyano, carboxy, $C_{1-3}$-alkyloxycarbonyl, aminocarbonyl, methylaminocarbonyl, dimethylaminocarbonyl, amino, acetylamino, or (het)aryl.

According to a more preferred embodiment (E5b) the group R preferably denotes cyano, $C_{1-4}$-alkyloxycarbonyl, phenylcarbonyl, aminocarbonyl, $C_{1-4}$-alkylaminocarbonyl, di-($C_{1-4}$-alkyl)aminocarbonyl, phenylaminocarbonyl, phenyl-$C_{1-3}$-alkyl-aminocarbonyl, N-phenyl-N—($C_{1-3}$-alkyl)-aminocarbonyl, N-(phenyl-$C_{1-3}$-alkyl)-N—($C_{1-3}$-alkyl)aminocarbonyl, N—($C_{1-3}$-alkyl)-N—($C_{5-6}$-cycloalkyl)-aminocarbonyl, N—($C_{1-3}$-alkyl)-N—($C_{5-6}$-cycloheteroalkyl)amino-carbonyl, N—($C_{5-6}$-cycloalkyl)-N-(phenyl-$C_{1-3}$-alkyl)-aminocarbonyl, azetidin-1-ylcarbonyl, pyrrolidin-1-ylcarbonyl, piperidin-1-ylcarbonyl, piperazin-1-ylcarbonyl, morpholin-4-ylcarbonyl, methoxy-aminocarbonyl, cyanoamino-carbonyl, 3,4-dihydro-1H-isoquinolin-2-yl-carbonyl, 1,3-dihydro-isoindol-2-yl-carbonyl, 2,3-dihydro-indol-1-yl-carbonyl, or 1,2,4,5-tetrahydro-benzo[d]azepin-3-yl-carbonyl; while each alkyl-residue is optionally mono- or polysubstituted with fluorine and/or monosubstituted with hydroxy, $C_{1-3}$-alkoxy or cyano; and while each phenyl and benzo ring is optionally mono- or disubstituted independently of each other with fluorine, chlorine, bromine, cyano, $C_{1-3}$-alkyl, trifluoromethyl, hydroxy, methoxy, methylamino, dimethylamino, acetylamino, methylsulfonylamino, carboxy, aminocarbonyl, methylaminocarbonyl, dimethylaminocarbonyl, phenyl, 4-dimethylcarbamoyl-phenoxy, or 4-carboxy-phenoxy; and while each cycloalkyl and cycloheteroalkyl group is optionally substituted with one substituent selected from $C_{1-4}$-alkyl, methoxymethyl, and phenyl.

According to an even more preferred embodiment (E5c) the group R preferably denotes cyano, $C_{1-4}$-alkyloxycarbonyl, phenylcarbonyl, aminocarbonyl, $C_{1-4}$-alkylamino-carbonyl, hydroxy-$C_{2-4}$-alkylamino-carbonyl, cyanoamino-carbonyl, methoxy-aminocarbonyl, phenylaminocarbonyl, N—($C_{1-3}$-alkyl)-N—($C_{1-4}$-alkyl)amino-carbonyl, N—($C_{1-3}$-alkyl)-N-(phenyl-$C_{1-3}$-alkyl)-aminocarbonyl, N—($C_{1-3}$-alkyl)-N—($C_{5-6}$-cycloalkyl)amino-carbonyl, N—($C_{1-3}$-alkyl)-N-piperidinyl-amino-carbonyl, N—($C_{5-6}$-cycloalkyl)-N-(phenyl-$C_{1-3}$-alkyl)aminocarbonyl, N-phenyl-N—($C_{1-3}$-alkyl)-aminocarbonyl, azetidin-1-ylcarbonyl, pyrrolidin-1-ylcarbonyl, morpholin-4-ylcarbonyl, piperazin-1-ylcarbonyl, 3,4-dihydro-1H-isoquinolin-2-ylcarbonyl, 1,3-dihydro-isoindol-2-yl-carbonyl, 2,3-dihydro-indol-1-yl-carbonyl, or 1,2,4,5-tetrahydro-benzo[d]azepin-3-yl-carbonyl, wherein each phenyl and benzo ring is optionally substituted with one or two substituents selected independently from fluorine, bromine, cyano, $C_{1-3}$-alkyl, hydroxy, methoxy, phenyl, 4-dimethylcarbamoyl-phenoxy, and 4-carboxy-phenoxy; and each cycloalkyl and cycloheteroalkyl group is optionally substituted with one substituent selected from $C_{1-4}$-alkyl, methoxymethyl, and phenyl. Examples are cyano, methoxycarbonyl, 4-methoxyphenylcarbonyl, aminocarbonyl, methylaminocarbonyl, 2-hydroxyethyl-aminocarbonyl, cyanoamino-carbonyl, methoxy-aminocarbonyl, dimethylaminocarbonyl, N-ethyl-N-methyl-aminocarbonyl, N-isopropyl-N-methyl-aminocarbonyl, N-benzyl-N-methyl-aminocarbonyl, N-phenethyl-N-methyl-aminocarbonyl, N-[3-(4-methoxyphenyl)-prop-1-yl]-N-methyl-aminocarbonyl, azetidin-1-ylcarbonyl, pyrrolidin-1-ylcarbonyl, morpholin-4-ylcarbonyl, 4-methyl-piperazin-1-ylcarbonyl, phenylaminocarbonyl, N-methyl-N-phenyl-aminocarbonyl, N-methyl-N-(4-methoxyphenyl)-aminocarbonyl, N-methyl-N-(4-phenyl-phenyl)-aminocarbonyl, N-cyclohexyl-N-methyl-aminocarbonyl, N-cyclohexyl-N-ethyl-aminocarbonyl, N-methyl-N-(4-phenyl-cyclohexyl)-aminocarbonyl, N-methyl-N-(4-tert-butyl-cyclohexyl)-aminocarbonyl, N-cyclohexyl-N-phenethyl-aminocarbonyl, N-cyclopentyl-N-methyl-aminocarbonyl, N-methyl-N-(piperidin-3-yl)-aminocarbonyl, 2-methoxymethyl-pyrrolidin-1-ylcarbonyl, 3,4-dihydro-1H-isoquinolin-2-yl-carbonyl, (7-cyano-3,4-dihydro-1H-isoquinolin-2-yl)-carbonyl, [7-(4-dimethylcarbamoyl-phenoxy)-3,4-dihydro-1H-isoquinolin-2-yl]-carbonyl, [7-(4-carboxy-phenoxy)-3,4-dihydro-1H-isoquinolin-2-yl]-carbonyl, (6-bromo-3,4-dihydro-1H-isoquinolin-2-yl)-carbonyl, 1,3-dihydro-isoindol-2-yl-carbonyl, 2,3-dihydro-indol-1-yl-carbonyl, and 1,2,4,5-tetrahydro-benzo[d]azepin-3-yl-carbonyl.

According to the embodiment (E6a) the group R preferably denotes (het)aryl.

According to a more preferred embodiment (E6b) the group R preferably denotes phenyl, furanyl, pyrazolyl, imidazolyl, oxazolyl, triazolyl, oxadiazolyl, tetrazolyl, pyridyl, pyridazinyl, pyrazinyl, pyrimidinyl, benzooxazolyl, benzoimidazolyl, quinazolinyl, or dihydroquinazolinyl, while each of the before mentioned groups is optionally mono- or disubstituted independently of each other with fluorine, cyano, $C_{1-3}$-alkyl, trifluoromethyl, hydroxy, methoxy, methylamino, dimethylamino, acetylamino, methylsulfonylamino, carboxy, aminocarbonyl, methylaminocarbonyl, dimethylaminocarbonyl, phenethyl, or phenyl.

According to an even more preferred embodiment (E6c) the group R preferably denotes oxadiazolyl, triazolyl, tetrazolyl, benzooxazolyl, benzoimidazolyl, quinazolinyl, or dihydroquinazolinyl, each of which is optionally substituted with one or two substituents selected independently from fluorine, cyano, $C_{1-3}$-alkyl, hydroxy, methoxy, phenethyl, and phenyl. Examples are phenyl-[1,3,4]oxadiazolyl, benzooxazolyl, 1-methyl-1H-benzoimidazolyl, 1-phenethyl-1H-benzoimidazolyl, quinazolinyl, dihydroquinazolinyl, and tetrazolyl.

$R^N$ preferably denotes hydrogen, $C_{1-4}$-alkyl, $C_{5-6}$-cycloalkyl, (het)aryl, $C_{1-4}$-alkylcarbonyl, $C_{1-4}$-alkyloxycarbonyl, $C_{1-4}$-alkylaminocarbonyl, di-($C_{1-3}$-alkyl)amino-carbonyl, $C_{1-4}$-alkylsulfonyl, (het)arylcarbonyl, wherein each alkyl group is optionally mono- or polysubstituted with fluorine and optionally monosubstituted with hydroxy, $C_{1-4}$-alkoxy, amino, $C_{1-3}$-alkylamino, di-($C_{1-3}$-alkyl)amino, $C_{1-4}$-alkylcarbonylamino, cyano, carboxy, $C_{1-3}$-alkoxycarbonyl, aminocarbonyl, $C_{1-3}$-alkylaminocarbonyl, di-($C_{1-3}$-alkyl)aminocarbonyl, or (het)aryl.

More preferably, $R^N$ denotes hydrogen, $C_{1-3}$-alkyl, (het)aryl, $C_{1-3}$-alkylcarbonyl, $C_{1-4}$-alkylaminocarbonyl, di-($C_{1-3}$-alkyl)amino-carbonyl, $C_{1-4}$-alkylsulfonyl, (het)arylcarbonyl, wherein each alkyl group is optionally monosubstituted with hydroxy, $C_{1-4}$-alkoxy, amino, $C_{1-3}$-alkylamino, di-($C_{1-3}$-alkyl)amino, $C_{1-4}$-alkylcarbonylamino, cyano, carboxy, $C_{1-3}$-alkoxy-carbonyl, aminocarbonyl, $C_{1-3}$-alkylaminocarbonyl, di-($C_{1-3}$-alkyl)amino-carbonyl, or (het)aryl.

Even more preferably $R^N$ denotes hydrogen, $C_{1-3}$-alkyl, hydroxy-$C_{2-3}$-alkyl, phenyl-$C_{1-3}$-alkyl, phenyl-carbonyl $C_{1-3}$-alkylcarbonyl, phenyl, or $C_{1-4}$-alkyl-sulfonyl. Examples are hydrogen, methyl, ethyl, phenyl, acetyl, methylsulfonyl.

$L^1$ preferably denotes fluorine, chlorine, $C_{1-3}$-alkyl, difluoromethyl, trifluoromethyl, cyano, $C_{1-3}$-alkylamino, di-($C_{1-3}$-alkyl)amino, acetylamino, methylsulfonylamino, carboxy, $C_{1-4}$-alkyloxycarbonyl, aminocarbonyl, $C_{1-3}$-alkylaminocarbonyl, di-($C_{1-3}$-alkyl)-aminocarbonyl, methylsulfonyl, hydroxy, $C_{1-3}$-alkyloxy, difluoromethoxy, trifluoromethoxy, or phenyl optionally substituted with 1 or 2 substituents independently of each other selected from fluorine, methyl, methoxy, cyano, or hydroxy.

More preferably, $L^1$ denotes fluorine, chlorine, methyl, trifluoromethyl, cyano, methylamino, dimethylamino, acetylamino, methylsulfonylamino, carboxy, methoxycarbonyl, aminocarbonyl, methylaminocarbonyl, dimethylaminocarbonyl, methylsulfonyl, hydroxy, methoxy, difluoromethoxy, trifluoromethoxy, or phenyl optionally substituted with 1 or 2 substituents independently of each other selected from fluorine, methyl, methoxy, cyano, or hydroxy. Most preferably, $L^1$ denotes fluorine, methyl, trifluoromethyl, cyano, acetylamino, hydroxy, and methoxy.

The term (het)aryl preferably denotes phenyl, furanyl, pyrazolyl, imidazolyl, oxazolyl, triazolyl, oxadiazolyl, tetrazolyl, pyridyl, pyridazinyl, pyrazinyl, or pyrimidinyl.

Those 1,1'-diadamantyl-3-carboxylic acid derivatives of the formulas (I) and (X) are excluded which are disclosed in the before mentioned prior art.

TERMS AND DEFINITIONS

Some terms used above and hereinafter to describe the compounds according to the invention will now be defined more closely.

The term "substituted" as used herein, means that any one or more hydrogens on the designated atom is replaced with a selection from the indicated group, provided that the designated atom's normal valence is not exceeded, and that the substitution results in a stable compound.

The term "prodrug" means a compound which is converted into a compound represented by the general formula (I) as an active form thereof in vivo. Examples of prodrugs according to this invention are compounds of the formula (I) which are esters of the 1,1'-diadamantyl-3-carboxylic acid of the formula (I), in particular $C_{1-4}$-alkyl-ester wherein the alkyl-group may be substituted with hydroxy or $C_{1-3}$-alkoxy, most preferably methyl-, ethyl, n-propyl- or i-propyl-ester.

The term halogen denotes an atom selected from the group consisting of F, Cl, Br and I.

The term $C_{1-n}$-alkyl, wherein n may have a value of 1 to 18, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term $C_{2-n}$-alkenyl, wherein n has a value of 2 to 6, denotes a branched or unbranched hydrocarbon group with 2 to n C atoms and a C=C double bond. Examples of such groups include ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl etc.

The term $C_{2-n}$-alkynyl, wherein n has a value of 2 to 6, denotes a branched or unbranched hydrocarbon group with 2 to n C atoms and a C≡C triple bond. Examples of such groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl etc. Unless otherwise stated alkynyl groups are connected to the remainder of the molecule via the C atom in position 1. Therefore terms such as 1-propynyl, 2-propynyl, 1-butynyl, etc. are equivalent to the terms 1-propyn-1-yl, 2-propyn-1-yl, 1-butyn-1-yl, etc. This also applies analogously to $C_{2-n}$-alkenyl groups.

The term $C_{1-n}$-alkoxy denotes a $C_{1-n}$-alkyl-O group, wherein $C_{1-n}$-alkyl is as hereinbefore defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy, etc.

The term $C_{1-n}$-alkylcarbonyl denotes a $C_{1-n}$-alkyl-C(=O) group, wherein $C_{1-n}$-alkyl is as hereinbefore defined. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms wherein n is 3 to 10. Examples of such groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc. Preferably the term $C_{3-7}$-cycloalkyl denotes saturated monocyclic groups.

The term $C_{5-n}$-cycloalkenyl denotes a $C_{5-n}$-cycloalkyl group which is as hereinbefore defined and additionally has at least one C=C double bond.

The term $C_{3-n}$-cycloheteroalkyl denotes a saturated mono-, bi-, tri- or spirocarbocyclic group with 3-m to n-m C atoms and wherein n denotes 3 to 10 and m denotes 1 to 3 heteroatoms independently selected from $NR^N$, O, S, SO, and $SO_2$, which in addition may have a carbonyl group. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, morpholinonyl. Preferably the term $C_{3-6}$-cycloheteroalkyl denotes saturated monocyclic groups with one or two heteroatoms.

The term $C_{3-n}$-cycloalkylcarbonyl denotes a $C_{3-n}$-cycloalkyl-C(=O) group wherein $C_{3-n}$-cycloalkyl is as hereinbefore defined.

The term tri-($C_{1-4}$-alkyl)silyl comprises silyl groups which have identical or two or three different alkyl groups.

The term di-($C_{1-3}$-alkyl)amino comprises amino groups which have identical or two different alkyl groups.

All atoms, including atoms that are part of a group, described herein comprise all stable isotopic forms of the respective element. E.g., whenever hydrogen is mentioned, either explicitly or as part of a group such as methyl, this includes hydrogen and deuterium as stable isotopic forms of the element hydrogen.

The compounds according to the invention may be obtained using methods of synthesis known in principle. Preferably, the compounds are obtained by the following methods according to the invention which are described in more detail hereinafter.

The synthesis of almost all compounds of the invention may be accomplished starting from the monocarboxylic acid shown in Scheme 1 that in turn may be obtained by selective hydrolysis of the known diester. The selective monosaponification of the diester may be achieved by treatment with a hydroxide salt such as e.g. LiOH, NaOH, KOH, Ca(OH)$_2$, Ba(OH)$_2$, in a solvent or mixture of solvents selected from 1,2-dichloromethane, toluene, benzene, acetonitrile, N,N-dimethylformamide, N,N-dimethylacetamide, N-methylpyrrolidinone, dimethylsulfoxide, 1,4-dioxane, tetrahydrofuran, 1,2-dimethoxyethane, ether, acetone, methanol, propanol, isopropanol, butanol, and water. The suited reaction temperature may depend on the base employed and is preferably in the range between 0° C. and 100° C. The stoichiometry of hydroxide salt to diester may be decisive for the outcome of the reaction; preferably, the hydroxide salt is used in substoichiometric quantity up to 10 equivalents. Additives such as hydrogen peroxide, phase-transfer-catalysts, crown ethers, or salts that promote the precipitation of the monocarboxylate from the reaction solvent may be advantageous. The conditions described are not restricted to methyl esters, other esters bearing aliphatic and/or aromatic residues that are optionally derivatized with functional groups may be employed as well. Residues that form an insoluble monoester in the reaction solvent used are particularly suited for the approach described.

Scheme 1. Selective monosaponification of a diester of diadamantane

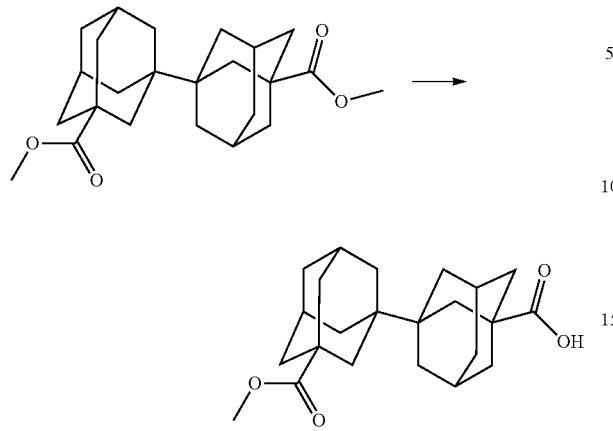

Scheme 2. Selective derivatization of the dicarboxylic acid of diadamantane

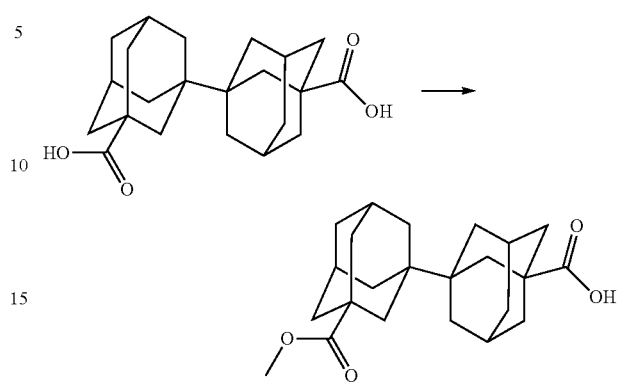

Alternatively, the desymmetrized diadamantane compound may be obtained from the dicarboxylic acid derivative which is also a known compound (Scheme 2). Here only one of the carboxy groups is to be transformed to render the monoacid. E.g., the synthesis of the monomethyl ester may be carried out using a methyl electrophile such as methyl iodide, bromide, chloride, tosylate, mesylate, trifluormethanesulfonate, or dimethylsulfate in the presence of a base such as an inorganic base, e.g. LiOH, NaOH, KOH, CsOH, $Na_2CO_3$, $K_2CO_3$, $Cs_2CO_3$, or an organic base, e.g. triethylamine, ethyldiisopropylamine, diazabicycloundecene, pyridine, 4-dimethylaminopyridine. Suited solvents are e.g. dichloromethane, toluene, benzene, acetonitrile, N,N-dimethylformamide, N,N-dimethylacetamide, N-methylpyrrolidinone, dimethylsulfoxide, 1,4-dioxane, tetrahydrofuran, 1,2-dimethoxyethane, ether, acetone, methanol, propanol, isopropanol, butanol, and water at temperatures between 0° C. and 100° C. A methyl group may also be attached via the reaction with diazomethane or a surrogate of it such as trimethylsilyldiazomethane in e.g. dichloromethane, toluene, benzene, acetonitrile, 1,4-dioxane, tetrahydrofuran, 1,2-dimethoxyethane, ether, ethyl acetate, or mixtures thereof at temperatures of 0 to 60° C. In both approaches described above the methyl electrophile is preferably used in substoichiometric amount or up to 1.5 equivalents. It is also possible to transform the dicarboxylic acid into a more reactive entity of the carboxylic function which in turn is selectively reacted with methanol at only one of the activated ester groups, the other activated ester group is hydrolyzed with water to give the desired compound. In addition to the synthesis of the methyl ester other alkyl residues may be attached analogously. Attachment of the dicarboxylic acid to a solid support such as e.g. Merrifield's resin is also possible. The reaction conditions are comparable to the conditions using an alkyl electrophile in the presence of a base described above except for the alternative technique needed for working with polymeric compounds (see e.g. Bunin, B. A., *The Combinatorial Index*, San Diego, Academic Pr., 1998). This approach appeals by the possibility of desymmetryzing the dicarboxydiadamantane with high effectiveness since depending on the resin used cross linking is rather unlikely.

The 1-bromo-1'-carboxy-diadamantane shown in Scheme 3 is another good starting point to access the compounds of the invention. This compound may be prepared from the bromo- or carboxydiadamantane by carboxylation or bromination, respectively. The former reaction may be conducted using the 1-bromodiadamantane and formic acid in combination with sulfuric acid, oleum, and/or nitric acid at temperatures between −10° C. and 60° C. (see e.g. JP2006265224). The latter transformation may be achieved, for example, by treating the 1-carboxydiadamantane with bromine in a solvent such as e.g. acetic acid, water, dichloromethane, chloroform, tetrachloromethane, hexane, mixtures thereof or without a solvent at 10 to 110° C.

Scheme 3. Synthesis of 1-bromo-1'-carboxy-3,3'-diadamantane

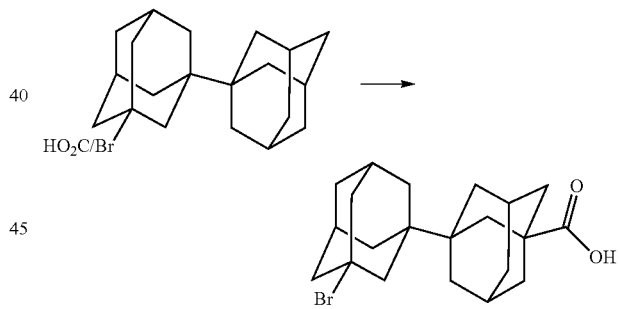

Starting from 1-bromo-1'-carboxy-3,3'-diadamantane (het)arylated diadamantanes are accessible; R' and (het)aryl in Scheme 4 are defined as hereinbefore. Phenyl (=(het)aryl) derivatives of the diadamantane may be obtained by reacting the bromodiadamantane with benzene or a derivative thereof in the presence of a catalyst such as palladium on carbon in e.g. N,N-dimethylformamide, N,N-dimethylacetamide, or N-methylpyrrolidinone, and optionally a base such as $K_2CO_3$ at 60 to 140° C. (see e.g. *Synthesis* 1998, 148-152). These conditions also allow the introduction of olefinic residues from alkenes, e.g. styrene or $C_{1-6}$-alkyl ethylene derivatives. Heteroaromatics such as e.g. pyridines, pyrimidines, quinolines, xanthines, and benzothiazoles may be introduced by replacing the bromine with the respective heteroaromatic via a radical pathway. Radicals derived from silanes and stannanes, generated by a radical initiator such as azobisisobutyronitrile or dibenzoyl peroxide, are routinely used to generate radical intermediates from alkyl bromides. These radicals may add to olefinic (e.g. acrylic acid or vinyl sulfonyl derivatives) and aromatic double bonds, such as the one mentioned above, affording the corresponding addition or substitution product. Tributyltin hydride, hexabutylditin, tris(trimethylsilyl)silane, and tetraphenyldisilane are among the reagents most often used for this purpose. Toluene, benzene, ethanol, and tetrahydrofuran are preferably employed at 60° C. to reflux temperature (see e.g. *Tetrahedron Lett.* 1998, 39, 1921-1924). Another general approach to replace the bromine with an aromatic is to employ the well-known Friedel-Crafts alkylation method. During the course of this reaction the bromodiadamantane is converted into a carbenium ion which in turn adds to aromatic rings and eventually replaces a hydrogen on them. The reaction is usually conducted in the presence of a Lewis acid, e.g. $AlCl_3$, $AlBr_3$, $FeCl_3$, $AgSbF_6$, $ZnCl_2$ in e.g. dichloromethane, 1,2-dichloroethane, hexane, or using the aromatic to react in excess at −20° C. to 120° C.

Scheme 4. Derivatization of 1-bromo-1'-carboxy-3,3'-diadamantane

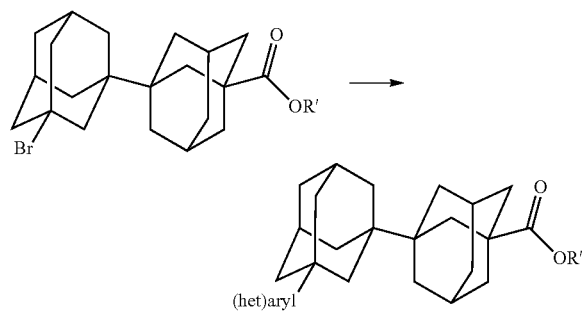

The bromine of the carboxydiadamantane may also be replaced with other nucleophiles such as the ones mentioned in Scheme 5. For instance, reaction with CuCN*pyridine in e.g. N,N-dimethylformamide or N-methylpyrrolidinone at elevated temperature may provide the cyano derivative, treatment with water in e.g. tetrahydrofuran, 1,4-dioxane, N,N-dimethylformamide, N,N-dimethylacetamide, N-methylpyrrolidinone, dimethylsulfoxide, alcohol, or water itself optionally in the presence of a catalyst such e.g. $Ag_2O$, $Ag_2CO_3$, or $AgNO_3$ and/or a base, e.g. $K_2CO_3$ or pyridine, may deliver the hydroxy derivative, reaction with an aliphatic alcohol, optionally bearing functional and (het)aryl groups, in the presence of a base, e.g. triethylamine, diisopropylethylamine, or pyridine, and optionally a catalyst such as $Ag_2O$, $AgBF_4$, $Ag_2CO_3$, or $AgNO_3$ at temperatures of 20 to 160° C. may provide the corresponding adamantyl ether, heating with a phenol derivative optionally in the presence of a base such as pyridine may afford the aryl adamantyl ether, heating with an electron-rich aromatic such as anisole or phenol may give the aromatic substitution product, treatment with the silver anion of a bissulfonyl amide such as bistosyl amide in benzene at room temperature or treatment with an azide such as trimethylsilyl azide in the presence of a Lewis acid such as $SnCl_4$ in $CH_2Cl_2$ at elevated temperature may deliver the corresponding nitrogen derivatized diadamantanes. Introduction of a sulfur atom as thiol may be achieved by reacting the diadamantyl bromide with thiourea in a mixture of HBr and acetic acid.

Using Grignard reagents as carbon nucleophiles allows the introduction of alkyl, allyl, and aryl groups (see e.g. *J. Org. Chem.* 2001, 66, 2034-2043). The reaction may be performed in solvents such as hexanes, tetrahydrofuran, ether, 1,4-dioxane, 1,2-dimethoxyethane, dichloromethane, toluene, N-methylpyrrolidinone, or mixtures thereof at temperatures between −30 to 100° C. Additives such as silver salts, e.g. $AgSO_3CF_3$, may be advantageous or even essential for the reaction to proceed.

CH-acidic compounds such as e.g. β-carbonyl esters and ketones may be used as carbon nucleophiles to replace the bromine atom, too (see e.g. *Tetrahedron* 1986, 45, 4253-4257, *Tetrahedron Lett.* 1988, 29, 1465-1468, and references quoted therein). Heating the cobalt salt of the dicarbonyl compound in e.g. chlorobenzene or chloroform is one way to achieve this transformation. The bromine of the diadamantane may be replaced with ordinary ketones and esters at the α-position to the carbonyl group as well. Transforming the ketone or ester into the corresponding trimethylsilyl enol ether and reacting this compound with the bromodiadamantane in the presence of a Lewis acid such as $TiCl_4$ or $ZnCl_2$ in dichloromethane at −0 to −70° C. is for example one variant to accomplish this replacement (see e.g. *Angew. Chem. Int. Ed. Engl.* 1979, 18, 72).

Scheme 5. Derivatization of 1-bromo-1'-carboxy-3,3'-diadamantane

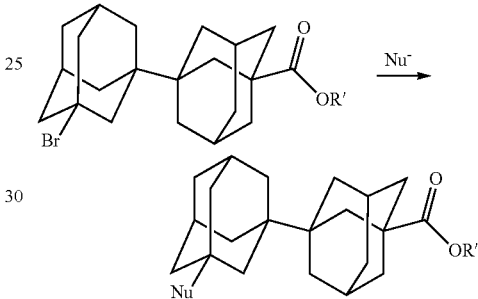

Nu = N nucleophiles such as NC—$C_{1-4}$-alkyl, $H_2$NCO—$C_{1-4}$-alkyl, ($C_{1-4}$-alkyl)HNCO—$C_{1-4}$-alkyl, HN($SO_2$(het)aryl)$_2$ O nucleophiles such as $OH_2$, HO—$C_{1-6}$-alkyl, HO-(het)aryl, HO—CO—$C_{1-6}$-alkyl, S nucleophiles such as S=C($NH_2$)$_2$ C nucleophiles such as $CN^-$, phenols, anisoles, anilines, ketones, carboxylic esters In the following a few synthetic procedures to elaborate the compounds described above are summarized to access the compounds of the invention.

If in the process of manufacture according to the invention a compound of general formula I is obtained which contains an amino, alkylamino or imino group, this may be converted by acylation or sulfonylation into a corresponding acyl or sulfonyl compound of general formula I.

If a compound of general formula I is obtained which contains a hydroxy group, this may be converted by acylation or sulfonylation into a corresponding acyl or sulfonyl compound of general formula I.

If a compound of general formula I is obtained which contains a hydroxy group, this may be converted by alkylation into a corresponding ether of general formula I.

If a compound of general formula I is obtained which contains an amino, alkylamino, or imino group, this may be converted by alkylation or reductive alkylation into a corresponding alkyl compound of general formula I.

If a compound of general formula I is obtained which contains an amino group, this may be converted by reaction with an isocyanate or carbamoyl chloride into a corresponding urea derivative of general formula I.

If a compound of general formula I is obtained which contains a nitro group, this may be converted by reduction into a corresponding amino compound.

If a compound of general formula I is obtained which contains an imino group, this may be converted by nitrosation and subsequent reduction into a corresponding N-aminoimino compound.

If a compound of general formula I is obtained which contains a $C_{1-3}$-alkyloxycarbonyl group, this may be converted by cleavage of the ester into the corresponding carboxy compound.

If a compound of general formula I is obtained which contains a carboxy group, this may be converted by esterification into a corresponding ester of general formula I.

If a compound of general formula I is obtained which contains a carboxy or ester group, this may be converted by reaction with an amine into a corresponding amide of general formula I.

If a compound of general formula I is obtained which contains a carboxy or activated carboxy group (e.g. anhydride, acyl halide), this may be converted into a corresponding amino, isocyanate, urea, and carbamoyl compound of general formula I by a one-carbon degradation reaction.

If a compound of general formula I is obtained which contains an aromatic substructure, this may be derivatized with a chlorine, bromine, or iodine atom or a nitro, sulfonic acid, chlorosulfonyl, or acyl group to a correspondingly derivatized aromatic compound of general formula I by an electrophilic substitution reaction.

If a compound of general formula I is obtained which contains an aromatic amino group, this may be transformed into a corresponding aromatic cyano, fluoro, chloro, bromo, iodo, hydroxy, mercapto, or azido compound of general formula I by diazotization and subsequent replacement of the diazo group with cyanide, fluoride, chloride, bromide, iodide, hydroxide, alkyl or hydrogen sulfide, or azide, respectively.

If a compound of general formula I is obtained which contains an aromatic amino group, this may be converted into a corresponding (het)aryl derivatized aromatic compound of general formula I by diazotization and subsequent replacement of the diazo group with an appropriate (het)aryl nucleophile mediated by a suited transition metal species.

If a compound of general formula I is obtained which contains an aromatic chloro, bromo, iodo, trifluoromethylsulfonyloxy, mesyloxy, or tosyloxy group, this may be converted into a corresponding aryl, alkenyl, alkynyl, or alkyl derivatized aromatic compound of general formula I by replacement of the respective group by aryl, alkenyl, alkynyl, or alkyl using a transition metal species mediated process.

If a compound of general formula I is obtained which contains an aromatic chloro, bromo, iodo, trifluoromethylsulfonyloxy, mesyloxy, or tosyloxy group, this may be replaced for hydrogen to give a corresponding aromatic compound of general formula I.

If a compound of general formula I is obtained which contains at two adjacent carbon atoms or at two carbon atoms separated by another carbon atom heteroatoms that are amino and hydroxy, amino, or mercapto, these heteroatoms may be linked via a carboxy carbon atom to form a cyclic amidine, imino ester, or imino thioester substructure that may be part of an aromatic ring.

If a compound of general formula I is obtained which contains a carboxy group this compound may be transformed into a compound bearing instead of the carboxy group a cyclic amidine, imino ester, or imino thioester substructure that may be part of an aromatic ring.

If a compound of general formula I is obtained which contains a cyano group, this may be converted into an amino alkyl derivatized compound of general formula I by reduction.

If a compound of general formula I is obtained which contains a cyano group, this may be converted into a N-hydroxycarbamimidoyl group by the treatment with hydroxylamine.

If a compound of general formula I is obtained which contains an N-hydroxycarbamimidoyl group, this may be converted to an oxadiazole derivatized compound of general formula I by the treatment with a carboxylic or related group.

If a compound of general formula I is obtained which contains an aminocarbonyl group, this may be converted by dehydration into a corresponding cyano compound of general formula I.

If a compound of general formula I is obtained which contains a keto or aldehydic group, this may be converted by reduction into a corresponding hydroxy compound of general formula I.

If a compound of general formula I is obtained which contains a keto or aldehydic group, this may be converted by reaction with a carbon nucleophile into a corresponding hydroxy alkyl compound of general formula I.

If a compound of general formula I is obtained which contains a cyano group, this may be converted into a corresponding tetrazolyl compound of general formula I by reacting with an azide salt or derivative.

The subsequent esterification is optionally carried out in a solvent or mixture of solvents such as methylene chloride, N,N-dimethylformamide, benzene, toluene, chlorobenzene, tetrahydrofuran, benzene/tetrahydrofuran or 1,4-dioxane or particularly advantageously in the corresponding alcohol optionally in the presence of an acid such as hydrochloric acid or in the presence of a dehydrating agent. Isobutyl chloroformate, thionyl chloride, trimethylchlorosilane, sulfuric acid, methanesulfonic acid, p-toluenesulfonic acid, phosphorus trichloride, phosphorus pentoxide, N,N'-dicyclohexylcarbodiimide, N,N'-dicyclohexyl-carbodiimide/N-hydroxysuccinimide, N,N'-carbonyldiimidazole, triphenylphosphine/carbon tetrachloride, or combinations thereof optionally in the presence of 4-dimethylaminopyridine and/or 1-hydroxybenzotriazole are among the routinely used reagents to accomplish this transformation. The reactions are conducted between 0 and 150° C., preferably between 0 and 80° C.

The subsequent ester formation may also be carried out by reacting a compound which contains a carboxy group in the presence of a base with a corresponding alkyl halide.

The subsequent acylation or sulfonylation is optionally carried out in a solvent or mixture of solvents such as methylene chloride, N,N-dimethylformamide, benzene, toluene, chlorobenzene, tetrahydrofuran, benzene/tetrahydrofuran, or 1,4-dioxane with a corresponding acyl or sulfonyl derivative optionally in the presence of a tertiary organic base or in the presence of an inorganic base or in the presence of a dehydrating agent. Routinely used agents are e.g. isobutyl chloroformate, thionyl chloride, trimethylchlorosilane, sulfuric acid, methanesulfonic acid, p-toluenesulfonic acid, phosphorus trichloride, phosphorus pentoxide, N,N'-dicyclo-hexylcarbodiimide, N,N'-dicyclohexylcarbodiimide/N-hydroxysuccinimide, N,N'-carbonyldiimidazole, triphenylphosphine/carbon tetrachloride, or combinations thereof that may be employed in the presence of 4-dimethylaminopyridine and/or 1-hydroxybenzotriazole at temperatures between 0 and 150° C., preferably between 0 and 80° C.

The subsequent alkylation is optionally carried out in a solvent or mixture of solvents such as methylene chloride, N,N-dimethylformamide, benzene, toluene, chlorobenzene, tetrahydrofuran, benzene/tetrahydrofuran, or 1,4-dioxane with an alkylating agent such as a corresponding halide or sulfonic acid ester, e.g. methyl iodide, ethyl bromide, dimethylsulfate, or benzyl chloride, optionally in the presence of a tertiary organic base or in the presence of an inorganic base at temperatures between 0 and 150° C., preferably between 0 and 100° C.

The subsequent reductive alkylation is carried out with a corresponding carbonyl compound such as e.g. formaldehyde, acetaldehyde, propionaldehyde, acetone, or butyraldehyde in the presence of a complex metal hydride such as sodium borohydride, lithium borohydride, sodium triacetoxyborohydride, or sodium cyanoborohydride conveniently at a pH of 6-7 and at ambient temperature or using hydrogen in the presence of a transition metal catalyst, e.g. palladium/charcoal at a hydrogen pressure of 1 to 5 bar. Methylation may also be carried out in the presence of formic acid as reducing agent at elevated temperature, e.g. between 60 and 120° C.

The subsequent urea formation from an amine is optionally carried out in a solvent or mixture of solvents such as N,N-dimethylformamide, N-methylpyrrolidinone, toluene, acetonitrile, dichloromethane, 1,2-dichloroethane, ether, tetrahydrofuran, 1,2-dimethoxyethane, or 1,4-dioxane with an isocyanate or carbamoyl chloride optionally in the presence of a tertiary organic base, e.g. triethylamine or ethyldiisopropylamine, or in the presence of an inorganic base, e.g. potassium carbonate or calcium oxide, at temperatures between 0 and 180° C., preferably between 5 and 120° C. Additives such as pyridine or 4-dimethylaminopyridine may be beneficial.

The subsequent reduction of a nitro group is carried out, for example, with hydrogen and a catalyst such as palladium on carbon, platinum dioxide, or Raney nickel, or using other reducing agents such as iron or zinc in the presence of an acid such as acetic acid.

The subsequent nitrosation of an imino group followed by reduction to obtain the N-amino-imino compound is carried out, for example, with an alkyl nitrite such as isoamyl nitrite to form the N-nitroso-imino compound that is then reduced to the N-amino-imino compound using, for example, zinc in the presence of an acid such as acetic acid.

The subsequent cleaving of a $C_{1-3}$-alkyloxycarbonyl group to obtain the carboxylic acid is carried out, for example, by hydrolysis with an acid such as hydrochloric acid or sulfuric acid or an alkali metal hydroxide such as lithium hydroxide, sodium hydroxide, or potassium hydroxide.

The subsequent amide formation is carried out by reacting a reactive carboxylic acid derivative with a corresponding amine optionally in a solvent or mixture of solvents such as methylene chloride, N,N-dimethylformamide, benzene, toluene, chlorobenzene, tetrahydrofuran, benzene/tetrahydrofuran or 1,4-dioxane, while the amine used may also serve as solvent, optionally in the presence of a tertiary organic base or in the presence of an inorganic base or with a corresponding carboxylic acid in the presence of a dehydrating agent. Isobutyl chloroformate, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccin-imide, 1-hydroxybenzotriazole, N,N'-carbonyldiimidazole or triphenylphosphine/carbon tetrachloride, or combinations thereof optionally in the presence of 4-dimethylaminopyridine at temperatures between 0 and 150° C., preferably between 0 and 80° C., may be applied to achieve the coupling.

The subsequent replacement of a carboxylic acid or an activated carboxylic acid derivative with a nitrogen group may be accomplished by rearrangement of the corresponding acyl azide (see e.g. literature on Curtius degradation/rearrangement and Hofmann degradation/rearrangement). The acyl azide may be obtained by reaction of the carboxylic acid with $(PhO)_2P(O)N_3$ in the presence of a base, e.g. triethylamine, diisopropylethylamine, pyridine, 4-dimethylaminopyridine, or $Cs_2CO_3$, in e.g. cyclohexane, tert-butanol, toluene, benzene, dichloromethane, 1,2-dichloroethane, 1,4-dioxane, tetrahydrofuran, dimethylformamide, or mixtures thereof. Starting with an activated carboxylic function, e.g. acyl chloride, mixed anhydride with e.g. a carbamic acid, carbonic acid ester, or phosphoric acid ester, aryl ester such as pentafluorophenyl or 4-nitrophenyl ester, alkyl- or arylthio ester, the acyl azide may be obtained by treatment with an azide nucleophile, e.g. sodium azide or trimethylsilyl azide, optionally in the presence of an additive, e.g. $Bu_4NBr$, preferably in toluene, benzene, tetrahydrofuran, ether, 1,4-dioxane, dichloromethane, N,N-dimethylformamide, N-methylpyrrolidinone, acetonitrile, acetone, water, or mixtures thereof; depending on the azide used some of them are not suitable. The acyl azide is rearranged at elevated temperatures, preferably between 60 and 140° C., to give the isocyanate which may be isolated depending on the solvent and additives used or directly reacted further to give the free amine by hydrolysis, the carbamic ester by reaction with an alcohol, or the urea derivative by addition of ammonia, a primary or secondary amine.

The subsequent introduction of a chlorine, bromine, or iodine atom onto an aromatic substructure may be carried out by reacting the aromatic compound with an appropriate electrophile of the halogen atom. Suited chlorine and bromine electrophiles may be e.g. N-halosuccinimide, HOCl, HOBr, tertBuOCl, tertBuOBr, chlorine, bromine, dibromoisocyanuric acid, pyridinium dichlorobromate, pyridinium tribromide, or sulfuryl chloride that may be used alone or in combination with an acid, e.g. hydrochloric acid, hydrobromic acid, tetrafluoroboric acid, triflic acid, sulfuric acid, or acetic acid, or a Lewis acid, e.g. iron(III) halide, borontrifluoride hydrate, borontrifluoride etherate, or aluminum halide. Further useful combinations may be LiBr and ceric ammonium nitrate, KCl or KBr with Oxone®, or KBr and sodium perborate. Suited iodine electrophiles may be generated from iodine combined with an oxidizing agent such as nitric acid, sulfur trioxide, manganese dioxide, $HIO_3$, hydrogen peroxide, sodium periodate, peroxydisulfates, and Oxone®. Further suited iodine electrophiles may be e.g. iodine chloride, dichloroiodates, and N-iodosuccinimide. These iodine electrophiles may be used without an additive or in the presence of an acid such as e.g. acetic acid, trifluoroacetic acid, or sulfuric acid, or a Lewis acid such as borontrifluoride hydrate, or copper salts. If a nitro group is to be introduced appropriate nitro electrophiles may be generated from, for example, nitric acid, acetyl nitrate, ceric ammonium nitrate, sodium nitrate, $N_2O_5$, alkyl nitrate, and nitronium tetrafluoroborate. Some of these reagents may be used without an additive, though, several of them are better used in combination with an acid, e.g. sulfuric acid or triflic acid, acetic anhydride, trifluoroacetic anhydride, Lewis acid, e.g. ytterbium triflate or iron acetate, $P_2O_5$, or a base. The $SO_3H$ group may be introduced by reacting the aromatic compound with, for example, concentrated sulfuric acid, $SO_3$, $ClSO_3H$, or $ClSO_2NMe_2$ combined with indium triflate. Reacting the aromatic compound with $ClSO_3H$ gives the corresponding chlorosulfonylated derivative that may be hydrolyzed to the sulfonic acid. Acylating the aromatic part is conducted using an acyl electrophile that may be generated from the respective acyl halide, e.g. chloride, or acyl anhydride and a Lewis acid such as e.g. aluminum halide, diethylaluminum halide, indium halide, iron(III) halide, tin(IV) halide, borontrifluoride, titanium(IV) halide, or a Brønsted acid, e.g. sulfuric acid or triflic acid. The formyl group is best introduced using the so-called Vilsmeier or Vilsmeier-Haack conditions: dialkylformamide combined with phosgene, thionyl chloride, $POCl_3$, or oxalyl chloride. Preferred solvents for the electrophilic substitutions described may differ depending on the electrophile employed; in the following some more generally applicable are mentioned: methylene chloride, dichloroethane, chlorobenzene, dichlorobenzene, ether, fluorinated hydrocarbons, hexanes, quinoline, or acetonitrile. The temperatures preferably applied range from 0 to 180° C.

The subsequent replacement of an aromatic amino group is initiated by diazotization of the amino group using a nitrous acid or nitrosonium source or equivalent such as a nitrite salt combined with an acid, e.g. sodium nitrite and hydrochloric acid, nitrosonium tetrafluoroborate, or an alkyl nitrite, e.g. tertbutyl nitrite or isoamyl nitrite. The diazotization is optionally carried out in methylene chloride, dichloroethane, N,N-dimethylformamide, N-methylpyrrolidinone, benzene, toluene, chlorobenzene, tetrahydrofuran, water, ethyl acetate, alcohol, ether, 1,2-dimethoxyethane, 1,4-dioxane, or mixtures thereof at temperatures between −10° C. and 100° C. (diazotization of amino groups is detailed in, for example, *Angew. Chem. Int. Ed.* 1976, 15, 251). The subsequent displacement of the diazo group for a cyano group, chlorine, or bromine using cuprous cyanide, chloride, or bromide, respectively, is known as the Sandmeyer reaction (see e.g. March's Advanced Organic Chemistry, Michael B. Smith and Jerry March, John Wiley & Sons Inc., 6. Ed., New Jersey, 2007 and references quoted therein); the reaction is optionally conducted between −10° C. and 120° C. in one of the solvents or mixtures mentioned above. The replacement of the diazo group for a fluorine atom may be achieved with a tetrafluoroborate salt or tetrafluoroboric acid and heating to 20 to 160° C.; the reaction is known as the Schiemann reaction. Iodine may be introduced by treatment of the diazo compound with an iodide salt, e.g. sodium iodide, preferably using water or an aqueous solvent mixture at temperatures between 0 and 120° C. The diazo group is replaced for hydroxy using water or an aqueous solvent mixture at temperatures between 0 and 180° C. The reaction usually works without further additives but the addition of cuprous oxide or strong acid may be advantageous. Mercapto or alkylmercapto may be introduced via their corresponding disulfide salts or dialkyldisulfides at temperatures between 0 and 120° C.; depending on the sulfur species used an inert solvent or aqueous solvent system may be preferred (see e.g. *Synth. Commun.* 2001, 31, 1857 and references quoted therein).

The subsequent replacement of an aromatic amino group by an aryl group may be carried out via the corresponding diazo compound obtainable as described above. The reaction with an aryl nucleophile, preferably an aryl boronic acid, boronic ester, trifluoroborate, zinc halide, or stannane, is conducted in the presence of a transition metal species derived from palladium, nickel, rhodium, copper, or iron, preferably palladium. The active catalyst may be a complex of the transition metal with ligands such as e.g. phosphines, phosphites, imidazole carbenes, imidazolidine carbenes, dibenzylideneacetone, allyl, or nitriles, an elemental form of the transition metal such as palladium on carbon or nanoparticles, or salts such as chloride, bromide, acetate, or trifluoroacetate. In these reactions the diazo compound is preferably employed as its tetrafluoroborate salt optionally in methylene chloride, N,N-dimethylformamide, N-methylpyrrolidinone, benzene, toluene, tetrahydrofuran, water, ethyl acetate, alcohol, ether, 1,2-dimethoxyethane, 1,4-dioxane, or mixtures thereof at temperatures between 10° C. and 180° C., preferably between 20° C. and 140° C.

The subsequent replacement of an aromatic chloro, bromo, iodo atom or an aromatic trifluoromethylsulfonyloxy, mesyloxy, or tosyloxy group for an aryl, alkenyl, alkynyl, or alkyl residue is preferably mediated by a transition metal species derived from palladium, nickel, rhodium, copper, or iron. The active catalyst may be a complex of the transition metal with ligands such as e.g. phosphines (e.g. tritertbutylphosphine, tricyclohexylphosphine, substituted biphenyldicyclohexylphosphines, substituted biphenylditertbutylphosphines, triphenylphosphine, tritolylphosphine, trifurylphosphine, 1,1'-bis(diphenylphosphino)-ferrocene), phosphites, imidazole carbenes, imidazolidine carbenes, dibenzylideneacetone, allyl, or nitriles, an elemental form of the transition metal such as palladium on carbon or nanoparticles of iron or palladium, or a salt such as fluoride, chloride, bromide, acetate, triflate, or trifluoroacetate. The replacement is preferably conducted with a trifluoroborate, boronic acid, or boronic ester (Suzuki or Suzuki-type reaction), zinc halide (Negishi or Negishi-type reaction), stannane (Stille reaction), silane (Hiyama or Hiyama-type reaction), magnesium halide (Kumada or Kumada-type reaction) of the aryl, alkenyl, or alkyl residue to be introduced. The terminal alkyne is preferably used as it is or as the zinc acetylide derivative. Depending on the electrophilic and nucleophilic reaction partners additives such as halide salts, e.g. lithium chloride, potassium fluoride, tetrabutylammonium fluoride, hydroxide sources such as potassium hydroxide, potassium carbonate, silver salts such as silver oxide or triflate, copper salts such as copper chloride or copper thiophenecarboxylate may be advantageous or even essential. Copper iodide is a preferred additive in the coupling with a terminal alkyne group (Sonogashira reaction). The coupling reactions are optionally conducted in methylene chloride, N,N-dimethylformamide, N-methylpyrrolidinone, benzene, toluene, tetrahydrofuran, water, ethyl acetate, alcohol, ether, dimethylsulfoxide, 1,2-dimethoxyethane, 1,4-dioxane, or mixtures thereof, though, depending on the nucleophile some of them are less or not suited at all. Preferred temperatures are in the range from −10° C. to 180° C.

The subsequent replacement of an aromatic chlorine, bromine, or iodine atom or an aromatic trifluoromethylsulfonyloxy, mesyloxy, or tosyloxy group for a hydrogen atom is preferably mediated by a transition metal species derived from palladium, nickel, platinum, or rhodium. The active catalyst may be a complex of the transition metal with ligands, an elemental form, or a salt of the transition metal as mentioned above. Raney nickel or palladium on carbon are among the preferred catalyst species. Suited hydrogen sources may be hydrogen, preferably at pressures of 1 to 5 bar, silanes, e.g. trialkoxysilane, boranes, hydrides, e.g. alkali metal borohydride, formic acid, or formates, e.g. ammonium formate. The reactions are preferably carried out in methylene chloride, N,N-dimethylformamide, N,N-dimethylacetamide, N-methyl-pyrrolidinone, benzene, toluene, tetrahydrofuran, water, ethyl acetate, alcohol, ether, 1,2-dimethoxyethane, 1,4-dioxane, or mixtures thereof at −10° C. to 180° C., more preferably at 20° C. to 140° C.

The subsequent cyclization starting from a compound bearing heteroatoms at two adjacent carbon atoms or at two carbon atoms separated by one carbon atom is optionally conducted with a carboxy equivalent such as nitrile, carboxylic chloride or fluoride, carboxylic acid, ketene, carboxylic ester, or carboxylic thioester. The overall transformation consists of two reaction steps: attachment of the carboxy equivalent to one of the two heteroatoms followed by cyclization with the other heteroatom. The first step is an amide formation with the amino functionality that may be carried out as described hereinbefore. The ensuing reaction step, cyclization with the second heteroatom, may be accomplished by heating in the presence of an acid, e.g. acetic acid, trifluoroacetic acid, sulfuric acid, or hydrochloric acid, or a base, e.g. sodium hydroxide, sodium ethoxide, or sodium tertbutoxide. The use of dehydrating reagents such as anhydrides, e.g. acetic anhydride, orthoesters, e.g. trimethylorthoformate, thionyl chloride, phosgene, diphosgene, triphosgene, phosphorus oxychloride, phosphorus pentachloride, dialkylcarbodiimides, combinations of phosphines, e.g. triphenylphosphine or trialkylphosphine with dialkyl azodicarboxylates, bromine, iodine, or 1,2-dihaloethanes, e.g. 1,2-dibromotetrafluoroethane, may be advantageous. The reactions are preferably carried out in inert solvents or mixtures such as methylene chloride, dichloroethane, benzene, toluene, tetrahydrofuran, ether, or combinations thereof, though, cyclization in the presence of an acid or a base may also be conducted in water or an alcohol, e.g. methanol, ethanol, isopropanol, or tertbutanol, or combinations with these solvents. The reactions are carried out at temperatures between 0° C. and 200° C., preferably between 20° C. and 140° C. The opposite way around, starting from a compound of formula I bearing a carboxy group or a derivative thereof, is analogously conducted.

The subsequent reduction of a cyano group to obtain an aminomethyl group is optionally conducted with hydrogen in the presence of a transition metal species or with a hydride. Suited transition metals may be derived from palladium, nickel, platinum, rhodium, or ruthenium such as, for example, palladium on charcoal, palladium hydroxide, platinum oxide, or Raney nickel that may be used in solvents such as ethyl acetate, alcohols, e.g. methanol or ethanol, dichloromethane, tetrahydrofuran, ether, benzene, toluene, N,N-dimethylformamide, or N-methylpyrrolidinone at hydrogen pressures between 1 and 10 bar, preferably between 1 and 5 bar, and at temperatures between 0 and 180° C., preferably between 20 and 120° C. Additives such as acids, e.g. hydrochloric acid, methanesulfonic acid, sulfuric acid, or acetic acid, may be beneficial to the reaction. Appropriate hydride sources may be selected from e.g. borohydrides, e.g. sodium borohydride, potassium trisecbutylborohydride, borane, or lithium triethylborohydride, or alanates, e.g. lithium aluminum hydride or diisobutylaluminum hydride. Some of these reagents are best used in combination with nickel chloride or cobalt chloride as e.g. sodium borohydride. These reagents may be used in e.g. tetrahydrofuran, ether, 1,4-dioxane, 1,2-dimethoxyethane, dichloromethane, 1,2-dichloroethane, benzene, or toluene; some are also compatible with alcoholic solutions. Preferred reaction temperatures range from −80° C. to 160° C., more preferred from −40° C. to 80° C.

The subsequent formation of a N-hydroxycarbamimidoyl group from a cyano group may be carried out by the treatment of the cyano compound with hydroxylamine. The reaction is preferably conducted in aqueous or alcoholic solvents at temperatures between 0° C. and 140° C.

The subsequent formation of an oxadiazole from an N-hydroxycarbamimidoyl is optionally conducted with a carboxy equivalent such as nitrile, carboxylic chloride or fluoride, carboxylic acid, anhydride, ketene, carboxylic ester, or carboxylic thioester. The transformation is related to the formation of a ring starting from two adjacent heteroatoms described above and may be carried out analogously.

The subsequent formation of a cyano group from an amino carbonyl group is optionally conducted by using a dehydrating reagent such as e.g. anhydride, e.g. acetic anhydride, trifluoroacetic anhydride, or triflic anhydride, phosgene, thionyl chloride, oxalyl chloride, $POCl_3$, $PCl_5$, $P_4O_{10}$, triphenylphosphite, or triphenyl- or trialkylphosphine combined with tetrachloromethane, 1,2-dibromotetrafluoroethane, or bromine. The reactions are preferably carried out in dichloromethane, 1,2-dichloroethane, hexanes, ether, 1,4-dioxane, benzene, toluene, acetonitrile, mixtures thereof, or without a solvent at temperatures between 0° C. and 140° C. Additives such as amines, e.g. pyridine or triethylamine, or N,N-dimethylformamide may be beneficial.

The subsequent reduction of a keto or an aldehydic group to obtain a secondary or primary alcohol may be carried out with a complex metal hydride such as sodium borohydride, lithium borohydride, lithium triethylborohydride, diisobutylaluminum hydride, or lithium aluminum hydride. The reductions may be conducted in e.g. dichloromethane, 1,2-dichloroethane, hexanes, ether, 1,4-dioxane, tetrahydrofuran, N,N-dimethylformamide, N-methylpyrrolidinone, benzene, toluene, alcohols, e.g. methanol, water, or mixtures thereof, though, not all reducing agents are compatible with all of these solvents. Preferred temperatures are between −80° C. and 140° C. depending on the reducing power of the reagent. Alternatively, hydrogen in the presence of a transition metal catalyst may be used for the reduction.

The subsequent addition of a carbon nucleophile to a keto or an aldehydic group to obtain a tertiary or secondary alcohol may be carried out with an alkyl or (het)aryl metal compound, preferably with a lithium or magnesium derivative. The reactions are preferably conducted in hexanes, ether, 1,4-dioxane, tetrahydrofuran, 1,2-dimethoxyethane, benzene, toluene, or mixtures thereof between −80° C. and 50° C.

The subsequent conversion of a cyano into a tetrazolyl group may be achieved by reacting the cyanide with sodium azide or trimethylsilyl azide in e.g. toluene, xylene, cyclohexane, N,N-dimethylformamide, N,N-dimethylacetamide, N-methylpyrrolidinone, tetrahydrofuran, 1,4-dioxane, 1,2-dimethoxyethane, alcohol, water, mixtures thereof or without a solvent. Beneficial additives may be $ZnBr_2$, $Bu_3SnCl$, $NH_4Cl$, $Bu_2SnO$, $AlCl_3$, $AlMe_3$, $HNEt_3Cl$, $Bu_4NF$, and $NEt_3$. The reactions are preferably conducted between 20° C. and 180° C.

Besides the strategies presented a host of additional approaches to attach various residues R to the diadamantane framework can be envisaged and are also reported in the organic chemistry literature. Therefore, the preceding synthetic strategies and transformations are in no way meant to restrict the possible pathways to access the compounds of the invention but are only supposed to show a few routes by way of example.

The synthetic routes presented may rely on the use of protecting groups. Suitable protecting groups for the respective functionalities and their removal are described hereinafter (see also: *Protecting Groups*, Philip J. Kocienski, 3$^{rd}$ edition, Georg Thieme Verlag, Stuttgart, 2004 and references quoted therein).

In the reactions described hereinbefore, any reactive group present such as hydroxy, carboxy, amino, alkylamino, or imino group may be protected during the reaction by conventional protecting groups which are cleaved again after the reaction.

For example, a protecting group for a hydroxy group may be a trimethylsilyl, tertbutyldimethylsilyl, triisopropylsilyl, acetyl, pivaloyl, benzoyl, methyl, tert-butyl, allyl, trityl, benzyl, 4-methoxybenzyl, tetrahydropyranyl, methoxymethyl, ethoxymethyl, or 2-trimethylsilylethoxymethyl group, protecting groups for a carboxy group may be trimethylsilyl, methyl, ethyl, tertbutyl, allyl, benzyl, or tetrahydropyranyl, protecting groups for a ketone or aldehyde may be a ketal or acetal, respectively, e.g. derived from methanol, glycol, or propane-1,3-diol, protecting groups for an amino, alkylamino, or imino group may be methyl, formyl, acetyl, trifluoroacetyl, ethoxycarbonyl, tert-butoxycarbonyl, benzyloxycarbonyl, benzyl, methoxy-benzyl, or 2,4-dimethoxybenzyl and for the amino group additionally phthalyl, and protecting groups for a terminal alkyne may be trimethylsilyl, trisopropylsilyl, tertbutyldimethylsilyl, or 2-hydroxy-isopropyl.

Any acyl protecting group may be cleaved, for example, hydrolytically in an aqueous solvent, e.g. in water, isopropanol/water, acetic acid/water, tetrahydrofuran/water, or 1,4-dioxane/water, in the presence of an acid such as trifluoroacetic acid, hydrochloric acid, or sulfuric acid or in the presence of an alkali metal base such as lithium hydroxide, sodium hydroxide, or potassium hydroxide or aprotically, e.g. in the presence of iodotrimethylsilane, at temperatures between 0 and 120° C., preferably between 10 and 100° C. A trifluoroacetyl group is preferably cleaved by treating with an acid such as hydrochloric acid, optionally in a solvent such as acetic acid, at temperatures between 50 and 120° C. or by treating with sodium hydroxide solution, optionally in an additional solvent such as tetrahydrofuran or methanol, at temperatures between 0 and 80° C.

Any acetal or ketal protecting group used may be cleaved, for example, hydrolytically in an aqueous solvent, e.g. in water, isopropanol/water, acetic acid/water, tetrahydrofuran/water, or 1,4-dioxane/water, in the presence of an acid such as trifluoroacetic acid, hydrochloric acid, or sulfuric acid or aprotically, e.g. in the presence of iodotrimethylsilane, at temperatures between 0 and 120° C., preferably between 10 and 100° C.

A trimethylsilyl group is cleaved, for example, in water, an aqueous solvent mixture or an alcohol, such as methanol or ethanol, in the presence of a base such as lithium hydroxide, sodium hydroxide, potassium carbonate, or sodium methoxide. Acids such as e.g. hydrochloric acid, trifluoroacetic acid, or acetic acid may also be suitable. The cleavage usually takes place at comparatively low temperatures, e.g. between −60 and 60° C. Silyl groups other than trimethylsilyl are preferentially cleaved in the presence of an acid, e.g. trifluoroacetic acid, hydrochloric acid, or sulfuric acid, at temperatures between 0° C. and 100° C. A particularly suited cleaving method for silyl groups is based on the use of fluoride salts, e.g. tetrabutylammonium fluoride, hydrogen fluoride, or potassium fluoride, in organic solvents, such as for example diethyl ether, tetrahydrofuran, 1,4-dioxane, 1,2-dimethoxyethane, toluene, benzene, dichloroethane, or dichloromethane at temperatures between −20 and 100° C.

A benzyl, methoxybenzyl, or benzyloxycarbonyl group is advantageously cleaved hydrogenolytically, e.g. with hydrogen in the presence of a catalyst such as palladium on carbon, palladium hydroxide, or platinum oxide in a solvent such as methanol, ethanol, ethyl acetate, or glacial acetic acid, optionally in the presence of an acid, such as hydrochloric acid, at temperatures between 0 and 100° C., preferably between 20 and 60° C., and at hydrogen pressures of 1 to 7 bar, preferably 3 to 5 bar. Trimethylsilyl iodide, boron trichloride, or boron trifluoride in the presence of a scavenger such as anisol, thioanisol, or pentamethylbenzene may also be used with benzylether derivatives. An electron-rich benzyl residue, such as methoxybenzyl, may also be cleaved oxidatively with e.g. 2,3-dichloro-5,6-dicyano-1,4-benzoquinone (DDQ) or ceric ammonium nitrate (CAN) preferably in an alcoholic or aqueous solvent at temperatures between 10 and 120° C. A 2,4-dimethoxybenzyl group is preferably cleaved in trifluoroacetic acid in the presence of a scavenger such as anisole.

A tertbutyl or tertbutyloxycarbonyl group is preferably cleaved by treating with an acid such as trifluoroacetic acid, sulfuric acid, or hydrochloric acid or by treating with iodotrimethylsilane optionally using a solvent such as methylene chloride, 1,4-dioxane, methanol, isopropanol, water, or diethylether.

A methyl group at an tertiary amine may be cleaved by the treatment with 1-chloroethyl chloroformate. Hydrobromic acid and borontribromide are particularly suited for the cleavage of methylethers.

The compounds of general formula I may be resolved into their enantiomers and/or diastereomers, as mentioned before. Thus, for example, cis/trans mixtures may be resolved into their cis and trans isomers, and racemic compounds may be separated into their enantiomers.

The cis/trans mixtures may be resolved, for example, by chromatography into the cis and trans isomers thereof. The compounds of general formula I which occur as racemates may be separated by methods known per se (cf. Allinger N. L. and Eliel E. L. in "Topics in Stereochemistry", Vol. 6, Wiley Interscience, 1971) into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallisation from an optically active solvent or by reacting with an optically active substance which forms salts or derivatives, such as e.g. esters or amides, with the racemic compound. Salts may be formed with enantiopure acids for basic compounds and with enantiopure bases for acidic compounds. Diastereomeric derivatives are formed with enantiopure auxiliary compounds such as e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, di-o-tolyltartaric acid, malic acid, mandelic acid, camphorsulfonic acid, glutamic acid, aspartic acid, or quinic acid. Optically active alcohols applicable as auxiliary may be, for example, (+) or (−)-menthol and optically active acyl groups in amides may be, for example, (+)- or (−)-menthyloxycarbonyl.

As mentioned above, the compounds of formula I may be converted into salts, particularly for pharmaceutical use into the physiologically acceptable salts with inorganic or organic acids provided that compound I bears a basic residue. Acids which may be used for this purpose include for example hydrochloric acid, hydrobromic acid, sulfuric acid, methanesulfonic acid, phosphoric acid, fumaric acid, succinic acid, lactic acid, citric acid, tartaric acid, or maleic acid.

If the compounds of formula I contain an acidic residue like, for example, a carboxy group, they may be converted into the salts thereof with inorganic or organic bases, particularly for pharmaceutical use into the physiologically acceptable salts thereof. Suitable bases for this purpose include, for example, sodium hydroxide, potassium hydroxide, calcium hydroxide, calcium isopropoxide, magnesium hydroxide, magnesium ethoxide, ammonium hydroxide, cyclohexylamine, ethanolamine, diethanolamine, triethanolamine, N-methyl-D-glucamine, L-lysine, L-arginine, and piperazine.

The compounds according to the invention are advantageously also obtainable using the methods described in the examples that follow, which may also be combined for this purpose with methods known to the skilled man from the literature.

As already mentioned, the compounds of general formula (I) according to the invention, including those compounds comprised by the provisos (P1) and (P2), and the physiologically acceptable salts thereof have valuable pharmacological properties, particularly an inhibitory effect on the enzyme 11β-hydroxysteroid dehydrogenase (HSD) 1.

The biological properties of the new compounds may be investigated as follows:

In vitro inhibition of 11β-HSD1 by test compounds is determined with HTRF (Homogeneous Time-Resolved Fluorescence) technology (cisbio international, France) detecting cortisol generated from cortisterone by human liver microsomes. Briefly, compounds are incubated for 1 hour at 37° C. in Tris buffer (20 mM tris, 5 mM EDTA, pH 6.0) containing NADPH (200 μM) and cortisone (80 nM). Cortisol generated in the reaction is then detected with a competitive immunoassay, involving two HTRF conjugates: cortisol linked to XL665 and anti-cortisol antibody labeled with Europium cryptate. The incubation period for detection reaction is typically 2 hours. The amount of cortisol is determined by reading the time-resolved fluorescence of the wells (Ex 320/75 nm; Em 615/8.5 nm and 665/7.5 nm). The ratio of the two emission signals is then calculated (Em665*10000/Em615). Each assay contains incubations with vehicle controls instead of compound as controls for non-inhibited cortisol generation (100% CTL; 'high values') and incubations with carbenoxolone as controls for fully inhibited enzyme and cortisol background (0% CTL; 'low values'). Each assay also contains a calibration curve with cortisol to transform the fluorescent data into cortisol concentrations. Percent inhibition (% CTL) of each compound is determined relative to the carbenoxolone signal and $IC_{50}$ curves are generated.

The compounds of general formula I according to the invention for example have $IC_{50}$ values below 10000 nM, particularly below 1000 nM, most preferably below 200 nM. The % CTL values of some example compounds at a concentration of 1 μM are provided in the following Table 2 wherein 100% indicates no inhibition and a value of zero or below zero indicates complete inhibition. The measurement of % CTL is described hereinbefore.

TABLE 2

11β-HSD 1 inhibitory activity (% CTL at 1 μM) of the compounds compiled in Table 3

| Example | % CTL |
|---|---|
| 1 | −7 |
| 2 | 29 |
| 3 | −11 |
| 4 | −13 |
| 5 | 50 |
| 6 | 1 |
| 7 | 26 |
| 8 | 95 |
| 9 | 49 |
| 10 | −3 |
| 11 | −11 |
| 12 | 1 |
| 13 | 53 |
| 14 | −5 |

TABLE 2-continued

11β-HSD 1 inhibitory activity (% CTL at 1 μM) of the compounds compiled in Table 3

| Example | % CTL |
|---|---|
| 15 | 34 |
| 16 | 69 |
| 17 | −26 |
| 18 | −26 |
| 19 | 19 |
| 20 | 7 |
| 21 | 69 |
| 22 | 37 |
| 23 | −18 |
| 24 | −33 |
| 26 | 44 |
| 27 | 12 |
| 28 | 96 |
| 29 | −8 |
| 30 | 30 |
| 31 | 61 |
| 32 | 8 |
| 33 | 81 |
| 34 | 36 |
| 35 | −3 |
| 36 | 13 |
| 37 | 62 |
| 38 | 7 |
| 39 | 53 |
| 40 | −20 |
| 41 | 0 |
| 42 | −36 |
| 43 | −20 |
| 44 | −17 |
| 45 | 8 |
| 46 | 0 |
| 47 | −15 |
| 49 | 24 |
| 50 | −9 |
| 51 | 4 |

In view of their ability to inhibit the enzyme 11β-hydroxysteroid dehydrogenase (HSD) 1, the compounds of general formula (I) according to the invention, including those compounds comprised by the provisos (P1) and (P2), and the corresponding pharmaceutically acceptable salts thereof are theoretically suitable for the treatment and/or preventative treatment of all those conditions or diseases which may be affected by the inhibition of the 11β-hydroxysteroid dehydrogenase (HSD) 1 activity. Therefore, compounds according to the invention are particularly suitable for the prevention or treatment of diseases, particularly metabolic disorders, or conditions such as type 1 diabetes mellitus, type 2 diabetes mellitus, complications of diabetes (such as e.g. retinopathy, nephropathy or neuropathies, diabetic foot, ulcers, macroangiopathies, slow or poor wound healing), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, edema and hyperuricaemia. These substances are also suitable for preventing beta-cell degeneration such as e.g. apoptosis or necrosis of pancreatic beta cells. The substances are also suitable for treating, improving or restoring the functionality of pancreatic cells, and also of increasing the number and size of pancreatic beta cells. The compounds according to the invention may also be used as diuretics or antihypertensives and are suitable for the prevention and treatment of acute renal failure.

Additionally, inhibition of 11β-hydroxysteroid dehydrogenase (HSD) 1 has been shown to lower intraocular pressure in subjects with ocular hypertension, therefore the compounds could be used to treat glaucoma.

In view of the role of 11β-hydroxysteroid dehydrogenase (HSD) 1 in modulating cortisol levels for interaction with the glucocorticoid receptor, and the known role of excess glucocorticoids in bone loss, the compounds may have beneficial effects in treatment or prevention of osteoporosis.

Stress and/or glucocorticoids have been shown to influence cognitive function, and excess cortisol has been associated with brain neuronal loss or dysfunction. Treatment with an 11β-hydroxysteroid dehydrogenase (HSD) 1 inhibitor may result in amelioration or prevention of cognitive impairment. Such compounds may also be useful in treating anxiety or depression.

The dynamic interaction between the immune system and the HPA (hypothalamopituitary-adrenal) axis is known, and glucocorticoids help balance between cell-mediated responses and humoral responses. The immune reaction is typically biased towards a humoral response in certain disease states, such as tuberculosis, leprosy, and psoriasis. More appropriate would be a cell-based response. An 11β-hydroxysteroid dehydrogenase (HSD) 1 inhibitor would bolster a temporal immune response in association with immunization to ensure that a cell based response would be obtained, and as such could be useful in immunomodulation.

In particular, the compounds according to the invention, including those compounds comprised by the provisos (P1) and (P2), and the physiologically acceptable salts thereof, are suitable for the prevention or treatment of diabetes, particularly type 1 diabetes mellitus, type 2 diabetes mellitus, and diabetic complications.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The compounds according to the invention may also be used in conjunction with other active substances, particularly for the treatment and/or prevention of the diseases and conditions mentioned above. Other active substances which are suitable for such combinations include for example those which potentiate the therapeutic effect of an 11β-hydroxysteroid dehydrogenase (HSD) 1 inhibitor according to the invention with respect to one of the indications mentioned and/or which allow the dosage of an 11β-hydroxysteroid dehydrogenase (HSD) 1 inhibitor according to the invention to be reduced. Therapeutic agents which are suitable for such a combination include, for example, antidiabetic agents such as metformin, sulfonylureas (e.g. glibenclamide, tolbutamide, glimepiride), nateglinide, repaglinide, thiazolidinediones (e.g. rosiglitazone, pioglitazone), SGLT 2 inhibitors (e.g. dapagliflozin, remogliflozin etabonate), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. Sitagliptin, Vildagliptin, Saxagliptin, Alogliptin, BI 1356), alpha2-antagonists, insulin and insulin analogues, GLP-1 and GLP-1 analogues (e.g. exendin-4) or amylin. The list also includes inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase and glucokinase activators, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, SDRIs, axokine, leptin, leptin mimetics, antagonists of the cannabinoid1 receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

The dosage for the combination partners mentioned above is usefully ⅕ of the lowest dose normally recommended up to 1/1 of the normally recommended dose.

Therefore, in another aspect, this invention relates to the use of a compound according to the invention, including those compounds comprised by the provisos (P1) and (P2), or a physiologically acceptable salt of such a compound combined with at least one of the active substances described above as a combination partner, for preparing a pharmaceutical composition which is suitable for the treatment or prevention of diseases or conditions which can be affected by inhibiting the enzyme 11β-hydroxysteroid dehydrogenase (HSD) 1. These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of time.

If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention, including those compounds comprised by the provisos (P1) and (P2), or a physiologically acceptable salt of such a compound and at least one of the active substances described above as combination partners, optionally together with one or more inert carriers and/or diluents.

Thus, for example, a pharmaceutical composition according to the invention comprises a combination of a compound of formula I according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

The Examples that follow are intended to illustrate the present invention without restricting it. The terms "ambient temperature" and "room temperature" are used interchangeably and designate a temperature of about 20° C.

The following abbreviations are used:

| | |
|---|---|
| Ac | acetyl |
| Bu | butyl |
| Et | ethyl |
| Me | methyl |
| Pr | propyl |

Preparation of the Starting Compounds

Example I

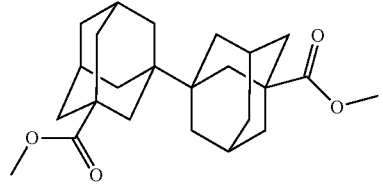

[1,1']Bi[tricyclo[decyl]-3,3'-dicarboxylic acid dimethyl ester

Oleum (ca. 25% SO$_3$, 48 mL) is added to a flask charged with a stir bar and 1,1'-diadamantane (4.0 g) and chilled in an ice bath. The pale brown solution is stirred at 0° C. for 5 min, before HCOOH (5.6 mL, ca. 6.6 g) is dropwise added at 0° C. (gas evolution). The resulting mixture is stirred at 0° C. for 2.5 h and then MeOH (120 mL) is added at 0° C. over a period of 20 min. Stirring is continued at 0° C. for 1 h and at room temperature overnight. The mixture is then added dropwise to an ice-cold saturated aqueous NaHCO$_3$ solution (850 mL) over a period of ca. 2 h. The mixture is extracted with ethyl acetate and the combined organic layers are concentrated under reduced pressure. The crude product is purified by chromatography on silica gel (CH$_2$Cl$_2$/EtOAc 50:1→10:1) to afford the title compound (4.7 g, 47%) as a white (colorless) solid.

Yield: 2.68 g (47% of theory)
$^1$H-NMR (300 MHz, CDCl$_3$): 3.58 (s, 6H), 2.03 (br. s, 4H), 1.79-1.65 (m, 8H), 1.63 (s, 4H), 1.60-1.45 (m, 12H).

Example II

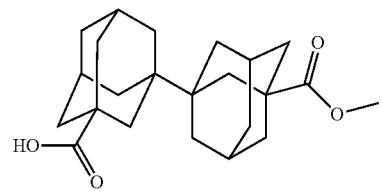

[1,1']Bi[tricyclo[decyl]-3,3'-dicarboxylic acid 3'-methyl ester

Water (5 mL) followed by 0.1 M Ba(OH)$_2$ in MeOH (28.5 mL) is added to a solution of [1,1']bi[tricyclo[decyl]-3,3'-dicarboxylic acid dimethyl ester (1.0 g) in MeOH (22.5 mL) at room temperature. The suspension is stirred at 40° C. for 2 d, before more 0.1 M Ba(OH)$_2$ in MeOH (26 mL, 2.6 mmol) is added and stirring at 40° C. is continued for 2 d. The mixture is acidified with 5% aqueous H$_3$PO$_4$ solution and the resulting mixture is extracted with ethyl acetate. The combined organic layers are filtered through a pad of MgSO$_4$ and concentrated. The residue is purified by chromatography on silica gel (CH$_2$Cl$_2$/MeOH 98:2→95:5) to give the title compound as a white (colorless) solid.

Yield: 0.57 g (59% of theory)
Mass spectrum (APCl$^-$): 371 [M−H]$^-$

Example III

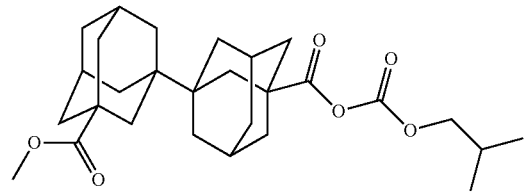

3'-Isobutoxycarbonyloxycarbonyl-[1,1']bi[tricyclo[decyl]-3-carboxylic acid methyl ester N-methyl-morpholine (40 µl) and isobutyl chloroformate (42 µl) are added in succession to an ice-cold solution of [1,1']bi[tricyclo[decyl]-3,3'-dicarboxylic acid 3'-methyl ester (79 mg) in 1,2-dimethoxyethane (5 mL). The resulting mixture is stirred at 0° C. for 40 min and then poured into 5% aqueous H$_3$PO$_4$ solution. The mixture is extracted with ethyl acetate and the combined organic layers are washed with water and concentrated under reduced pressure to afford the crude title compound.

Yield: 109 mg (quantitative)

Example IV

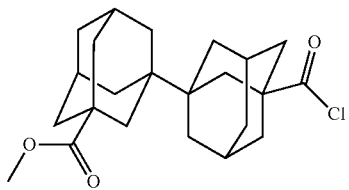

3'-Chlorocarbonyl-[1,1']bi[tricyclo[decyl]-3-carboxylic acid methyl ester

A solution of [1,1']bi[tricyclo[decyl]-3,3'-dicarboxylic acid 3'-methyl ester (300 mg) in $SOCl_2$ (6 mL) is stirred at 50° C. for 2 h. After cooling to ambient temperature, the solution is concentrated under reduced pressure and the residue is evaporated with toluene (10 mL) twice to afford the crude title compound that is used without further purification.

Yield: 300 mg (95% of theory)

The following three procedures, Examples V, VI, and VII, describe the preparation of selected carboxylic amides from the corresponding diadamantyl carboxylic acid or chloride (3'-isobutoxycarbonyloxycarbonyl-[1,1']bi[tricyclo[decyl]-3-carboxylic acid methyl ester may be employed as well). In principal, all amides described may be synthesized using any of these procedures.

Example V

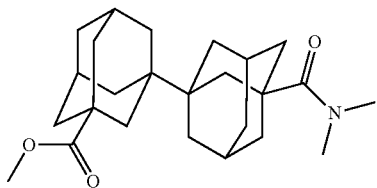

3'-Dimethylcarbamoyl-[1,1']bi[tricyclo[decyl]-3-carboxylic acid methyl ester N,N-Dimethylformamide (5 mL), 2 M $Me_2NH$ solution in tetrahydrofuran (0.28 mL), and $iPr_2NEt$ (0.2 mL) are added consecutively to a flask charged with a stir bar, [1,1']bi[tricyclo[decyl]-3,3'-dicarboxylic acid 3'-methyl ester (140 mg), HCTU [1-(bis-dimethylamino-methylene)-5-chloro-3-oxy-1H-benzotriazol-1-ium-hexafluorophosphate, 240 mg], and 6-chloro-1-hydroxy-benzotriazole (100 mg) at room temperature. The mixture is stirred at room temperature overnight, before saturated aqueous $NaHCO_3$ solution is added. The resulting mixture is extracted with $CH_2Cl_2$, the combined extracts are washed four times with water, dried ($MgSO_4$), and concentrated. The residue is purified by chromatography on silica gel (hexane/ethyl acetate 1:1) to give the title compound as a white solid.

Yield: 120 mg (80% of theory)

Mass spectrum ($APCI^+$): 400 $[M+H]^+$

The following compounds are obtained in analogy to Example V:

(1) 3'-Methylcarbamoyl-[1,1']bi[tricyclo[decyl]-3-carboxylic acid methyl ester

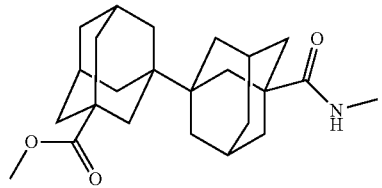

$^1$H-NMR (300 MHz, $CDCl_3$): 5.7-5.6 (br. signal, 1H), 3.65 (s, 3H), 2.80 (d, J=4.8, 3H), 2.19-2.05 (m, 4H), 1.86-1.50 (m, 24H).

$MeNH_2$ is used as nucleophile instead of $Me_2NH$ (2) 3'-Carbamoyl-[1,1']bi[tricyclo[decyl]-3-carboxylic acid methyl ester

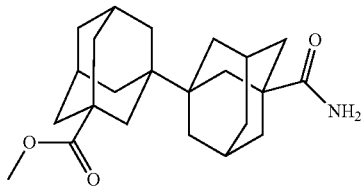

$^1$H-NMR (300 MHz, $CDCl_3$): 5.8-5.6, 5.5-5.3 (2 br. signals, 2H), 3.67 (s, 3H); 2.20-2.09 (m, 4H), 1.90-ca. 1.69 (m, ca. 14H), ca. 1.69-ca. 1.53 (m, ca. 10H).

$NH_4Cl$ combined with $EtNiPr_2$ is used as ammonia source.

Example VI

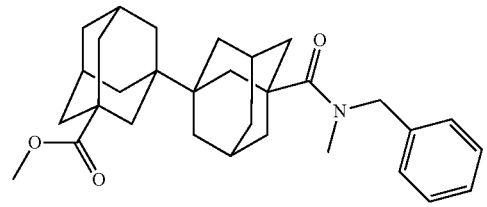

3'-(Benzyl-methyl-carbamoyl)-[1,1']bi[tricyclo[decyl]-3-carboxylic acid methyl ester TBTU [2-(1H-benzotriazol-1-yl)-1,1,3,3-tetramethyluronium tetrafluoroborate; 44 mg] and $EtNiPr_2$ (26 μL) are added to a solution of [1,1']bi[tricyclo[decyl]-3,3'-dicarboxylic acid 3'-methyl ester (50 mg) in N,N-dimethylformamide (2 mL) at room temperature. The mixture is stirred at room temperature for 1 h, before N-benzyl-N-methyl-amine (18 μL) is added. The mixture is stirred at room temperature for 5 h and then concentrated under reduced pressure. The crude product is submitted to ester saponification without further purification.

The following compounds are obtained in analogy to Example VI:

(1) 3'-(Methyl-phenethyl-carbamoyl)-[1,1']bi[tricyclo[decyl]-3-carboxylic acid methyl ester

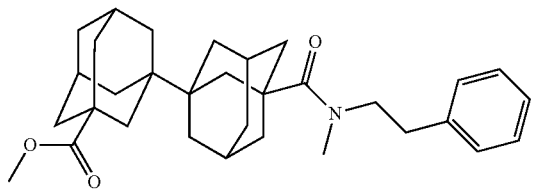

(2) 3'-(4-Methyl-piperazine-1-carbonyl)-[1,1']bi[tricyclo[decyl]-3-carboxylic acid methyl ester

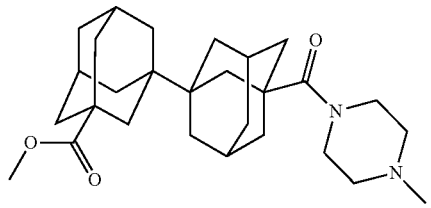

(3) 3'-{[3-(4-Methoxy-phenyl)-propyl]-methyl-carbamoyl}-[1,1']bi[tricyclo[decyl]-3-carboxylic acid methyl ester

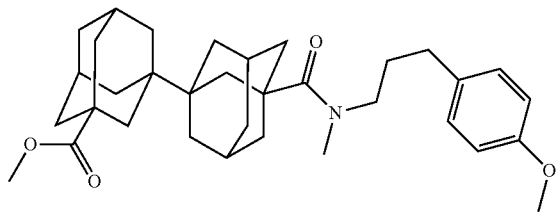

Example VII

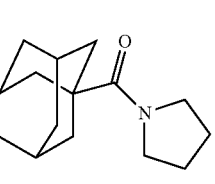

3'-(Benzyl-methyl-carbamoyl)-[1,1']bi[tricyclo[decyl]-3-carboxylic acid methyl ester NEt$_3$ (21 µL) and pyrrolidine (10 mg) are added in succession to a solution of 3'-chlorocarbonyl-[1,1']bi[tricyclo[decyl]-3-carboxylic acid methyl ester (50 mg) in CH$_2$Cl$_2$ (3 mL) at room temperature. After stirring the solution for 3 h, the solvent is evaporated under reduced pressure to give the crude title compound that is submitted to ester saponification without further purification (see Procedure B).

The following compounds are obtained in analogy to Example VII:

(1) 3'-(Morpholine-4-carbonyl)-[1,1']bi[tricyclo[decyl]-3-carboxylic acid methyl ester

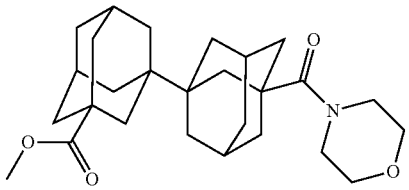

(2) 3'-(2-Hydroxy-ethylcarbamoyl)-[1,1']bi[tricyclo[decyl]-3-carboxylic acid methyl ester

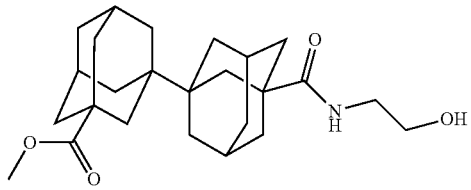

(3) 3'-(Isopropyl-methyl-carbamoyl)-[1,1']bi[tricyclo[decyl]-3-carboxylic acid methyl ester

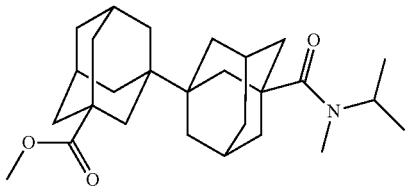

(4) 3'-(Ethyl-methyl-carbamoyl)-[1,1']bi[tricyclo[decyl]-3-carboxylic acid methyl ester

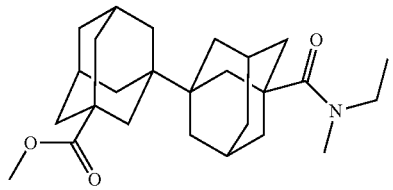

(5) 3'-(Cyano-amino-carbonyl)-[1,1']bi[tricyclo[decyl]-3-carboxylic acid methyl ester

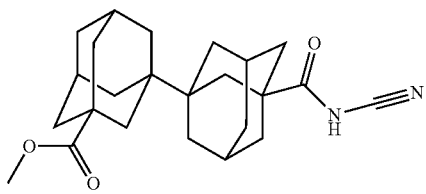

(6) 3'-(Azetidine-1-carbonyl)-[1,1']bi[tricyclo[decyl]-3-carboxylic acid methyl ester

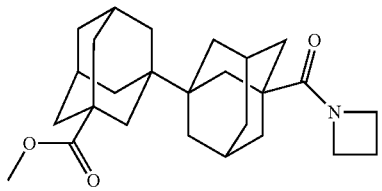

(7) 3'-(Methoxy-methyl-carbamoyl)-[1,1']bi[tricyclo[decyl]-3-carboxylic acid methyl ester

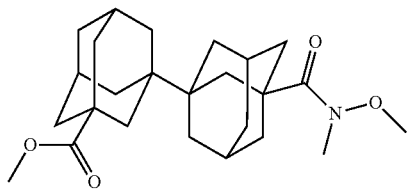

(8) 3'-(2-Hydroxy-phenylcarbamoyl)-[1,1']bi[tricyclo[decyl]-3-carboxylic acid methyl ester

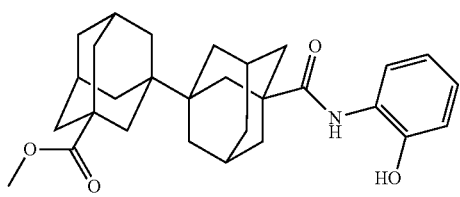

(9) 3'-Phenylcarbamoyl-[1,1']bi[tricyclo[decyl]-3-carboxylic acid methyl ester

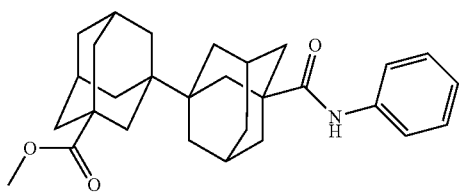

The compound was purified by chromatography on silica gel (cyclohexane/ethyl acetate 1:0→1:1) before submission to saponification.

(10) 3'-(Cyclohexyl-methyl-carbamoyl)-[1,1']bi[tricyclo[decyl]-3-carboxylic acid methyl ester

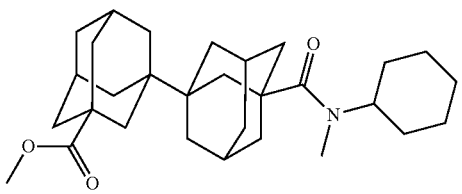

The compound was purified by chromatography on silica gel (cyclohexane/ethyl acetate 1:0→1:1) before submission to saponification.

(11) 3'-(Methyl-phenyl-carbamoyl)-[1,1']bi[tricyclo[decyl]-3-carboxylic acid methyl ester

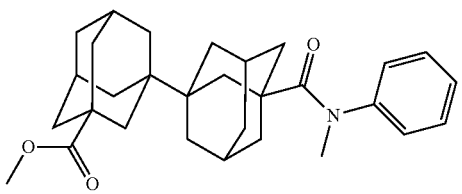

In a departure from the procedure described above the reaction was carried out in toluene at 100° C. (heated with microwave irradiation for 15 min). The compound was purified by chromatography on silica gel (cyclohexane/ethyl acetate 1:0→1:1) before submission to saponification.

(12) 3-[(3'-Methoxycarbonyl-[1,1']bi[tricyclo[decyl]ane-3-carbonyl)-methyl-amino]-piperidine-1-carboxylic acid tert-butyl ester

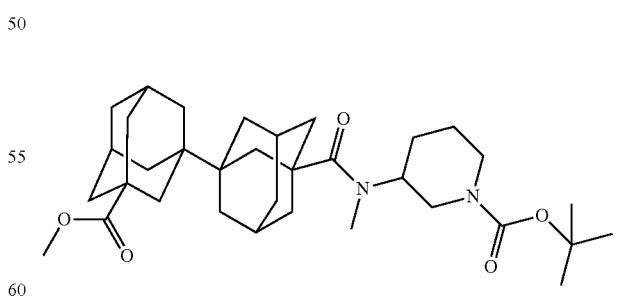

In a departure from the procedure described above the reaction was carried out in toluene at 100° C. (heated with microwave irradiation, 15 min). The compound was purified by chromatography on silica gel (cyclohexane/ethyl acetate 1:0→1:1) before processing it further.

(13) 3'-(2-Methylamino-phenylcarbamoyl)-[1,1']bi[tricyclo[decyl]-3-carboxylic acid methyl ester

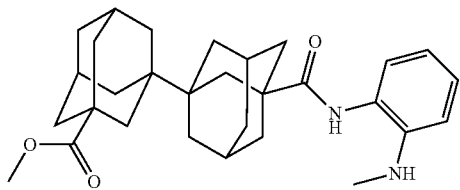

The compound was purified by chromatography on silica gel (cyclohexane/ethyl acetate 1:0→1:1) before submission to saponification.

(14) 3'-[(4-Methoxy-phenyl)-methyl-carbamoyl]-[1,1']bi[tricyclo[decyl]-3-carboxylic acid methyl ester

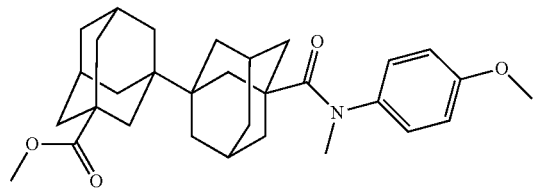

In a departure from the procedure described above the reaction was carried out in toluene at 100° C. (heated with microwave irradiation, 15 min). The compound was purified by chromatography on silica gel (cyclohexane/ethyl acetate 1:0→1:1) before submission to saponification.

(15) 3'-(Biphenyl-4-yl-methyl-carbamoyl)-[1,1']bi[tricyclo[decyl]-3-carboxylic acid methyl ester

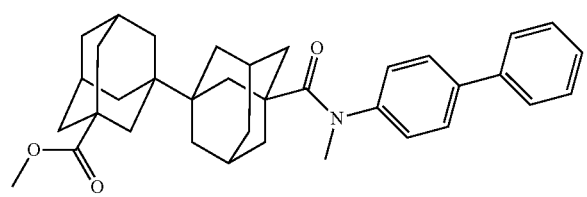

In a departure from the procedure described above the reaction was carried out in toluene at 100° C. (heated with microwave irradiation, 15 min). The compound was purified by chromatography on silica gel (cyclohexane/ethyl acetate 1:0→1:1) before submission to saponification.

(16) 3'-(Cyclohexyl-ethyl-carbamoyl)-[1,1']bi[tricyclo[decyl]-3-carboxylic acid methyl ester

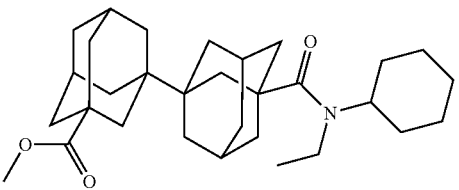

Mass spectrum (ESI$^+$): 482 [M+H]$^+$

In a departure from the procedure described above the reaction was carried out in toluene at 100° C. (heated with microwave irradiation, 15 min). The compound was purified by chromatography on silica gel (cyclohexane/ethyl acetate 1:0→1:1) before submission to saponification.

(17) 3'-[Methyl-(4-phenyl-cyclohexyl)-carbamoyl]-[1,1']bi[tricyclo[decyl]-3-carboxylic acid methyl ester

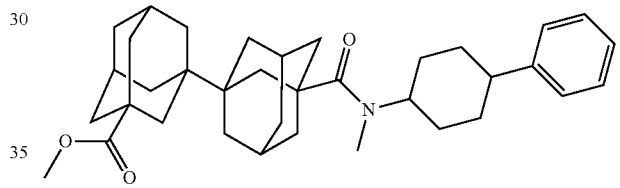

In a departure from the procedure described above the reaction was carried out in toluene at 100° C. (heated with microwave irradiation, 15 min). The compound was purified by chromatography on silica gel (cyclohexane/ethyl acetate 1:0→1:1) before submission to saponification.

(18) 3'[2-(tert-Butoxycarbonylamino-methyl)-phenylcarbamoyl]-[1,1']bi[tricyclo[decyl]-3-carboxylic acid methyl ester

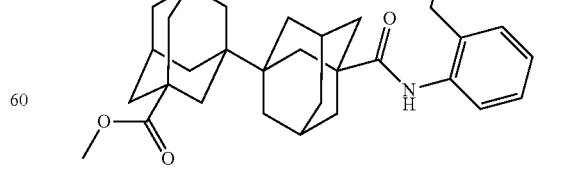

The compound was purified by chromatography on silica gel (cyclohexane/ethyl acetate 1:0→1:1) before submission to saponification.

(19) 3'-[(4-tert-Butyl-cyclohexyl)-methyl-carbamoyl]-[1,1']bi[tricyclo[decyl]-3-carboxylic acid methyl ester

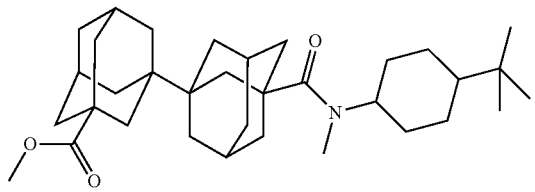

In a departure from the procedure described above the reaction was carried out in toluene at 100° C. (heated with microwave irradiation, 15 min). The compound was purified by chromatography on silica gel (cyclohexane/ethyl acetate 1:0→1:1) before submission to saponification.

(20) 3'-(Cyclohexyl-phenethyl-carbamoyl)-[1,1']bi[tricyclo[decyl]-3-carboxylic acid methyl ester

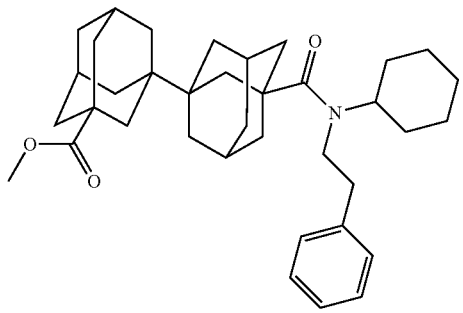

In a departure from the procedure described above the reaction was carried out in toluene at 100° C. (heated with microwave irradiation, 15 min). The compound was purified by chromatography on silica gel (cyclohexane/ethyl acetate 1:0→1:1) before submission to saponification.

(21) 3'-(Cyclopentyl-methyl-carbamoyl)-[1,1']bi[tricyclo[decyl]-3-carboxylic acid methyl ester

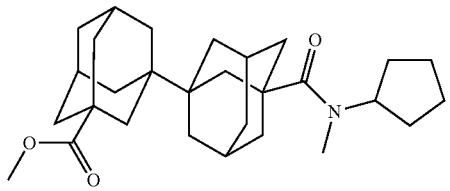

In a departure from the procedure described above the reaction was carried out in toluene at 100° C. (heated with microwave irradiation, 15 min). The compound was purified by chromatography on silica gel (cyclohexane/ethyl acetate 1:0→1:1) before submission to saponification.

(22) 3'-(2-Phenethylamino-phenylcarbamoyl)-[1,1']bi[tricyclo[decyl]-3-carboxylic acid methyl ester

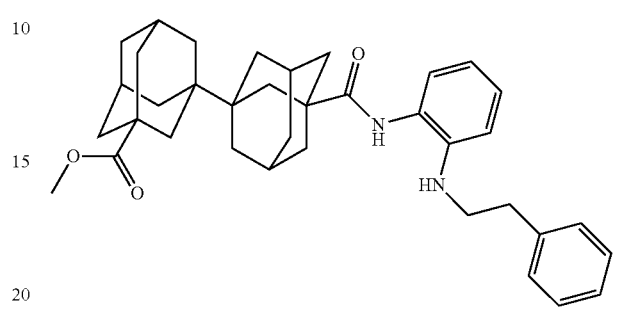

The compound was purified by chromatography on silica gel (cyclohexane/ethyl acetate 1:0→1:1) before submission to saponification.

(23) 3'-(1,3-Dihydro-isoindole-2-carbonyl)-[1,1']bi[tricyclo[decyl]-3-carboxylic acid methyl ester

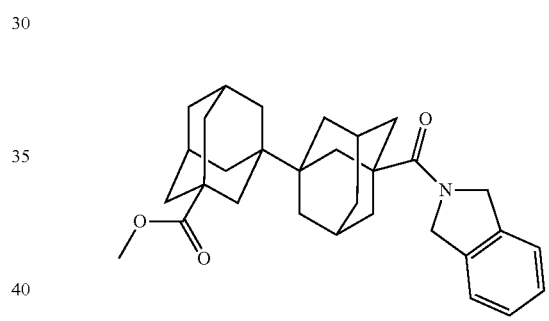

The compound was purified by chromatography on silica gel (cyclohexane/ethyl acetate 1:0→1:1) before submission to saponification.

(24) 3'-(3,4-Dihydro-1H-isoquinoline-2-carbonyl)-[1,1']bi[tricyclo[decyl]-3-carboxylic acid methyl ester

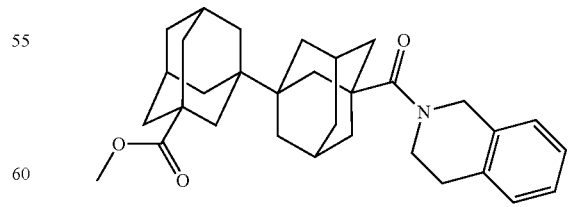

The compound was purified by chromatography on silica gel (cyclohexane/ethyl acetate 1:0→1:1) before submission to saponification.

(25) 3'-(7-Cyano-3,4-dihydro-1H-isoquinoline-2-carbonyl)-[1,1']bi[tricyclo[decyl]-3-carboxylic acid methyl ester

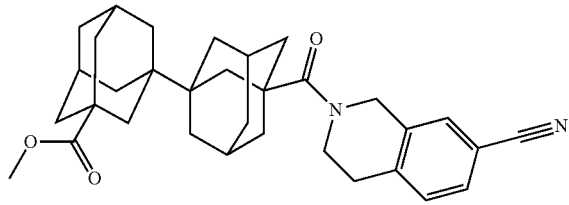

The compound was purified by chromatography on silica gel (cyclohexane/ethyl acetate 1:0→1:1) before submission to saponification.

(26) 3'-[7-(4-Dimethylcarbamoyl-phenoxy)-3,4-dihydro-1H-isoquinoline-2-carbonyl]-[1,1']bi[tricyclo[decyl]-3-carboxylic acid methyl ester

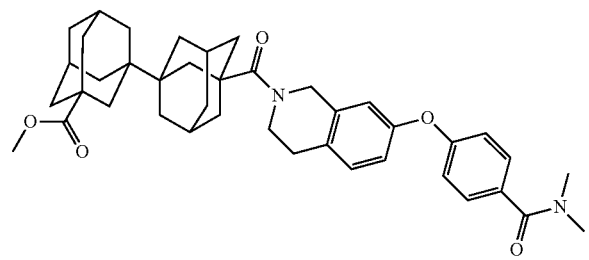

The compound was purified by chromatography on silica gel (cyclohexane/ethyl acetate 1:0→1:1) before submission to saponification.

(27) 3'-(2-Methoxymethyl-pyrrolidine-1-carbonyl)-[1,1']bi[tricyclo[decyl]-3-carboxylic acid methyl ester

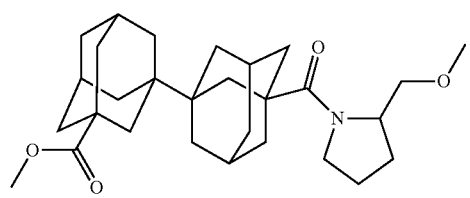

The compound was purified by chromatography on silica gel (cyclohexane/ethyl acetate 1:0→1:1) before submission to saponification.

(28) 3'-(1,2,4,5-Tetrahydro-benzo[d]azepine-3-carbonyl)-[1,1']bi[tricyclo[decyl]-3-carboxylic acid methyl ester

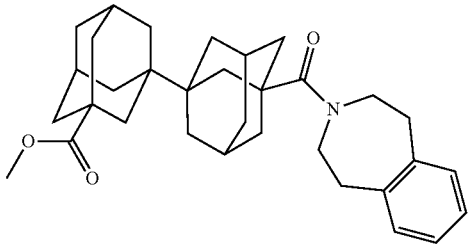

The compound was purified by chromatography on silica gel (cyclohexane/ethyl acetate 1:0→1:1) before submission to saponification.

(29) 3'-(2,3-Dihydro-indole-1-carbonyl)-[1,1']bi[tricyclo[decyl]-3-carboxylic acid methyl ester

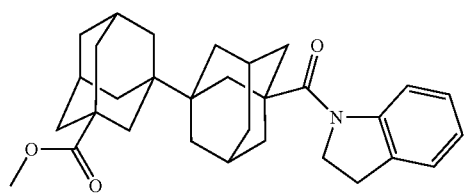

The compound was purified by chromatography on silica gel (cyclohexane/ethyl acetate 1:0→1:1) before submission to saponification.

Example VIII

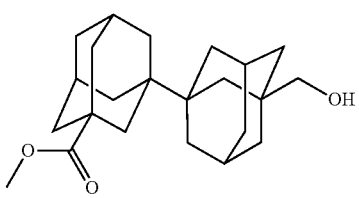

3'-Hydroxymethyl-[1,1']bi[tricyclo[decyl]-3-carboxylic acid methyl ester

NaBH$_4$ (15 mg) is added in one portion to a solution of 3'-isobutoxycarbonyloxycarbonyl-[1,1']bi[tricyclo[decyl]-3-carboxylic acid methyl ester (142 mg, crude product) in EtOH (4 mL) cooled to 0° C. The mixture is stirred at 0° C. for 30 min and then poured into 5% aqueous H$_3$PO$_4$ solution. The resulting mixture is extracted with ethyl acetate and the combined extracts are washed with water and concentrated under reduced pressure. The residue is purified by chromatography on silica gel (CH$_2$Cl$_2$/EtOAc 15:1) to give the title compound as a colorless solid.

Yield: 93 mg (ca. 85% of theory)
Mass spectrum (APCl$^+$): 359 [M+H]$^+$

Example IX

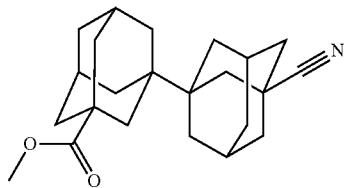

3'-Cyano-[1,1']bi[tricyclo[decyl]-3-carboxylic acid methyl ester (F₃CSO₂)₂O (0.45 mL) is added dropwise to a solution of 3'-carbamoyl-[1,1']bi[tricyclo[decyl]-3-carboxylic acid methyl ester (100 mg) and pyridine (0.43 mL) in 1,4-dioxane (4 mL) at room temperature. The resulting mixture is stirred at room temperature for 1 h and then concentrated. Ethyl acetate and saturated aqueous NaHCO₃ solution are added and the mixture is stirred for 20 min. Then, the mixture is extracted with ethyl acetate and the combined extracts are washed with diluted aqueous NaCl solution and dried (MgSO₄). After removal of the solvent, the crude product is purified by chromatography on silica gel (CH₂Cl₂/EtOAc 1:0→45:1) to afford the title compound as a yellowish solid.

Yield: 78 mg (81% of theory)

Mass spectrum (ESI⁺): 354 [M+H]⁺

Example X

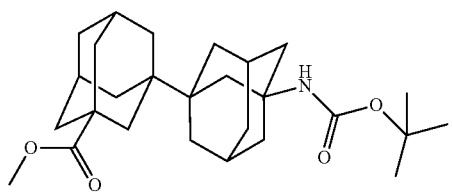

3'-tert-Butoxycarbonylamino-[1,1']bi[tricyclo[decyl]-3-carboxylic acid methyl ester Tetrahydrofuran (8 mL) is added to a mixture of [1,1']bi[tricyclo[decyl]-3,3'-dicarboxylic acid 3'-methyl ester (200 mg), (ᵗBuOCO)₂O (234 mg), NaN₃ (122 mg), nBu₄NBr (70 mg), and Zn(OSO₂CF₃)₂ (38 mg) at room temperature. The milky suspension is stirred at 50° C. for 2 d. Then, saturated aqueous NaHCO₃ solution is added at room temperature (pH value of aqueous layer: 8-9) and the resulting mixture is extracted with EtOAc and CH₂Cl₂. After removal of the solvent, the residue is purified by chromatography on silica gel (hexane/EtOAc 20:1→9:1) to afford the title compound (225 mg, 94%) as a foam-like solid.

Yield: 225 mg (94% of theory)

Mass spectrum (ESI⁺): 444 [M+H]⁺ (very low intensity), 344 [M+H-100]⁺ (low intensity signal)

Example XI

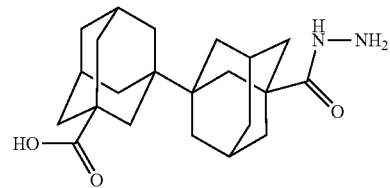

3'-Hydrazinocarbonyl-[1,1']bi[tricyclo[decyl]-3-carboxylic acid

NEt₃ (0.10 mL) and hydrazine hydrate (10 μL) are added in succession to a solution of 3'-chlorocarbonyl-[1,1']bi[tricyclo[decyl]-3-carboxylic acid methyl ester (82 mg) in CH₂Cl₂ (3 mL) at room temperature. The solution is stirred at room temperature overnight and then methanol (3 mL) and 4 M aqueous KOH solution (3 mL) are added. The resulting solution is warmed to 50° C. and stirred at this temperature for 4 h. Then, the solvent is evaporated and the residue is taken up in water and neutralized using 1 M hydrochloric acid. The aqueous phase is extracted with ethyl acetate and the combined extracts are dried (Na₂SO₄). The solvent is evaporated to give the crude title compound that is used without further purification.

Yield: 60 mg (75% of theory)

Example XII

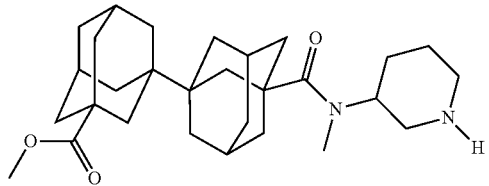

3'-(Methyl-piperidin-3-yl-carbamoyl)-[1,1']bi[tricyclo[decyl]-3-carboxylic acid methyl ester Trifluoroacetic acid (2 mL) is added at room temperature to 3-[(3'-methoxycarbonyl-[1,1']bi[tricyclo[decyl]ane-3-carbonyl)-methyl-amino]-piperidine-1-carboxylic acid tert-butyl ester (60 mg) dissolved in dichloromethane (3 mL). The solution is stirred at room temperature for 3 h. Then, aqueous K₂CO₃ solution is added carefully and the resulting mixture is extracted with ethyl acetate. The combined extracts are concentrated to furnish the crude title compound that is submitted to saponification (Procedure B) without further purification.

Yield: 45 mg (91% of theory)

Mass spectrum (ESI⁺): 469 [M+H]⁺

Example XIII

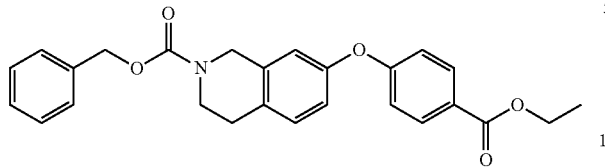

7-(4-Ethoxycarbonyl-phenoxy)-3,4-dihydro-1H-isoquinoline-2-carboxylic acid benzyl ester A flask charged with a stir bar, 7-hydroxy-3,4-dihydro-1H-isoquinoline-2-carboxylic acid benzyl ester (5.00 g), 4-fluoro-benzoic acid ethyl ester (3.27 g), 18-crown-6 (0.47 g), and KF (40% on $Al_2O_3$, 7.50 g) is sparged with argon for 15 min. Then dimethyl sulfoxide (50 mL) is added and the resulting mixture is heated to 140° C. The mixture is stirred at 140° C. for 3 h and then cooled to room temperature. The mixture is poured into diethylether (150 mL) and the resulting mixture is filtered. The filtrate is washed with water and the aqueous washing phase is extracted with diethylether. The combined organic phases are washed with brine, dried ($Na_2SO_4$), and concentrated. The residue is purified by chromatography on silica gel (petrol ether/ethyl acetate 3:1) to furnish the title compound as an oil.

Yield: 4.56 g (60% of theory)

Example XIV

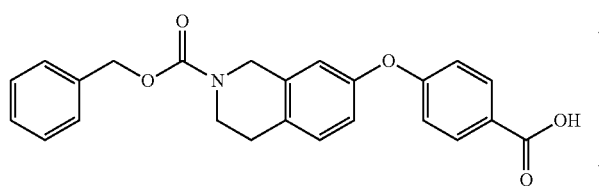

7-(4-Carboxy-phenoxy)-3,4-dihydro-1H-isoquinoline-2-carboxylic acid benzyl ester Sodium hydroxide (0.73 g dissolved in 25 mL water) is added to a solution of 7-(4-ethoxycarbonyl-phenoxy)-3,4-dihydro-1H-isoquinoline-2-carboxylic acid benzyl ester (3.00 g) in ethanol (100 mL). The resulting suspension is stirred at 45° C. overnight. The solution is concentrated and the aqueous residue is adjusted to pH value 2-3 using 1 M hydrochloric acid. Then dichloromethane is added and the mixture is stirred for 10 min. The organic phase is separated and the aqueous phase is extracted with dichloromethane twice. The combined organic phases are dried ($Na_2SO_4$) and concentrated. The residue is purified by chromatography on silica gel (petrol ether/ethyl acetate/acetic acid 50:50:0.5) to furnish the title compound as an oil.

Yield: 2.34 g (83% of theory)

Example XV

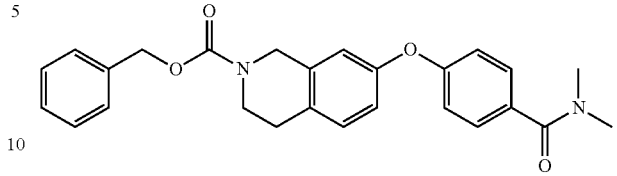

7-(4-Dimethylcarbamoyl-phenoxy)-3,4-dihydro-1H-isoquinoline-2-carboxylic acid benzyl ester 2-(1H-Benzotriazol-1-yl)-1,1,3,3-tetramethyluronium tetrafluoroborate (0.44 g) is added to a solution of 7-(4-carboxy-phenoxy)-3,4-dihydro-1H-isoquinoline-2-carboxylic acid benzyl ester, dimethylamine (2 mol/L in tetrahydrofuran, 0.68 mL), and N-methyl-morpholine (0.41 mL) in tetrahydrofuran (20 mL) chilled in an ice bath. The cooling bath is removed and the resulting mixture is stirred at room temperature for 3 h. Then another portion of dimethylamine (2 mol/L in tetrahydrofuran, 0.70 mL) and 2-(1H-benzotriazol-1-yl)-1,1,3,3-tetramethyluronium tetrafluoroborate (0.20 g) are added and the mixture is further stirred for another 4 h. After adding another portion of dimethylamine (2 mol/L in tetrahydrofuran, 0.30 mL), the mixture ist stirred at room temperature overnight. The mixture is concentrated and the residue is purified by chromatography on silica gel (ethyl acetate) to furnish the title compound.

Yield: 0.45 g (84% of theory)

Example XVI

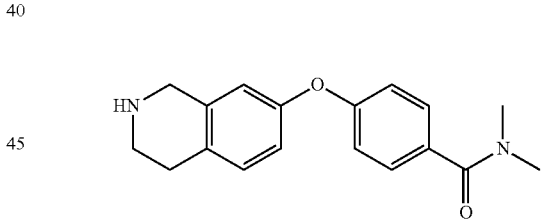

N,N-Dimethyl-4-(1,2,3,4-tetrahydro-isoquinolin-7-yloxy)-benzamide

A mixture of 10% palladium on carbon (1.50 g), 7-(4-dimethylcarbamoyl-phenoxy)-3,4-dihydro-1H-isoquinoline-2-carboxylic acid benzyl ester (2 mL), and ethanol (200 mL) is shaken in hydrogen atmosphere (3 bar) at room temperature for 2 h. Then the catalyst is separated by filtration and the filtrate is concentrated. The residue is purified by chromatography on silica gel (methanol/methanol containing 1% ammionia 1:0→0:1) to furnish the title compound that is precipitated from dioxane with 6 M HCl in dioxane.

Yield (HCl salt of the title compound): 4.20 g (62% of theory)

Preparation of the End Compounds

Procedure A (Described for Example 1, Table 3)

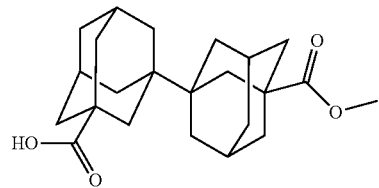

[1,1']Bi[tricyclo[decyl]-3,3'-dicarboxylic acid 3'-methyl ester

LiOH.H$_2$O (197 mg) is added to a mixture of [1,1']bi[tricyclo[decyl]-3,3'-dicarboxylic acid dimethyl ester (302 mg) in 1,4-dioxane (6 mL) and water (1.25 mL) at room temperature. The mixture is stirred at room temperature for 2.5 d. Then, aqueous H$_3$PO$_4$ solution is added and the suspension is filtered. The precipitate is purified by chromatography on silica gel (CHCl$_3$/iPrOH 20:1) to afford the title compound as a colorless solid.
Yield: 60 mg (20% of theory)
Mass spectrum (APCl$^-$): 371 [M−H]$^-$
Alternatively, the compound may be obtained as described in Example II Procedure B (described for Example 12, Table 3)

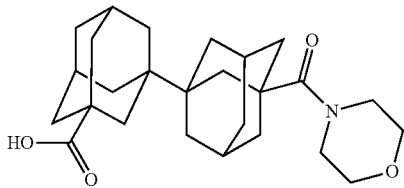

3'-(Morpholine-4-carbonyl)-[1,1']bi[tricyclo[decyl]-3-carboxylic acid

4 M aqueous KOH solution (2 mL) is added to a solution of 3'-(morpholine-4-carbonyl)-[1,1']bi[tricyclo[decyl]-3-carboxylic acid methyl ester [58 mg, crude product from Example VII(1)] in methanol (3 mL) at room temperature. The mixture is heated to 50° C. and stirred at this temperature for 2 h. After cooling to ambient temperature, water is added and the resulting mixture is washed with ethyl acetate. Then, 4 M hydrochloric acid is added to the aqueous phase to precipitate the title compound from the solution. The precipitate is separated by filtration and dried to give the solid title compound.
Yield: 50 mg (87% of theory)
Mass spectrum (ESI$^+$): 428 [M+H]$^+$
Depending on the ease of ester hydrolysis the procedure above is applied as described or slightly varied with regard to temperature and kind and amount of base (LiOH, NaOH, KOH) employed. Saponifications of more stable esters are preferably carried out at 40 to 60° C. and/or using KOH in large excess. In cases in which the purity of the product is not sufficient after precipitation or the compound does not precipitate from the solution, the crude product is purified by chromatography on silica gel (conducted as MPLC, cyclohexane/ethyl acetate or dichloromethane/MeOH) or on reversed phase (conducted as HPLC, MeCN/H$_2$O optionally in the presence of F$_3$CCO$_2$H or NH$_3$).

Procedure C (Described for Example 3, Table 3)

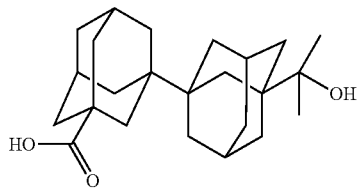

3'-(1-Hydroxy-1-methyl-ethyl)-[1,1']bi[tricyclo[decyl]-3-carboxylic acid

3 M MeMgCl solution in tetrahydrofuran (0.31 mL) is added dropwise to an ice-cold solution of [1,1']bi[tricyclo[decyl]-3,3'-dicarboxylic acid 3'-methyl ester (100 mg) in tetrahydrofuran (5 mL). After stirring the solution at 0° C. for 1 h, additional 3 M MeMgCl solution in tetrahydrofuran (0.1 mL) is added followed by another portion of 3 M MeMgCl after another 30 min (0.1 mL) and 60 min (0.05 mL). The mixture is stirred at 0° C. for further 30 min and at room temperature for 10 h. Then, 5% aqueous H$_3$PO$_4$ solution is added (pH value of aqueous layer: 3-4) and the resulting mixture is extracted with ethyl acetate. The combined organic extracts are filtered through a pad of MgSO$_4$ and concentrated. The residue is purified by chromatography on silica gel (3 runs: CH$_2$Cl$_2$/MeOH 98:2→95:5; CHCl$_3$/MeOH 96:4; CH$_2$Cl$_2$/MeOH 25:1→20:1) to afford the title compound as a white (colorless) solid.
Yield: 62 mg (62% of theory)
Mass spectrum (ESI$^+$): 373 [M+H]$^+$ (very low intensity signal), 355 [M+H−H$_2$O]$^+$ (major signal)

Procedure D (Described for Example 6, Table 3)

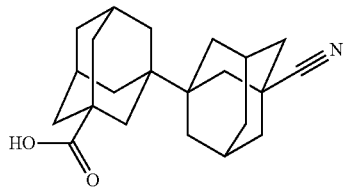

3'-Cyano-[1,1']bi[tricyclo[decyl]-3-carboxylic acid

EtOH (5 mL) followed by water (1.25 mL) is added to a flask charged with a stir bar, 3'-cyano-[1,1']bi[tricyclo[decyl]-3-carboxylic acid methyl ester (97 mg), and KOH (powdered, 154 mg) at room temperature. The solution is stirred at room temperature for 14 d. Then, 0.15 M aqueous H$_3$PO$_4$ solution is added (pH value of aqueous layer: 4-5) and the resulting mixture is extracted with EtOAc and CH$_2$Cl$_2$. The combined extracts are dried (MgSO$_4$) and concentrated under reduced pressure. The remainder is purified by chromatography on silica gel (CH$_2$Cl$_2$/MeOH 20:1) to give the title compound as a white (colorless) solid.

Yield: 85 mg (91% of theory)
Mass spectrum (ESI$^+$): 340 [M+H]$^+$
The reaction may be sped up by increasing the temperature to 40-60° C.

Procedure E (Described for Example 8, Table 3)

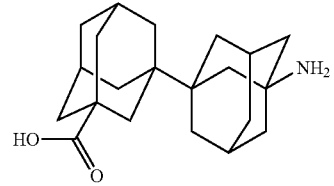

3'-Amino-[1,1']bi[tricyclo[decyl]-3-carboxylic acid

3'-tert-Butoxycarbonylamino-[1,1']bi[tricyclo[decyl]-3-carboxylic acid (155 mg) is dissolved in 4 M HCl solution in 1,4-dioxane (3 mL) at room temperature. The solution is stirred at room temperature overnight. Then, the mixture is concentrated, the residue is evaporated with CH$_2$Cl$_2$ three times and dried to afford the title compound as a white (colorless) solid (HCl salt).

Yield: 132 mg (quantitative, isolated as HCl salt)
Mass spectrum (APCI$^+$): 330 [M+H]$^+$ Procedure F (Described for Example 15, Table 3)

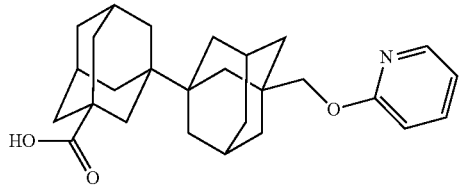

3'-(Pyridin-2-yloxymethyl)-[1,1']bi[tricyclo[decyl]-3-carboxylic acid

NaH (21 mg, 55% in mineral oil) is added to a solution of 3'-hydroxymethyl-[1,1']bi[tricyclo[decyl]-3-carboxylic acid (75 mg) in N-methylpyrrolidinone (3 mL) at room temperature. The mixture is stirred at room temperature for 30 min, before 2-chloropyridine (25 µL) is added and the mixture is warmed to 70° C. After stirring the mixture for 2 h, another portion of 2-chloropyridine (30 µL) is added and the mixture is further stirred at 70° C. overnight. After cooling to room temperature, 1 M aqueous NaOH solution and ethyl acetate are added. The precipitate formed is separated by filtration and dried to yield the title compound as the sodium carboxylate salt.

Yield: 40 mg (41% of theory, isolated as sodium salt of the carboxylic acid function)
Mass spectrum (ESI$^+$): 422 [M+H]$^+$ Procedure G (Described for Example 16, Table 3)

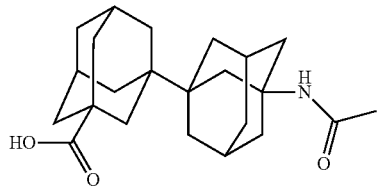

3'-Acetylamino-[1,1']bi[tricyclo[decyl]-3-carboxylic acid

Acetic anhydride (0.19 g) is added to a solution of 3'-amino-[1,1']bi[tricyclo[decyl]-3-carboxylic acid (120 mg) and pyridine (0.15 g) in CH$_2$Cl$_2$ (2 mL) at room temperature. The solution is stirred at room temperature for 2 h. Then, 1 M aqueous NaOH solution is added and the mixture is stirred for additional 10 min. The precipitate formed is separated by filtration and dried to yield the title compound as the sodium carboxylate salt.

Yield: 20 mg (14% of theory, isolated as sodium salt of the carboxylic acid function)
Mass spectrum (ESI$^+$): 372 [M+H]$^+$ Procedure H (Described for Example 21, Table 3)

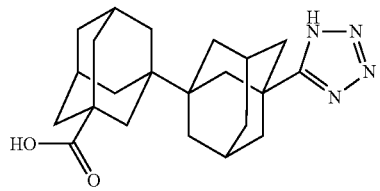

3'-(1H-Tetrazol-5-yl)-[1,1']bi[tricyclo[decyl]-3-carboxylic acid

A mixture of nBu$_4$NF*H$_2$O (39 mg), Me$_3$SiN$_3$ (50 µL), and 3'-cyano-[1,1']bi[tricyclo[decyl]-3-carboxylic acid (85 mg) in a sealed reaction vessel is stirred at 90° C. for 6 h. Then and after each further 8 h period for overall 40 h further portions of Me$_3$SiN$_3$ (50 µL, overall 5×) are added while the mixture is stirred at 90° C. After cooling to ambient temperature, the mixture is diluted with EtOAc and washed with 1 M hydrochloric acid. The solvent is removed and the residue is purified by chromatography on silica gel (CH$_2$Cl$_2$/MeOH 1:0→4:1) to give the title compound.

Yield: 10 mg (10% of theory)
Mass spectrum (ESI$^+$): 383 [M+H]$^+$

Procedure I (Described for Example 24, Table 3)

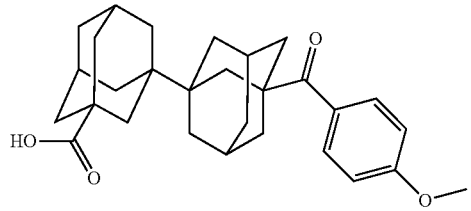

3'-(4-Methoxy-benzoyl)-[1,1']bi[tricyclo[decyl]-3-carboxylic acid

4-Methoxyphenylmagnesium bromide (0.5 mol/L in tetrahydrofuran, 0.27 mL) is added to a solution of 3'-chlorocarbonyl-[1,1']bi[tricyclo[decyl]-3-carboxylic acid methyl ester (51 mg) in toluene (5 mL) cooled to −70° C. (dry ice/acetone) under argon atmosphere. The resulting solution is stirred overnight while warming to room temperature in the cooling bath. Then, 0.1 M hydrochloric acid is added and the resulting mixture is extracted with ethyl acetate. The combined extracts are washed with water and concentrated. The residue is taken up in a 1:1 mixture of methanol and tetrahydrofuran (4 mL) and treated with 4 M aqueous KOH solution (3 mL). After stirring the solution overnight at room temperature, the solution is acidified with 4 M hydrochloric acid and the resultant solution is extracted with ethyl acetate. The combined extracts are dried (Na$_2$SO$_4$) and concentrated under reduced pressure. The residue is purified by chromatography on silica gel (cyclohexane/ethyl acetate 4:1→1:1) to afford the title compound.

Yield: 15 mg (25% of theory)

Mass spectrum (ESI$^+$): 449 [M+H]$^+$

Procedure J (Described for Example 26, Table 3)

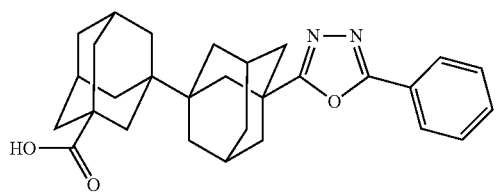

3'45-Phenyl-[1,3,4]oxadiazol-2-yl)-[1,1']bi[tricyclo[decyl]-3-carboxylic acid

A mixture of 3'-hydrazinocarbonyl-[1,1']bi[tricyclo[decyl]-3-carboxylic acid (60 mg), trimethoxymethyl-benzene (31 mg), and p-toluene-sulfonic acid hydrate (31 mg) in toluene (1 mL) is stirred at 100° C. for 6 h. After cooling the solution to room temperature, water is added and the resulting mixture is extracted with ethyl acetate. The combined extracts are dried (Na$_2$SO$_4$) and the solvent is evaporated. The residue is purified by HPLC on reversed phase (acetonitrile/water) to afford the title compound.

Yield: 14 mg (19% of theory)

Mass spectrum (ESI$^-$): 457 [M−H]$^-$

Procedure K (Described for Example 27, Table 3)

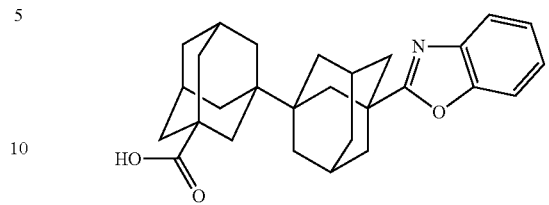

3'-Benzooxazol-2-yl-[1,1']bi[tricyclo[decyl]-3-carboxylic acid

4 M aqueous KOH solution (2 mL) is added to a solution of 3'-(2-hydroxy-phenylcarbamoyl)-[1,1']bi[tricyclo[decyl]-3-carboxylic acid methyl ester (80 mg) in methanol (3 mL). The resulting solution is stirred at 50° C. for 4 h. After cooling to room temperature, the solution is concentrated and the residue is diluted with water and acidified using 1 M hydrochloric acid. The resulting mixture is extracted with ethyl acetate and the combined extracts are concentrated. The residue is taken up in acetic acid (4 mL) and the resulting solution is stirred at 100° C. overnight. Then, the solution is concentrated and the residue is purified by chromatography on silica gel (dichloromethane/methanol 1:0→9:1) to afford the title compound.

Yield: 30 mg (40% of theory)

Mass spectrum (ESI$^+$): 432 [M+H]$^+$

Procedure L (Described for Example 50, Table 3)

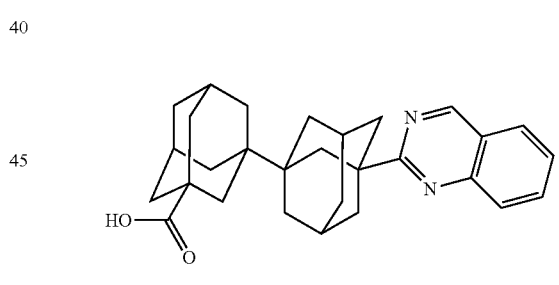

3'-Quinazolin-2-yl-[1,1']bi[tricyclo[decyl]-3-carboxylic acid

A mixture of 3'-(1,4-dihydro-quinazolin-2-yl) [1,1']bi[tricyclo[decyl]-3-carboxylic acid (60 mg), MnO$_2$ (52 mg), and toluene (3 mL) is stirred at 110° C. for 8 h. After cooling to room temperature, the mixture is filtered over Celite and the filtrate is concentrated. The residue is purified by chromatography on silica gel (dichloromethane/methanol 1:0→9:1) to afford the title compound.

Yield: 10 mg (19% of theory)

Mass spectrum (ESI$^+$): 443 [M+H]$^+$

TABLE 3

Compilation of compounds prepared in analogy to the aforementioned procedures

| Example | Name and Structure | Prepared in analogy to procedure | Characteristic data |
| --- | --- | --- | --- |
| 1 | [1,1']Bi[tricyclo[decyl]-3,3'-dicarboxylic acid 3'-methyl ester | A | Mass spectrum (APCl⁻): 371 [M − H]⁻ |
| 2 | 3'-Methylcarbamoyl-[1,1']bi[tricyclo[decyl]-3-carboxylic acid | B | Mass spectrum (ESI⁺): 372 [M + H]⁺ |
| 3 | 3'-(1-Hydroxy-1-methyl-ethyl)-[1,1']bi[tricyclo[decyl]-3-carboxylic acid | C | Mass spectrum (ESI⁺): 373 [M + H]⁺ (very low intensity signal), 355 [M + H − H$_2$O]⁺ (major signal) |
| 4 | 3'-Dimethylcarbamoyl-[1,1']bi[tricyclo [decyl] 3-carboxylic acid | B | Mass spectrum (APCl⁺): 386 [M + H]⁺ |
| 5 | 3'-Carbamoyl-[1,1']bi[tricyclo[decyl]-3-carboxylic acid | B | Mass spectrum (ESI⁺): 358 [M + H]⁺ |

TABLE 3-continued

Compilation of compounds prepared in analogy to the aforementioned procedures

| Example | Name and Structure | Prepared in analogy to procedure | Characteristic data |
|---|---|---|---|
| 6 | 3'-Cyano-[1,1']bi[tricyclo[decyl]-3-carboxylic acid | D | Mass spectrum (ESI$^+$): 340 [M + H]$^+$ |
| 7 | 3'-tert-Butoxycarbonylamino-[1,1']bi[tricyclo[decyl]-3-carboxylic acid | B | Mass spectrum (APCI$^-$): 428 [M − H]$^-$ |
| 8 | 3'-Amino-[1,1']bi[tricyclo[decyl]-3-carboxylic acid<br><br>isolated as HCl salt | E | Mass spectrum (APCI$^+$): 330 [M + H]$^+$ |
| 9 | 3'-(Benzyl-methyl-carbamoyl)-[1,1']bi[tricyclo[decyl]-3-carboxylic acid<br><br>isolated as sodium carboxylate | B | Mass spectrum (ESI$^+$): 462 [M + H]$^+$ |
| 10 | 3'-(Methyl-phenethyl-carbamoyl)-[1,1']bi[tricyclo[decyl]-3-carboxylic acid | B | Mass spectrum (ESI$^+$): 476 [M + H]$^+$ |

TABLE 3-continued

Compilation of compounds prepared in analogy to the aforementioned procedures

| Example | Name and Structure | Prepared in analogy to procedure | Characteristic data |
| --- | --- | --- | --- |
| 11 | 3'-(Pyrrolidine-1-carbonyl)[1,1']bi[tricyclo[decyl]-3-carboxylic acid 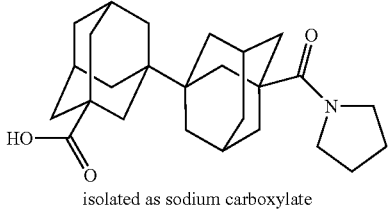 isolated as sodium carboxylate | B | Mass spectrum (ESI$^+$): 412 [M + H]$^+$ |
| 12 | 3'-(Morpholine-4-carbonyl)-[1,1']bi[tricyclo[decyl]-3-carboxylic acid 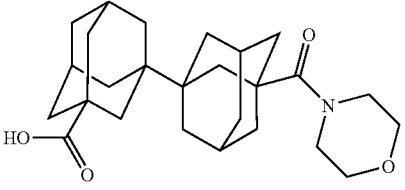 | B | Mass spectrum (ESI$^+$): 428 [M + H]$^+$ |
| 13 | 3'-(2-Hydroxy-ethylcarbamoyl)[1,1']bi[tricyclo[decyl]-3-carboxylic acid 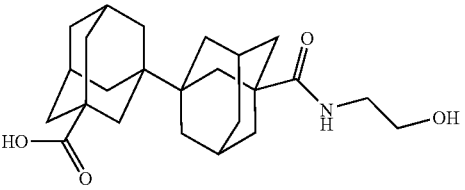 | B | Mass spectrum (ESI$^-$): 466 [M + HCOO]$^-$ |
| 14 | 3'-Hydroxymethyl-[1,1']bi[tricyclo[decyl]-3-carboxylic acid 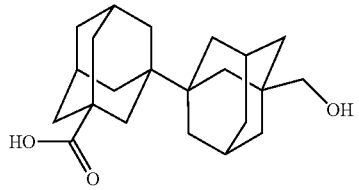 | B | Mass spectrum (ESI$^+$): 345 [M + H]$^+$ |
| 15 | 3'-(Pyridin-2-yloxymethyl)-[1,1']bi[tricyclo[decyl]-3-carboxylic acid 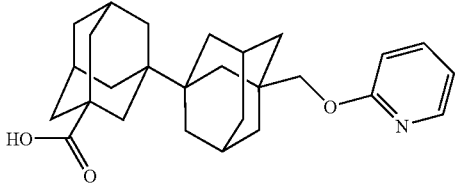 isolated as sodium carboxylate | F | Mass spectrum (ESI$^+$): 422 [M + H]$^+$ |

TABLE 3-continued

Compilation of compounds prepared in analogy to the aforementioned procedures

| Example | Name and Structure | Prepared in analogy to procedure | Characteristic data |
|---|---|---|---|
| 16 | 3'-Acetylamino-[1,1']bi[tricyclo[decyl]-3-carboxylic acid<br><br>isolated as sodium carboxylate | G | Mass spectrum (ESI$^+$): 372 [M + H]$^+$ |
| 17 | 3'-(Isopropyl-methyl-carbamoyl)[1,1']bi[tricyclo[decyl]-3-carboxylic acid | B | Mass spectrum (ESI$^+$): 414 [M + H]$^+$ |
| 18 | 3'-(Ethyl-methyl-carbamoyl)-[1,1']bi[tricyclo[decyl]-3-carboxylic acid | B | Mass spectrum (ESI$^+$): 400 [M + H]$^+$ |
| 19 | 3'-Cyanoaminocarbonyl-[1,1']bi[tricyclo[decyl]-3-carboxylic acid | B | Mass spectrum (ESI$^-$): 381 [M − H]$^-$ |
| 20 | 3'-(Azetidine-1-carbonyl)-[1,1']bi[tricyclo[decyl]-3-carboxylic acid | B | Mass spectrum (ESI$^+$): 398 [M + H]$^+$ |

TABLE 3-continued

Compilation of compounds prepared in analogy to the aforementioned procedures

| Example | Name and Structure | Prepared in analogy to procedure | Characteristic data |
|---------|-------------------|----------------------------------|---------------------|
| 21 | 3'-(1H-Tetrazol-5-yl)-[1,1']bi[tricyclo[decyl]-3-carboxylic acid | H | Mass spectrum (ESI$^+$): 383 [M + H]$^+$ |
| 22 | 3'-(4-Methyl-piperazine-1-carbonyl)-[1,1']bi[tricyclo[decyl]-3-carboxylic acid<br><br>isolated as HCl salt | B | Mass spectrum (ESI$^+$): 441 [M + H]$^+$ |
| 23 | 3'-{[3-(4-Methoxy-phenyl)-propyl]-methyl-carbamoyl}-[1,1']bi[tricyclo[decyl]-3-carboxylic acid | B | Mass spectrum (ESI$^+$): 520 [M + H]$^+$ |
| 24 | 3'-(4-Methoxy-benzoyl)-[1,1'9bi[tricyclo[decyl]-3-carboxylic acid | I | Mass spectrum (ESI$^+$): 449 [M + H]$^+$ |
| 25 | 3'-Methoxycarbamoyl-[1,1']bi[tricyclo[decyl]-3-carboxylic acid | B | Mass spectrum (ESI$^+$): 402 [M + H]$^+$ |

TABLE 3-continued

Compilation of compounds prepared in analogy to the aforementioned procedures

| Example | Name and Structure | Prepared in analogy to procedure | Characteristic data |
|---|---|---|---|
| 26 | 3'-(5-Phenyl-[1,3,4]oxadiazol-2-yl)-[1,1']bi[tricyclo[decyl]-3-carboxylic acid | J | Mass spectrum (ESI$^-$): 457 [M – H]$^-$ |
| 27 | 3'-Benzooxazol-2-yl-[1,1']bi[tricyclo[decyl]-3-carboxylic acid | K | Mass spectrum (ESI$^+$): 432 [M + H]$^+$ |
| 28 | 3'-Phenylcarbamoyl-[1,1']bi[tricyclo[decyl]-3-carboxylic acid | B | Mass spectrum (ESI$^-$): 432 [M – H]$^-$ |
| 29 | 3'-(Cyclohexyl-methyl-carbamoyl)-[1,1']bi[tricyclo[decyl]-3-carboxylic acid | B | Mass spectrum (ESI$^-$): 452 [M – H]$^-$ |
| 30 | 3'-(Methyl-phenyl-carbamoyl)-[1,1']bi[tricyclo[decyl]-3-carboxylic acid | B | Mass spectrum (ESI$^-$): 446 [M – H]$^-$ |

TABLE 3-continued

*Compilation of compounds prepared in analogy to the aforementioned procedures*

| Example | Name and Structure | Prepared in analogy to procedure | Characteristic data |
|---|---|---|---|
| 31 | 3'-(Cyclohexyl-methyl-carbamoyl)-[1,1']bi[tricyclo[decyl]-3-carboxylic acid<br><br>The compound was isolated as HCl salt | B | Mass spectrum (ESI$^+$): 455 [M + H]$^+$ |
| 32 | 3'-(1-Methyl-1H-benzoimidazol-2-yl)-[1,1']bi[tricyclo[decyl]-3-carboxylic acid | K | Mass spectrum (ESI$^+$): 445 [M + H]$^+$ |
| 33 | 3'-[(4-Methoxy-phenyl)-methyl-carbamoyl]-[1,1']bi[tricyclo[decyl]-3-carboxylic acid<br><br>The compound was isolated as the potassium carboxylate | B | Mass spectrum (ESI$^-$): 476 [M − H]$^-$ |
| 34 | 3'-(Biphenyl-4-yl-methyl-carbamoyl)-[1,1']bi[tricyclo[decyl]-3-carboxylic acid | B | Mass spectrum (ESI$^-$): 522 [M − H]$^-$ |
| 35 | 3'-(Cyclohexyl-ethyl-carbamoyl)-[1,1']bi[tricyclo[decyl]-3-carboxylic acid | B | Mass spectrum (ESI$^-$): 466 [M − H]$^-$ |

TABLE 3-continued

Compilation of compounds prepared in analogy to the aforementioned procedures

| Example | Name and Structure | Prepared in analogy to procedure | Characteristic data |
|---|---|---|---|
| 36 | 3'-[Methyl-(4-phenyl-cyclohexyl)-carbamoyl]-[1,1']bi[tricyclo[decyl]-3-carboxylic acid | B | Mass spectrum (ESI−): 528 [M − H]− |
| 37 | 3'-(1,4-Dihydro-quinazolin-2-yl)-[1,1']bi[tricyclo[decyl]-3-carboxylic acid<br><br>The compound was isolated as HCl salt | K | Mass spectrum (ESI+): 445 [M + H]+ |
| 38 | 3'-[(4-tert-Butyl-cyclohexyl)-methyl-carbamoyl]-[1,1']bi[tricyclo[decyl]-3-carboxylic acid | B | Mass spectrum (ESI−): 508 [M − H]− |
| 39 | 3'-(Cyclohexyl-phenethyl-carbamoyl)-[1,1']bi[tricyclo[decyl]-3-carboxylic acid | B | Mass spectrum (ESI−): 542 [M − H]− |
| 40 | 3'-(Cyclopentyl-methyl-carbamoyl)-[1,1']bi[tricyclo[decyl]-3-carboxylic acid | B | Mass spectrum (ESI−): 438 [M − H]− |

TABLE 3-continued

Compilation of compounds prepared in analogy to the aforementioned procedures

| Example | Name and Structure | Prepared in analogy to procedure | Characteristic data |
|---|---|---|---|
| 41 | 3'-(1-Phenethyl-1H-benzoimidazol-2-yl)-[1,1']bi[tricyclo[decyl]-3-carboxylic acid | K | Mass spectrum (ESI$^+$): 533 [M + H]$^+$ |
| 42 | 3'-(1,3-Dihydro-isoindole-2-carbonyl)-[1,1']bi[tricyclo[decyl]-3-carboxylic acid | B | Mass spectrum (ESI$^-$): 504 [M + HCOO]$^-$ |
| 43 | 3'-(3,4-Dihydro-1H-isoquinoline-2-carbonyl)-[1,1']bi[tricyclo[decyl]-3-carboxylic acid | B | Mass spectrum (ESI$^-$): 472 [M − H]$^-$ |
| 44 | 3'-(7-Cyano-3,4-dihydro-1H-isoquinoline-2-carbonyl)-[1,1']bi[tricyclo[decyl]-3-carboxylic acid | B | Mass spectrum (ESI$^-$): 497 [M − H]$^-$ |

TABLE 3-continued

Compilation of compounds prepared in analogy to the aforementioned procedures

| Example | Name and Structure | Prepared in analogy to procedure | Characteristic data |
|---|---|---|---|
| 45 | 3'-[7-(4-Carboxy-phenoxy)-3,4-dihydro-1H isoquinoline-2-carbonyl]-[1,1']bi[tricyclo[decyl]-3-carboxylic acid | B | Mass spectrum (ESI$^-$): 608 [M − H]$^-$ | was obtained from 3'-[7-(4-dimethylcarbamoyl-phenoxy)-3,4-dihydro-1H isoquinoline-2-carbonyl]-[1,1']bi[tricyclo[decyl]-3-carboxylic acid methyl ester in a mixture with Example 46 that was chromatographically resolved

| 46 | 3'-[7-(4-Dimethylcarbamoyl-phenoxy)-3,4-dihydro-1H-isoquinoline-2-carbonyl]-[1,1']bi[tricyclo[decyl]-3-carboxylic acid | B | Mass spectrum (ESI$^-$): 635 [M − H]$^-$ | was obtained in a mixture with Example 45 that was chromatographically resolved

| 47 | 3'-(2-Methoxymethyl-pyrrolidine-1-carbonyl)[1,1']bi[tricyclo[decyl]-3-carboxylic acid | B | Mass spectrum (ESI$^-$): 454 [M − H]$^-$ |

TABLE 3-continued

Compilation of compounds prepared in analogy to the aforementioned procedures

| Example | Name and Structure | Prepared in analogy to procedure | Characteristic data |
|---|---|---|---|
| 48 | 3'-(1,2,4,5-Tetrahydro-benzo[d]azepine-3-carbonyl)-[1,1']bi[tricyclo[decyl]-3-carboxylic acid | B | Mass spectrum (ESI$^-$): 486 [M − H]$^-$ |
| 49 | 3'-(6-Bromo-3,4-dihydro-1H-isoquinoline-2-carbonyl)-[1,1']bi[tricyclo[decyl]-3-carboxylic acid | B | Mass spectrum (ESI$^-$): 550/552 (Br) [M − H]$^-$ |
| 50 | 3'-Quinazolin-2-yl-[1,1']bi[tricyclo[decyl]-3-carboxylic acid | L | Mass spectrum (ESI$^+$): 443 [M + H]$^+$ |
| 51 | 3'-(2,3-Dihydro-indole-1-carbonyl)[1,1']bi[tricyclo[decyl]-3-carboxylic acid | B | Mass spectrum (ESI$^+$): 460 [M + H]$^+$ |

Some examples of formulations will now be described in which the term "active substance" denotes one or more compounds according to the invention, including the salts thereof. In the case of one of the combinations with one or additional active substances as described previously, the term "active substance" also includes the additional active substances.

Example A

Tablets Containing 100 Mg of Active Substance

Composition:
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.
Weight of tablet: 220 mg
Diameter: 10 mm, biplanar, facetted on both sides and notched on one side.

Example B

Tablets Containing 150 Mg of Active Substance

Composition:
1 tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.
Weight of tablet: 300 mg
die: 10 mm, flat

Example C

Hard Gelatine Capsules Containing 150 Mg of Active Substance

Composition:
1 capsule contains:

| | |
|---|---|
| active substance | 150.0 mg |
| corn starch (dried) | approx. 180.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.
Capsule filling: approx. 320 mg
Capsule shell: size 1 hard gelatine capsule.

Example D

Suppositories Containing 150 Mg of Active Substance

Composition:
1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

Example E

Ampoules Containing 10 Mg Active Substance

Composition:

| | |
|---|---|
| active substance | 10.0 mg |
| 0.01N hydrochloric acid | q.s. |
| double-distilled water | ad 2.0 mL |

Preparation:

The active substance is dissolved in the necessary amount of 0.01 N HCl, made isotonic with common salt, filtered sterile and transferred into 2 mL ampoules.

Example F

Ampoules Containing 50 Mg of Active Substance

Composition:

| | |
|---|---|
| active substance | 50.0 mg |
| 0.01N hydrochloric acid | q.s. |
| double-distilled water ad | 10.0 mL |

Preparation:

The active substance is dissolved in the necessary amount of 0.01 N HCl, made isotonic with common salt, filtered sterile and transferred into 10 mL ampoules.

The invention claimed is:
1. A compound of formula (I)

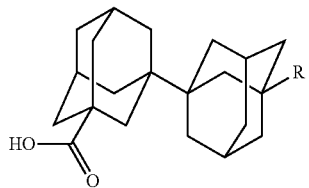

wherein
R denotes hydrogen, halogen, $C_{1-10}$alkyl, $C_{2-6}$-alkenyl, $C_{2-6}$-alkynyl, $C_{3-6}$-cycloalkyl, hydroxy, cyano, amino, pyrrolidin-1-yl, piperidin-1-yl, nitro, sulfanyl, (het)aryl, aminocarbonyl, cyanoaminocarbonyl, azetidin-1-ylcarbonyl, pyrrolidin-1-ylcarbonyl, piperidin-1-ylcarbonyl, or morpholin-4-ylcarbonyl,
wherein each alkyl, cycloalkyl, cycloheteroalkyl, alkenyl, and alkynyl group is optionally mono- or polysubstituted independently of each other with fluorine, $C_{1-4}$-alkyl, $C_{3-6}$-cycloalkyl, hydroxy, $C_{1-4}$-alkoxy, (het)aryloxy, $C_{1-4}$-alkylsulfanyl, $C_{1-4}$-alkylsulfinyl, $C_{1-4}$-alkylsulfonyl, amino, $C_{1-4}$-alkylamino, di-($C_{1-4}$-alkyl)amino, N—$C_{1-3}$-alkoxy-N—$C_{1-3}$-alkyl-amino, azetidin-1-yl, pyrrolidin-1-yl, piperidin-1-yl, $C_{1-4}$-alkylcarbonylamino, N—($C_{1-4}$-alkylcarbonyl)-N—$C_{1-3}$-alkyl-amino, (het)arylcarbonylamino, N-[(het)arylcarbonyl]-N—$C_{1-3}$-alkyl-amino, cyano, carboxy, $C_{1-4}$-alkoxycarbonyl, aminocarbonyl, $C_{1-4}$-alkyl-aminocarbonyl, di-($C_{1-4}$-alkyl)aminocarbonyl, (het)arylaminocarbonyl, N-((het)aryl)-N—($C_{1-3}$-alkyl)-aminocarbonyl, or (het)aryl, while each alkyl, cycloalkyl, and cycloheteroalkyl group is optionally mono- or polysubstituted with fluorine and/or mono- or disubstituted independently of each other with $C_{1-3}$-alkyl, hydroxy, $C_{1-3}$-alkyloxy, cyano, carboxy, $C_{1-3}$-alkyloxycarbonyl, aminocarbonyl, methylaminocarbonyl, dimethylaminocarbonyl, amino, acetylamino, or (het)aryl,
wherein in each above-mentioned alkyl, cycloalkyl, cycloheteroalkyl, alkenyl, and alkynyl group optionally one to three $CH_2$ groups are replaced independently of each other by $NR^N$, O, S, SO, $SO_2$, and CO, while if one of these groups happens to be incorporated more than once they are not directly attached to each other,
$R^N$ denotes hydrogen, $C_{1-6}$-alkyl, $C_{3-6}$-alkenyl, $C_{3-6}$-alkynyl, $C_{3-6}$-cycloalkyl, (het)aryl, $C_{1-4}$-alkylcarbonyl, aminocarbonyl, $C_{1-4}$-alkyloxycarbonyl, $C_{1-4}$-alkylaminocarbonyl, di-($C_{1-3}$-alkyl)amino-carbonyl, $C_{1-4}$-alkylsulfonyl, (het)arylcarbonyl, (het)arylaminocarbonyl, or (het)arylsulfonyl,
wherein each alkyl, cycloalkyl, alkenyl, and alkynyl group is optionally mono- or polysubstituted with fluorine and optionally monosubstituted with hydroxy, $C_{1-4}$-alkoxy, $C_{1-4}$-alkylsulfanyl, $C_{1-4}$-alkylsulfinyl, $C_{1-4}$-alkylsulfonyl, amino, $C_{1-4}$-alkylamino, di-($C_{1-4}$-alkyl) amino, $C_{1-4}$-alkylcarbonylamino, cyano, carboxy, $C_{1-4}$-alkoxycarbonyl, aminocarbonyl, $C_{1-4}$-alkylaminocarbonyl, di-($C_{1-4}$-alkyl)aminocarbonyl, or (het)aryl,
(het)aryl is selected from the group consisting of phenyl, naphthyl, pyrrolyl, furanyl, thienyl, tetrazolyl, pyridyl, indolyl, benzofuranyl, benzothiophenyl, quinolinyl, and isoquinolinyl, or
selected from the group consisting of pyrrolyl, furanyl, thienyl, and pyridyl in all of which 1 or 2 CH-groups are replaced by N, or
selected from the group consisting of indolyl, benzofuranyl, benzothiophenyl, quinolinyl, and isoquinolinyl, in all of which 1 to 3 CH-groups are replaced by N, or
selected from the group consisting of 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzo-furanyl, 2,3-dihydro-2-oxo-1H-benzimidazolyl, 2,3-dihydro-2-oxo-benzoxazolyl, 1,2-di-hydro-2-oxo-quinolinyl, 1,4-dihydro-4-oxo-quino-linyl, 1,2-dihydro-1-oxo-isoquinolinyl, 1,4-dihydro-4-oxo-cinnolinyl, 1,2-dihydro-2-oxo-quinazolinyl, 1,4-dihydro-4-oxo-quina-zolinyl, 1,2,3,4-tetrahydro-2,4-dioxo-quinazolinyl, 1,2-dihydro-2-oxoquinoxalinyl, 1,2,3,4-tetrahydro-3-oxo-quinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, coumarinyl, 2,3-dihydro-benzo[1,4]dioxinyl, and 3,4-dihydro-3-oxo-2H-benzo[1,4]oxazinyl, dihydroquinazolinyl, 3,4-dihydro-1H-isoquinolin-2-yl-carbonyl, 1,3-dihydro-isoindol-2-yl-carbonyl, 2,3-dihydro-indol-1-yl-carbonyl, and 1,2,4,5-tetrahydro-benzo[d]azepin-3-yl-carbonyl,
wherein the above-mentioned (het)aryl rings are optionally mono- or polyfluorinated and are optionally substituted with 1, 2, 3, or 4 substituents selected independently of each other from $L^1$,
$L^1$ denotes halogen, $C_{1-3}$-alkyl, difluoromethyl, trifluoromethyl, cyano, nitro, amino, $C_{1-3}$-alkylamino, di-($C_{1-3}$-alkyl)amino, $C_{1-3}$-alkylcarbonylamino, $C_{1-3}$-alkylsulfonylamino, carboxy, $C_{1-4}$-alkyloxycarbonyl, aminocarbonyl, $C_{1-3}$-alkylaminocarbonyl, di-($C_{1-3}$-alkyl)-aminocarbonyl, aminosulfonyl, $C_{1-3}$-alkylsulfanyl, $C_{1-3}$-alkylsulfinyl, $C_{1-3}$-alkylsulfonyl, hydroxy, $C_{1-3}$-alkyloxy, difluoromethoxy, trifluoromethoxy, phenethyl, phenoxy, or phenyl, while all before mentioned phenyl groups are optionally substituted with 1 or 2 substituents independently of each other selected from fluorine, methyl, methoxy, cyano, carboxy, dimethylaminocarbonyl, or hydroxy,
whilst each of the above-mentioned alkyl or alkylene moieties may be branched or unbranched,
a tautomer, a stereoisomer thereof, a mixture thereof, or a salt thereof,
with the proviso (P1) that the compounds of the general formula (I) wherein R is hydroxycarbonyl, (2-methyl-1-oxo-2-propenyl-1-yl)oxy-, bromo, 4-hydroxyphenyl, 4-hydroxy-3-nitrophenyl, 3-amino-4-hydroxyphenyl, 4-(3-benzyloxy-4-nitro-phenoxy)-phenyl, or 4-(4-amino-3-hydroxy-phenoxy)-phenyl are excluded, and
with the proviso (P2) that the compounds of the general formula (X)

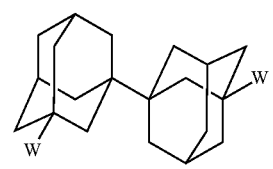

wherein W is methoxycarbonyl, ethoxycarbonyl, n-propoxycarbonyl, i-propoxycarbonyl, n-butyloxycarbonyl, i-butyloxycarbonyl, (1-methyl-propyl-1-oxy)-carbonyl, t-butyloxycarbonyl, n-pentaloxycarbonyl, (3-methylbutyl-1-oxy)-carbonyl, n-hexyloxycarbonyl, n-heptyloxycarbonyl, or n-octyloxycarbonyl, are excluded.

2. The compound according to claim 1 wherein R denotes $C_{1-6}$-alkyl which is optionally mono- or polysubstituted with fluorine and optionally substituted with 1, 2, 3 or 4 substituents independently of each other selected from the group consisting of hydroxy, $C_{1-4}$-alkoxy, (het)aryloxy, $C_{1-4}$-alkylsulfinyl, $C_{5-6}$-cycloalkyl, tetrahydrofuranyl, tetrahydropyranyl, 4-(het)aryl-piperazin-1-yl, 4-$C_{1-4}$-alkylcarbonyl-piperazin-1-yl, 4-$C_{1-4}$-alkylsulfonyl-piperazin-1-yl, morpholin-4-yl, $C_{1-4}$-alkylcarbonylamino, (het)aryl-carbonylamino, pyrrolidin-2-on-1-yl, piperidin-2-on-1-yl, piperazin-2-on-1-yl, piperazin-3-on-1-yl, morpholin-3-on-4-yl, morpholin-2-on-4-yl, cyano, carboxy, $C_{1-4}$-alkyloxycarbonyl, aminocarbonyl, $C_{1-4}$alkylaminocarbonyl, di-($C_{1-4}$-alkyl)aminocarbonyl, (het)aryl-aminocarbonyl, N-(het)aryl-N—($C_{1-3}$-alkyl)-aminocarbonyl and (het)aryl, while each alkyl-residue in the herein before mentioned substituents is optionally mono- or polysubstituted with fluoro and/or monosubstituted with hydroxy, $C_{1-3}$-alkoxy or cyano; and while each herein before mentioned cycloalkyl or cycloheteroalkyl group is optionally mono- or disubstituted independently of each other with $C_{1-3}$-alkyl, fluorine, hydroxy, $C_{1-3}$-alkyloxy, cyano, carboxy, $C_{1-3}$-alkyloxycarbonyl, aminocarbonyl, methylaminocarbonyl, dimethylaminocarbonyl, amino, acetylamino, or (het)aryl, wherein the term (het)aryl is defined as in claim 1.

3. The compound according to claim 1 wherein R denotes $C_{5-6}$-cycloalkyl, tetrahydrofuranyl, tetrahydrofuranonyl, tetrahydropyranyl, tetrahydropyranonyl, pyrrolidinonyl, piperidinonyl, piperazinonyl, 4-($C_{1-3}$-alkyl)-piperazinonyl or morpholinonyl, while each herein before mentioned cycloalkyl or cycloheteroalkyl group is optionally mono- or disubstituted independently of each other with $C_{1-3}$-alkyl, fluorine, hydroxy, $C_{1-3}$-alkyloxy, cyano, carboxy, $C_{1-3}$-alkyloxycarbonyl, aminocarbonyl, methylaminocarbonyl, dimethylaminocarbonyl, amino, acetylamino, or (het)aryl, wherein the term (het)aryl is defined as in claim 1.

4. The compound according to claim 1 wherein R denotes hydroxy, (het)aryloxy, $C_{1-4}$-alkyloxy, (het)aryl-$C_{1-3}$-alkyloxy, cyano-$C_{1-3}$-alkyloxy, carboxy-$C_{1-3}$-alkyloxy, $C_{1-4}$-alkyloxycarbonyl-$C_{1-3}$-alkyloxy, aminocarbonyl-$C_{1-3}$-alkyloxy, $C_{1-4}$-alkylaminocarbonyl-$C_{1-3}$-alkyloxy, di-($C_{1-4}$-alkyl)aminocarbonyl-$C_{1-3}$-alkyloxy, (het)aryl-aminocarbonyl-$C_{1-3}$-alkyloxy, (het)aryl-$C_{1-3}$-alkyl-aminocarbonyl-$C_{1-3}$-alkyloxy, N-(het)aryl-N—($C_{1-3}$-alkyl)-aminocarbonyl-$C_{1-3}$-alkyloxy, N-((het)aryl-$C_{1-3}$-alkyl)-N—($C_{1-3}$-alkyl)-aminocarbonyl-$C_{1-3}$-alkyloxy, pyrrolidin-1-ylcarbonyl-$C_{1-3}$-alkyloxy, piperidin-1-ylcarbonyl-$C_{1-3}$-alkyloxy, piperazin-1-yl-$C_{1-3}$-alkyloxy, 4-($C_{1-4}$-alkyl)-piperazin-1-ylcarbonyl-$C_{1-3}$-alkyloxy, 4-(het)aryl-piperazin-1-ylcarbonyl-$C_{1-3}$-alkyloxy, morpholin-4-ylcarbonyl-$C_{1-3}$-alkyloxy, while each alkyl-residue is optionally mono- or polysubstituted with fluorine and/or monosubstituted with hydroxy, $C_{1-3}$-alkoxy or cyano; and while each herein before mentioned cycloheteroalkyl group is optionally mono- or disubstituted independently of each other with $C_{1-3}$-alkyl, fluorine, hydroxy, $C_{1-3}$-alkyloxy, cyano, carboxy, $C_{1-3}$-alkyloxycarbonyl, aminocarbonyl, methylaminocarbonyl, dimethylaminocarbonyl, amino, acetylamino, or (het)aryl, wherein the term (het)aryl is defined as in claim 1.

5. The compound according to claim 1 wherein R denotes amino, $C_{1-4}$-alkylcarbonylamino, (het)aryl-carbonylamino, (het)aryl-$C_{1-3}$-alkyl-carbonylamino, $C_{1-4}$-alkyloxycarbonylamino, pyrrolidin-1-yl, piperidin-1-yl, piperazin-1-yl, 4-(het)aryl-piperazin-1-yl, 4-$C_{1-4}$-alkylcarbonyl-piperazin-1-yl, 4-(het)aryl-carbonyl-piperazin-1-yl, 4-$C_{1-4}$-alkylsulfonyl-piperazin-1-yl, or morpholin-4-yl; while each alkyl-residue is optionally mono- or polysubstituted with fluorine and/or monosubstituted with hydroxy, $C_{1-3}$-alkoxy or cyano; and while each herein before mentioned cycloheteroalkyl group is optionally mono- or disubstituted independently of each other with $C_{1-3}$-alkyl, fluorine, hydroxy, $C_{1-3}$-alkyloxy, cyano, carboxy, $C_{1-3}$-alkyloxycarbonyl, aminocarbonyl, methylaminocarbonyl, dimethylaminocarbonyl, amino, acetylamino, or (het)aryl, wherein the term (het)aryl is defined as in claim 1.

6. The compound according to claim 1 wherein R denotes cyano, $C_{1-4}$-alkyloxycarbonyl, (het)aryl-carbonyl, aminocarbonyl, $C_{1-4}$-alkylaminocarbonyl, di-($C_{1-4}$-alkyl)aminocarbonyl, N—($C_{5-6}$-cycloalkyl)-N—($C_{1-3}$-alkyl)-aminocarbonyl, N—($C_{5-6}$-cycloheteroalkyl)-N—($C_{1-3}$-alkyl)-aminocarbonyl, (het)arylaminocarbonyl, (het)aryl-$C_{1-3}$-alkyl-aminocarbonyl, N-(het)aryl-N—($C_{1-3}$-alkyl)-aminocarbonyl, N-((het)aryl-$C_{1-3}$-alkyl)-N—($C_{1-3}$-alkyl)-aminocarbonyl, N-((het)aryl-$C_{1-3}$-alkyl)-N—($C_{5-6}$-cycloalkyl)-aminocarbonyl, azetidin-1-ylcarbonyl, pyrrolidin-1-ylcarbonyl, piperidin-1-ylcarbonyl, piperazin-1-ylcarbonyl, morpholin-4-ylcarbonyl, methoxy-aminocarbonyl, or cyanoamino-carbonyl; while each alkyl-residue is optionally mono- or polysubstituted with fluorine and/or monosubstituted with hydroxy, $C_{1-3}$-alkoxy or cyano; and while each herein before mentioned cycloalkyl and cycloheteroalkyl group is optionally mono- or disubstituted independently of each other with $C_{1-4}$-alkyl, fluorine, hydroxy, $C_{1-3}$-alkyloxy, cyano, carboxy, $C_{1-3}$-alkyloxycarbonyl, aminocarbonyl, methylaminocarbonyl, dimethylaminocarbonyl, amino, acetylamino, or (het)aryl, wherein the term (het)aryl is defined as in claim 1.

7. The compound according to wherein R denotes phenyl, furanyl, pyrazolyl, imidazolyl, oxazolyl, triazolyl, oxadiazolyl, tetrazolyl, pyridyl, pyridazinyl, pyrazinyl, pyrimidinyl, benzooxazolyl, benzoimidazolyl, quinazolinyl, or dihydroquinazolinyl, while each of the before mentioned groups is optionally mono- or disubstituted independently of each other with fluorine, cyano, $C_{1-3}$-alkyl, trifluoromethyl, hydroxy, methoxy, methylamino, dimethylamino, acetylamino, methylsulfonylamino, carboxy, aminocarbonyl, methylaminocarbonyl, dimethylaminocarbonyl, phenethyl, or phenyl.

8. A physiologically acceptable salt of a compound according to claim 1 with inorganic or organic acids or bases.

9. A pharmaceutical composition containing one or more compounds according to claim 1 or a compound comprised by the provisos (P1) and (P2) according to claim 1 or one or more physiologically acceptable salts with inorganic or organic acids or bases optionally together with one or more inert carriers and/or diluents.

10. A method of using a compound according to claim 1 or a compound comprised by the provisos (P1) and (P2) according to claim 1 or a physiologically acceptable salt with inorganic or organic acids or bases for the treatment of a 1 metabolic disorder.

11. A process for preparing a compound of formula (I) according to claim 1, characterized in that
a carboxylic acid ester of the general formula II

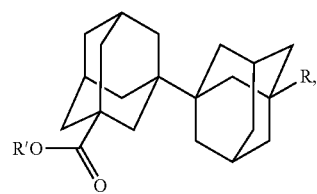

II wherein
the group R is defined as in claim 1, and R' is
$C_{1-6}$-alkyl, $C_{3-6}$-cycloalkyl-$C_{1-3}$-alkyl, $C_{3-6}$-cycloalkyl, $C_{2-6}$-alkenyl, $C_{3-6}$-alkynyl, aryl-$C_{1-3}$-alkyl, aryl, while the alkyl, cycloalkyl, alkenyl, and alkynyl groups mentioned in the definition of the above groups, either alone or as part of another group, optionally are mono- or polysubstituted with fluorine, chlorine, $C_{1-3}$-alkyl, or $C_{1-3}$-alkoxy, and the aryl group mentioned in the definition above is phenyl or naphthyl each option-ally independently of each other mono- or polysubstituted with fluorine, chlorine, bromine, $C_{1-3}$-alkyl, $C_{1-3}$-alkyloxy, nitro, cyano, or di-($C_{1-3}$-alkyl)amino, is hydrolyzed;

and, if necessary any protective group used in the reaction described herein before is cleaved concurrently or subsequently;

and optionally converting the compound of formula (I) into a physiologically acceptable salt thereof.

12. The method of claim 10, wherein the metabolic disorder is selected from the group consisting of type 1 diabetes mellitus, type 2 diabetes mellitus, complications of diabetes, metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, edema and hyperuricaemia.

13. The method of claim 10, wherein the metabolic disorder is selected from diabetes, obesity, and dyslipidemia.

14. The method of claim 10, wherein the metabolic disorder is type 2 diabetes mellitus.

* * * * *